US010259815B2

(12) United States Patent
Cook et al.

(10) Patent No.: US 10,259,815 B2
(45) Date of Patent: Apr. 16, 2019

(54) GABAERGIC LIGANDS AND THEIR USES

(71) Applicant: UWM Research Foundation, Inc., Milwaukee, WI (US)

(72) Inventors: James Cook, Milwaukee, WI (US); Michael Ming-Jin Poe, Vernon, CT (US); Kashi Reddy Methuku, Milwaukee, WI (US); Guanguan Li, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 15/560,002

(22) PCT Filed: Mar. 18, 2016

(86) PCT No.: PCT/US2016/023209
§ 371 (c)(1),
(2) Date: Sep. 20, 2017

(87) PCT Pub. No.: WO2016/154031
PCT Pub. Date: Sep. 29, 2016

(65) Prior Publication Data
US 2018/0065967 A1  Mar. 8, 2018

Related U.S. Application Data

(60) Provisional application No. 62/135,854, filed on Mar. 20, 2015.

(51) Int. Cl.
*A61K 31/5517* (2006.01)
*A61P 25/18* (2006.01)
*C07D 487/04* (2006.01)

(52) U.S. Cl.
CPC ................. *C07D 487/04* (2013.01)

(58) Field of Classification Search
CPC .................. A61K 31/5517; C07D 487/04
USPC ........................... 514/220; 540/562
See application file for complete search history.

(56) References Cited

U.S. PATENT DOCUMENTS

| 2006/0003995 | A1 | 1/2006 | Cook et al. |
| 2009/0093466 | A1 | 4/2009 | Mattson |
| 2009/0163566 | A1 | 6/2009 | Brown et al. |
| 2010/0317619 | A1 | 5/2010 | Cook et al. |
| 2010/0261711 | A1 | 10/2010 | Cook et al. |
| 2012/0295892 | A1 | 11/2012 | Cook et al. |

FOREIGN PATENT DOCUMENTS

WO    2007018660    2/2007

OTHER PUBLICATIONS

Huang, "Synthesis of Optically Active Subtype Selective Benzodiazepine Receptor Ligands," The University of Wisconsin-Milwaukee, 2007.
PCT/US2016/023209 International Search Report and Written Opinion of the International Searching Authority dated Jun. 10, 2016 (9 pages).
PCT/US2016/023209 International Preliminary Report on Patentability dated Oct. 5, 2017 (8 pages).

*Primary Examiner* — Brenda L Coleman
(74) *Attorney, Agent, or Firm* — Michael Best & Friedrich LLP

(57) ABSTRACT

Described herein are α3 or α2 or α2/α3 GABAergic receptor subtype selective ligands, pharmaceutical compositions, and methods of use of such ligands and compositions in treatment of anxiety disorders, epilepsy and schizophrenia with reduced sedative and ataxic side effects. In embodiments, such as α3 or α2 or α2/α3 GABAergic receptor subtype selective ligands lack ester linkages and may be thus relatively insensitive to hydrolysis by esterases.

22 Claims, 15 Drawing Sheets

GABAERGIC LIGANDS AND THEIR USES

CROSS-REFERENCE TO RELATED APPLICATIONS

This application is a U.S. national stage filing under 35 U.S.C. 371 of International Application No. PCT/US2016/023209, filed Mar. 18, 2016, which application claims the benefit of and priority to U.S. Provisional Patent Application Ser. No. 62/135,854, filed Mar. 20, 2015, the entire contents of each of which are hereby incorporated by reference.

STATEMENT REGARDING FEDERALLY SPONSORED RESEARCH OR DEVELOPMENT

This invention was made with government support under RO1 NS076517 and RO1 MH09463 awarded by the National Institutes of Health (NIH). The government has certain rights in the invention.

BACKGROUND

Gamma-aminobutyric acid (GABA) is the major inhibitory neurotransmitter in the central nervous system. GABA receptors are heteromeric, and are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned the number of known members of the mammalian family has grown to 21 including α, β, and γ subunits (6α, 4β, 4γ, 1δ, 1ε, 1π, 1θ, and 3ρ).

A characteristic property of $GABA_A$ receptors is the presence of a number of modulatory sites, one of which is the benzodiazepine (BZ) site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the α1 subunit in combination with a β subunit and γ2. It has been indicated that an α subunit, a β subunit and a γ subunit constitute the minimum requirement for forming a fully functional Benzodiazepine/$GABA_A$ receptor.

Receptor subtype assemblies for BZ-sensitive $GABA_A$ receptors include amongst others the subunit combinations α1β2/3γ2, α2β2/3γ2, α3 β2/3γ2, α4 β2/3γ2, and α5 β2/3γ2. Subtype assemblies containing an 1a subunit (α1β2γ2) are present in most areas of the brain and are thought to account for 40-50% of $GABA_A$ receptors in the rat. Subtype assemblies containing α2 and α3 subunits respectively are thought to account for about 25% and 17% of $GABA_A$ receptors in the rat. Subtype assemblies containing an α5 subunit (α5β3γ2) are expressed predominately in the hippocampus and cortex and are thought to represent about 5% of $GABA_A$ receptors in the rat. Two other major populations are the α2β2/3γ2 and α3β2/3γ2 subtypes as stated above. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain α5-containing subtype assemblies.

The present pharmacology of agonists acting at the BZ site of $GABA_A$ receptors suggests that α1 containing receptors mediate sedation, anticonvulsant activity, ataxia, and anterograde amnesia, while α2 and/or α3 $GABA_A$ receptors mediate anxiolytic activity. α5 containing $GABA_A$ receptors are involved in memory functions (U. Rudolph et al., Nature 1999, 401, 796; K. Löw et al., Science 2000, 290, 131; McKernan Nature Neurosci. 2000, 3, 587; F. Crestani et al., Proc. Nat. Acad. Sci. USA 2002, 99, 8980; M. S. Chambers et al., J. Med. Chem. 2003, 46, 2227).

It is believed that agents acting selectively as benzodiazepine agonists at $GABA_A$/α2, $GABA_A$/α3, and/or $GABA_A$/α5 receptors possess desirable properties. Compounds which are modulators of the benzodiazepine binding site of the $GABA_A$ receptor by acting as benzodiazepine agonists are referred to hereinafter as "$GABA_A$ receptor agonists." The $GABA_A$/α1-selective (α1β2γ2) agonists alpidem and zolpidem are clinically prescribed as hypnotic agents, suggesting that at least some of the sedation associated with known anxiolytic drugs which act at the Benzodiazepine 1 binding site is mediated through $GABA_A$ receptors containing the α1 subunit. Recently, two studies have shown that the majority of additive properties of diazepam are mediated by α1 subtypes (N. A. Ator et. al., J. Pharm. Exp. Thera. 2010, 332, 4-16; K. R. Tan et. al., Nature, 463, 769-774).

It is also known that some benzodiazepine derivatives, such as QH-ii-066, bind with high affinity to $GABA_A$/α5 receptors (Ki<10 nM), intermediate affinity to $GABA_A$/α2 and $GABA_A$/α3 (Ki<50 nM), and poorer affinity to $GABA_A$/α1 receptors (Ki>70 nM), unlike diazepam which binds with high affinity to all four diazepam-sensitive $GABA_A$ receptors (Ki<25 nM), as disclosed in Huang, et al., J. Med. Chem. 2000, 43, 71-95. However, such benzodiazepine derivatives may contain ester linkages, and are thus sensitive to hydrolysis in vivo (e.g., by esterases). What is needed are GABAergic receptor subtype selective ligands that lack ester linkages, and are less sensitive to hydrolysis in vivo by esterases.

SUMMARY

In one aspect, the invention provides a compound of formula (I):
or a salt thereof, wherein:

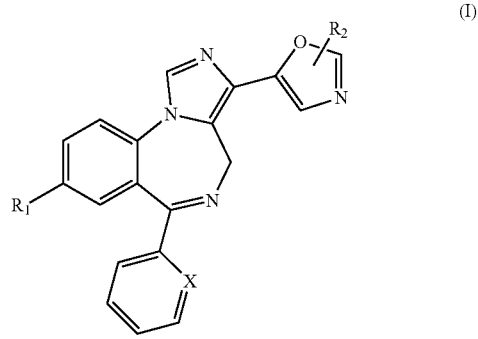

(I)

X is selected from the group consisting of N, C—H, C—F, C—Cl, C—Br, C—I, and C—$NO_2$;

R₁ is selected from the group consisting of —C≡CH, —C≡C—Si(CH₃)₃, -cyclopropyl, and bicycle[1.1.1]pentane

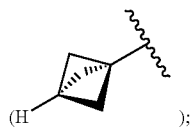

and

R₂ is selected from the group consisting of —H, —CH₃, —CH₂CH₃ and —CH(CH₃)₂.

In some embodiments of the compound of formula (I), R₂ is —H.

In another aspect, the invention provides a compound of formula (II):

or a salt thereof, wherein:

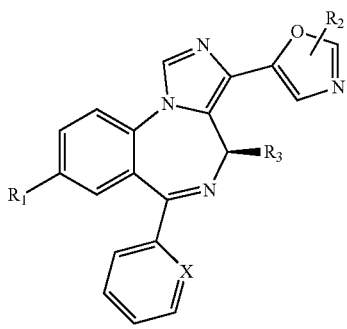

(II)

X is selected from the group consisting of N, C—H, C—F, C—Cl, C—Br, C—I, and C—NO₂;

R₁ is selected from the group consisting of —C≡CH, —C≡C—Si(CH₃)₃, -cyclopropyl, and bicycle[1.1.1]pentane

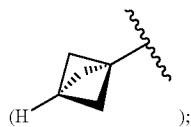

R₂ is selected from the group consisting of —H, —CH₃, —CH₂CH₃, and —CH(CH₃)₂; and R₃ is selected from the group consisting of —H, —CH₃, —CH₂CH₃, —CH(CH₃)₂, —F, —Cl, —CF₃, and —CCl₃.

In some embodiments of the compound of formula (II), R₂ is —H.

In another aspect, the invention provides a compound of formula (III):

or a salt thereof, wherein:

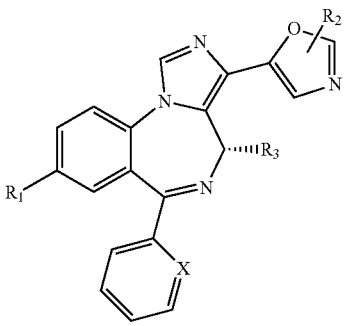

(III)

X is selected from the group consisting of N, C—H, C—F, C—Cl, C—Br, C—I, and C—NO₂;

R₁ is selected from the group consisting of —C≡CH, —C≡C—Si(CH₃)₃, -cyclopropyl, and bicycle[1.1.1]pentane

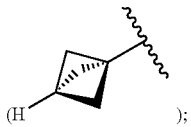

R₂ is selected from the group consisting of —H, —CH₃, —CH₂CH₃, and —CH(CH₃)₂; and R₃ is selected from the group consisting of —H, —CH₃, —CH₂CH₃, —CH(CH₃)₂, —F, —Cl, —CF₃, and —CCl₃.

In some embodiments of the compound of formula (III), R₂ is —H.

In another aspect, the invention provides a method of treating a disorder selected from an anxiety disorder, depression, epilepsy, schizophrenia and neuropathic pain in a subject in need of treatment, comprising administering to the subject an effective amount of a compound of formula (I), (II), or (III).

Other aspects and embodiments are encompassed by the disclosure and will become apparent in light of the following description.

% $MPE$=[(test threshold(g)−control threshold(g)/(pre-CFA threshold−control threshold)]×100.

Figure 13:
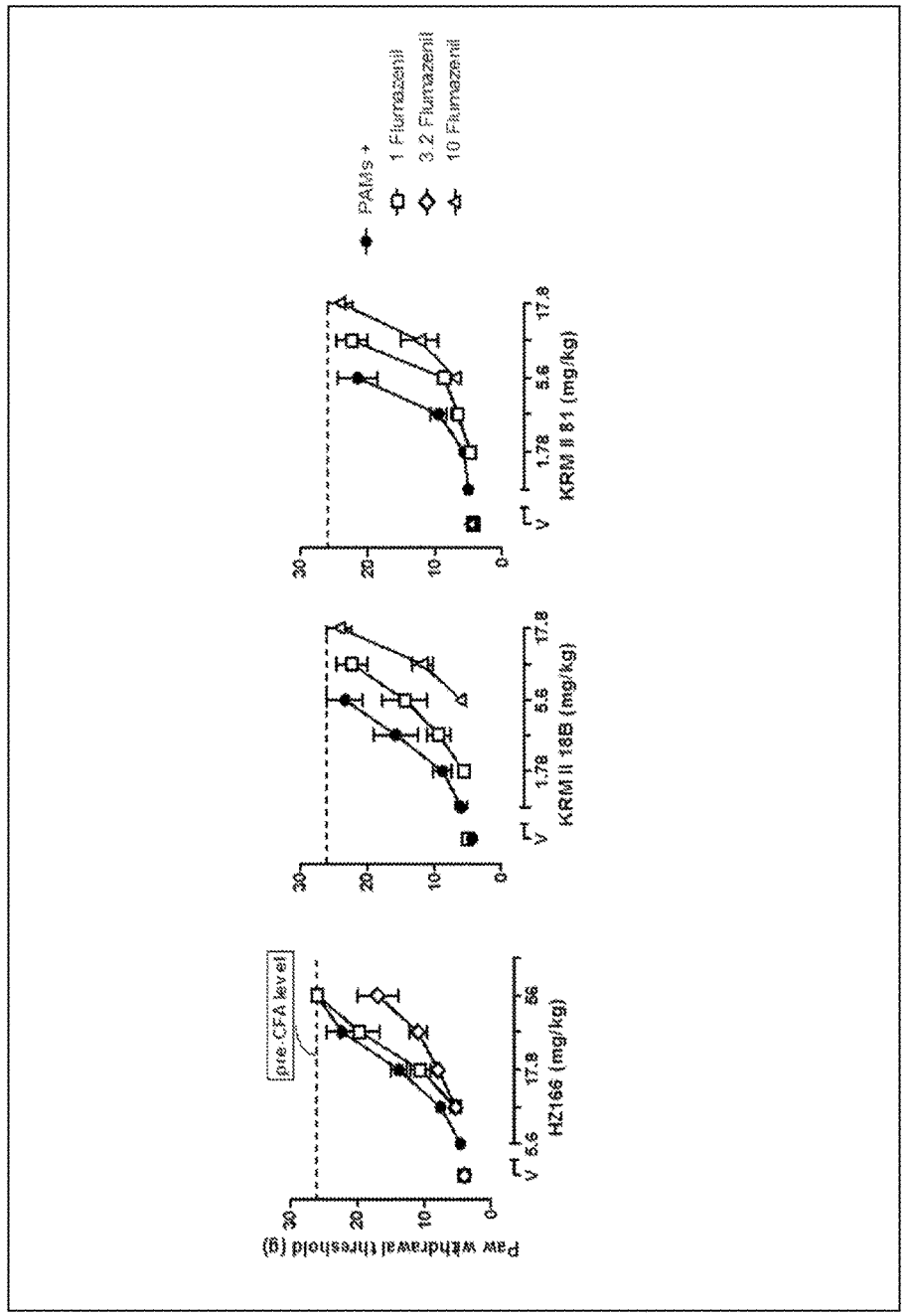

FIG. 13 are graphs of compound concentration versus paw withdrawal threshold, showing that the benzodiazepine site antagonist flumazenil shifted the dose-effect curves of PAMs rightward, indicating the effect is modulated by the benzodiazepine receptor.

Figure 14:
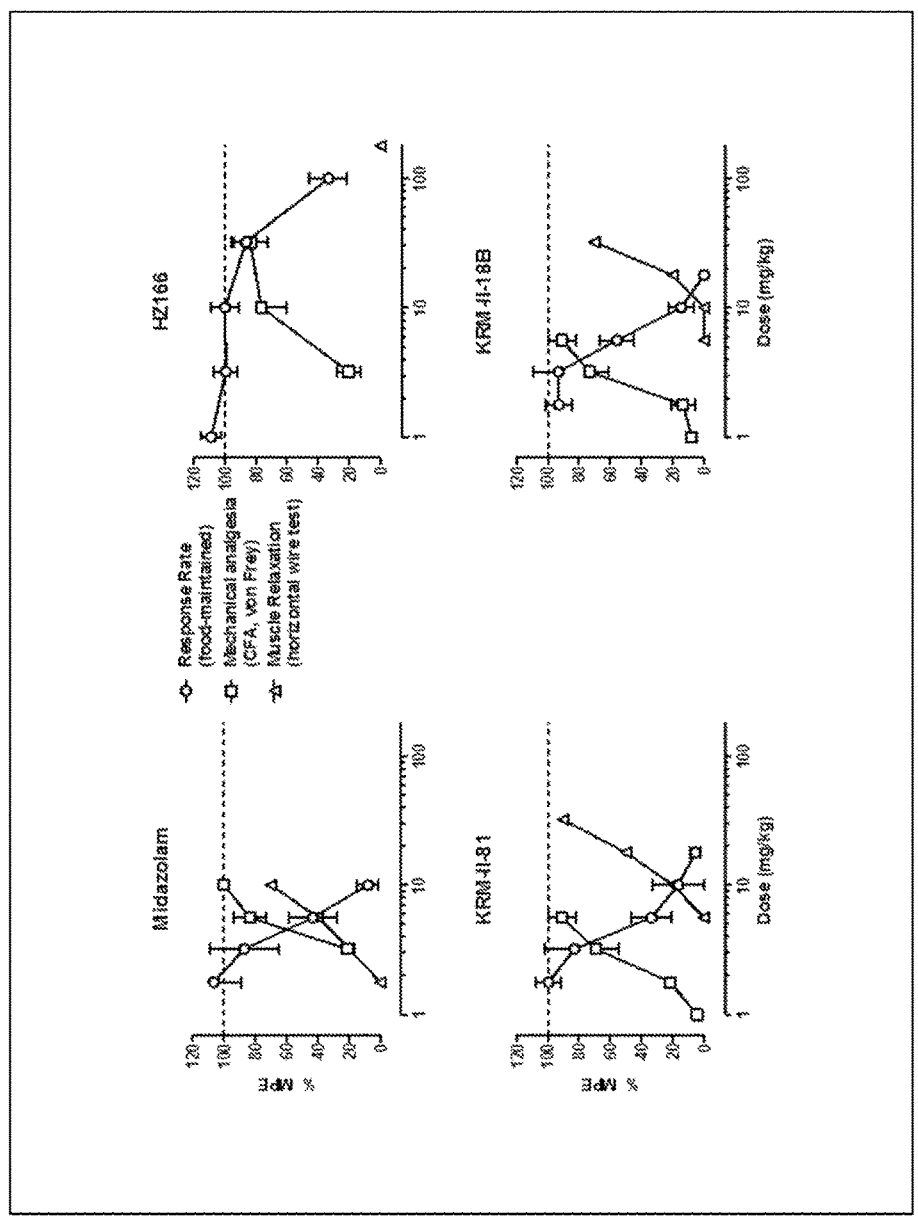

FIG. 14 are graphs of compound concentration or does versus % MPE in a three-assay comparison, showing that midazolam produced antihyperalgesic, rate-suppressing, and muscle-relaxant activity at similar doses. The subunit-selective $GABA_A$ receptor PAMs HZ 166, KRM-II-81, and KRM-II-18B seemed to selectively produce antihyperalgesic effect and produce rate-suppressing and muscle-relaxant activity at much larger doses.

Figure 15:
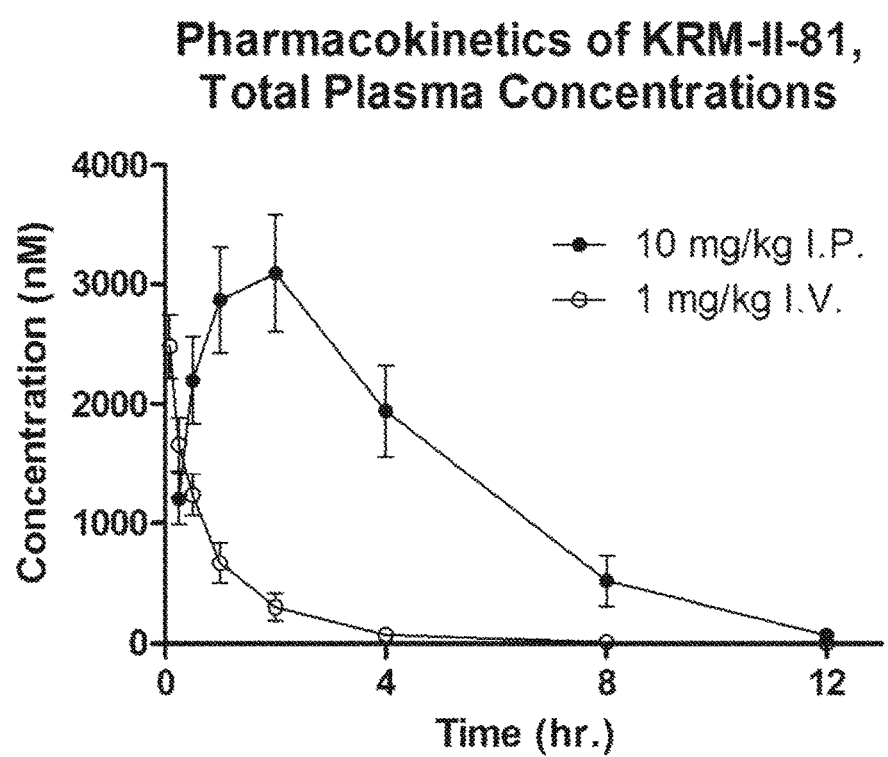

FIG. 15 is a graph of time versus concentration for male Sprague-Dawley rats (n=3 per time point) when given either a 1 mg/kg i.v. or 10 mg/kg i.p. dose. The total plasma concentrations were taken at various time points.

Figure 16:
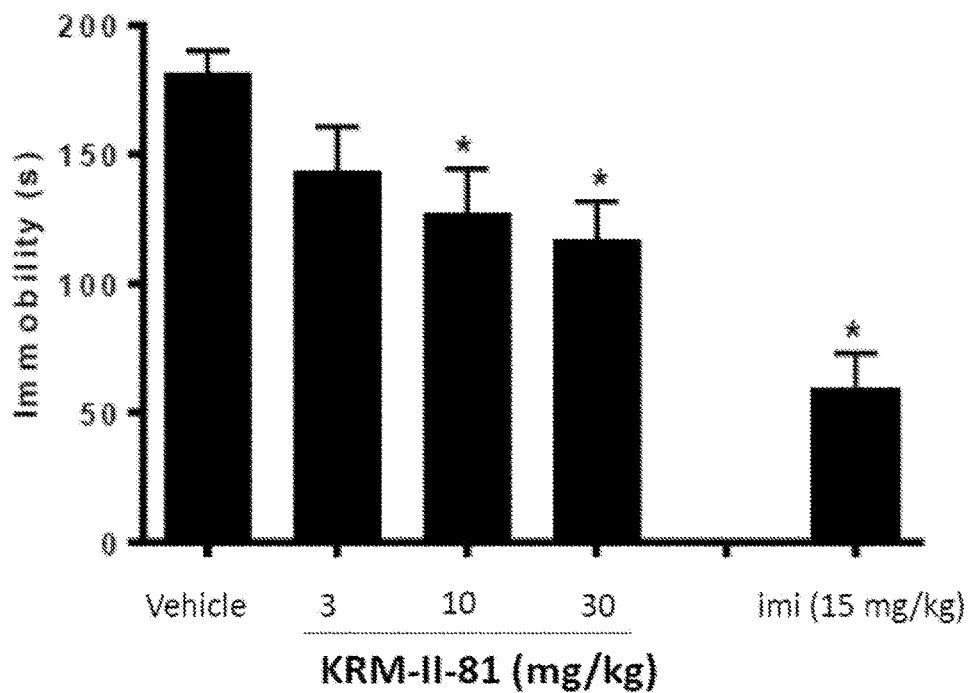

FIG. 16 is a graph of immobility illustrating the antidepressant effects of KRM-II-81 assessed in the forced swim test. Male NIH Swiss mice (n=7-8) were dosed i.p. with vehicle (1% HEC, 0.25% Tween 80, 0.05% antifoam), KRM-II-81 (3, 10, or 30 mg/kg), or imipramine (15 mg/kg) and assessed in the forced swim test. Results were analyzed using ANOVA (Dunnett's test *P<0.05).

DETAILED DESCRIPTION

The present invention provides compounds that may be alpha 2, alpha 3, or alpha2/alpha3 GABAergic receptor subtype selective ligands, pharmaceutical compositions, and methods of use of such ligands and compositions in treatment of anxiety disorders, depression, epilepsy, schizophrenia and neuropathic pain. In embodiments, such alpha 2, alpha 3 or alpha2/alpha3 GABAergic receptor subtype selective ligands lack ester linkages and are thus relatively insensitive to hydrolysis by esterases.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The term "alkenyl" refers to a straight or branched hydrocarbon chain having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. An alkenyl group may be optionally substituted.

The term "alkynyl" refers to a straight or branched hydrocarbon chain having one or more triple bonds. Examples of alkynyl groups include, but are not limited to, ethynyl, propargyl, and 3-hexynyl. One of the triple bond carbons may optionally be the point of attachment of the alkynyl substituent. An alkynyl group may be optionally substituted.

The term "aryl" refers to an aromatic monocyclic, bicyclic, or tricyclic hydrocarbon ring system, wherein any ring atom capable of substitution can be substituted (e.g., with one or more substituents). Examples of aryl moieties include, but are not limited to, phenyl, naphthyl, and anthracenyl.

The term "arylalkyl" refers to an alkyl moiety in which an alkyl hydrogen atom is replaced with an aryl group. Arylalkyl includes groups in which more than one hydrogen atom has been replaced with an aryl group. Examples of arylalkyl groups include benzyl, 2-phenylethyl, 3-phenylpropyl, 9-fluorenyl, benzhydryl, and trityl groups.

The term "cycloalkyl" as used herein refers to nonaromatic, saturated or partially unsaturated cyclic, bicyclic, tricyclic or polycyclic hydrocarbon groups having 3 to 12 carbons (e.g., 3, 4, 5, 6 or 7 carbon atoms). Any ring atom can be substituted (e.g., with one or more substituents). Cycloalkyl groups can contain fused rings. Fused rings are rings that share one or more common carbon atoms. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

The term "halo" or "halogen" as used herein refers to any radical of fluorine, chlorine, bromine or iodine.

The term "haloalkyl" as used herein refers to an alkyl in which one or more hydrogen atoms are replaced with a halogen, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include, but are not limited to, radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines.

The term "heterocyclyl" as used herein refers to a non-aromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include, but are not limited to, radicals of tetrahydrofuran, tetrahydrothiophene, tetrahydropyran, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like.

The term "hydroxy" refers to an —OH radical. The term "alkoxy" refers to an —O— alkyl radical. The term "aryloxy" refers to an —O-aryl radical. The term "haloalkoxy" refers to an —O-haloalkyl radical.

The term "substituent" refers to a group "substituted" on an alkyl, alkenyl, alkynyl, cycloalkyl, heterocyclyl, aryl, arylalkyl or heteroaryl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et and Ph represent methyl, ethyl and phenyl, respectively. A more comprehensive list of the abbreviations used by organic chemists appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

For compounds, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —$CH_2O$— optionally also recites —$OCH_2$—.

In accordance with a convention used in the art, the group:

is used in structural formulas herein to depict the bond that is the point of attachment of the moiety or substituent to the core or backbone structure.

In the context of treating a disorder, the term "effective amount" as used herein refers to an amount of the compound or a composition comprising the compound which is effective, upon single or multiple dose administrations to a subject, in treating a cell, or curing, alleviating, relieving or improving a symptom of the disorder in a subject. An effective amount of the compound or composition may vary according to the application. In the context of treating a disorder, an effective amount may depend on factors such as the disease state, age, sex, and weight of the individual, and the ability of the compound to elicit a desired response in the individual. In an example, an effective amount of a compound is an amount that produces a statistically significant change in a given parameter as compared to a control, such as in cells (e.g., a culture of cells) or a subject not treated with the compound.

It is specifically understood that any numerical value recited herein (e.g., ranges) includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification. These are only examples of what is specifically intended.

Compounds

Compounds may be of the following formula (I):

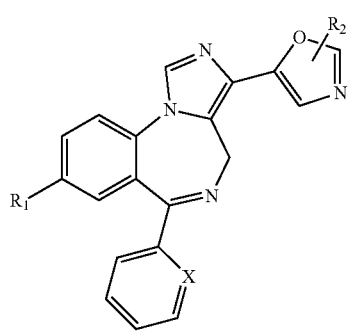
(I)

or a salt thereof, wherein:

X is selected from the group consisting of N, C—H, C—F, C—Cl, C—Br, C—I, and C—NO$_2$;

R$_1$ is selected from the group consisting of —C≡CH, —C≡C—Si(CH$_3$)$_3$, -cyclopropyl, and bicycle[1.1.1]pentane

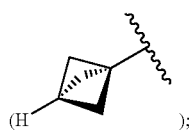
(H );

and

R$_2$ is selected from the group consisting of —H, —CH$_3$, —CH$_2$CH$_3$ and —CH(CH$_3$)$_2$.

In some embodiments, X is N. In some embodiments, X is CH. In some embodiments, X is CF. In some embodiments, X is CCl. In some embodiments, X is CBr. In some embodiments, X is CI. In some embodiments, R$_1$ is —C≡CH. In some embodiments, R$_1$ is —C≡C—Si(CH$_3$)$_3$. In some embodiments, R$_1$ is -cyclopropyl. In some embodiments, R$_1$ is bicycle[1.1.1]pentane. In some embodiments, R$_2$ is —H. In some embodiments, R$_2$ is —CH$_3$. In some embodiments, R$_2$ is —CH$_2$CH$_3$. In some embodiments, R$_2$ is —CH(CH$_3$)$_2$. In particular embodiments, in compounds of formula (I), R$_2$ is H.

Compounds may be of the following formula (II):

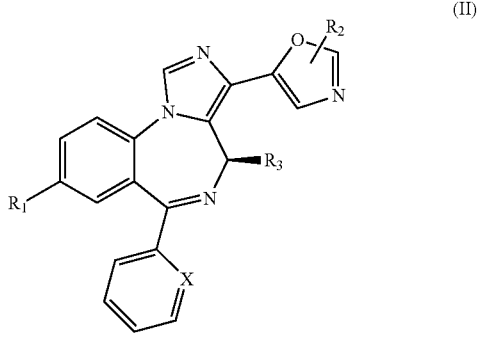
(II)

or a salt thereof, wherein:

X is selected from the group consisting of N, C—H, C—F, C—Cl, C—Br, C—I, and C—NO$_2$;

R$_1$ is selected from the group consisting of —C≡CH, —C≡C—Si(CH$_3$)$_3$, -cyclopropyl, and bicycle[1.1.1]pentane

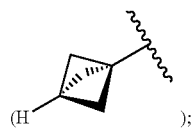
(H );

R$_2$ is selected from the group consisting of —H, —CH$_3$, —CH$_2$CH$_3$, and —CH(CH$_3$)$_2$; and R$_3$ is selected from the group consisting of —H, —CH$_3$, —CH$_2$CH$_3$, —CH(CH$_3$)$_2$, —F, —Cl, —CF$_3$, and —CCl$_3$.

In some embodiments, X is N. In some embodiments, X is CH. In some embodiments, X is CF. In some embodiments, X is CCl. In some embodiments, X is CBr. In some embodiments, X is CI. In some embodiments, R$_1$ is —C≡CH. In some embodiments, R$_1$ is —C≡C—Si(CH$_3$)$_3$. In some embodiments, R$_1$ is -cyclopropyl. In some embodiments, R$_1$ is bicycle[1.1.1]pentane. In some embodiments, R$_2$ is —H. In some embodiments, R$_2$ is —CH$_3$. In some embodiments, R$_2$ is —CH$_2$CH$_3$. In some embodiments, R$_2$ is —CH(CH$_3$)$_2$. In some embodiments, R$_3$ is —H. In some embodiments, R$_3$ is —CH$_3$. In some embodiments, R$_3$ is —CH$_2$CH$_3$. In some embodiments, R$_3$ is —CH(CH$_3$)$_2$. In some embodiments, R$_3$ is F. In some embodiments, R$_3$ is Cl. In some embodiments, R$_3$ is —CF$_3$. In some embodiments, R$_3$ is —CCl$_3$.

In particular embodiments, in compounds of formula (II), R$_2$ is H.

Compounds may be of the following formula (III):

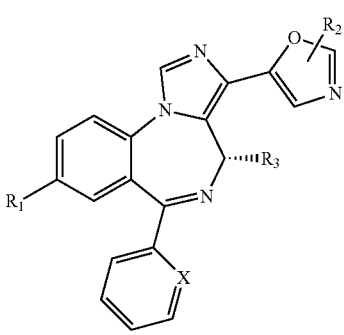
(III)

or a salt thereof, wherein:

X is selected from the group consisting of N, C—H, C—F, C—Cl, C—Br, C—I, and C—NO$_2$;

R$_1$ is selected from the group consisting of —C≡CH, —C≡C—Si(CH$_3$)$_3$, -cyclopropyl, and bicycle[1.1.1]pentane (H⎯⟨bicyclopentane⟩⎯);

R$_2$ is selected from the group consisting of —H, —CH$_3$, —CH$_2$CH$_3$, and —CH(CH$_3$)$_2$; and R$_3$ is selected from the group consisting of —H, —CH$_3$, —CH$_2$CH$_3$, —CH(CH$_3$)$_2$, —F, —Cl, —CF$_3$, and —CCl$_3$.

In some embodiments, X is N. In some embodiments, X is CH. In some embodiments, X is CF. In some embodiments, X is CCl. In some embodiments, X is CBr. In some embodiments, X is CI. In some embodiments, R$_1$ is —C≡CH. In some embodiments, R$_1$ is —C≡C—Si(CH$_3$)$_3$. In some embodiments, R$_1$ is -cyclopropyl. In some embodiments, R$_1$ is bicycle[1.1.1]pentane. In some embodiments, R$_2$ is —H. In some embodiments, R$_2$ is —CH$_3$. In some embodiments, R$_2$ is —CH$_2$CH$_3$. In some embodiments, R$_2$ is —CH(CH$_3$)$_2$. In some embodiments, R$_3$ is —H. In some embodiments, R$_3$ is —CH$_3$. In some embodiments, R$_3$ is —CH$_2$CH$_3$. In some embodiments, R$_3$ is —CH(CH$_3$)$_2$. In some embodiments, R$_3$ is F. In some embodiments, R$_3$ is Cl. In some embodiments, R$_3$ is —CF$_3$. In some embodiments, R$_3$ is —CCl$_3$.

In particular embodiments, in compounds of formula (III), R$_2$ is H.

Compounds may be of the following formula (IV):

(IV)

or a salt thereof, wherein:

X is selected from the group consisting of N, C—H, C—F, C—Cl, C—Br, C—I, and C—NO$_2$;

R$_{11}$ is Br; and

R$_{12}$ is selected from the group consisting of —H, —CH$_3$, —CH$_2$CH$_3$ and —CH(CH$_3$)$_2$.

In some embodiments, X is N. In some embodiments, X is CH. In some embodiments, X is CF. In some embodiments, X is CCl. In some embodiments, X is CBr. In some embodiments, X is CI. In some embodiments, R$_2$ is —H. In some embodiments, R$_2$ is —CH$_3$. In some embodiments, R$_{12}$ is —CH$_2$CH$_3$. In some embodiments, R$_{12}$ is —CH(CH$_3$)$_2$.

In particular embodiments, in compounds of formula (IV), R$_{12}$ is H.

Compounds may be of the following formula (V):

(V)

or a salt thereof, wherein:

X is selected from the group consisting of N, C—H, C—F, C—Cl, C—Br, C—I, and C—NO$_2$;

R$_{11}$ is Br;

R$_{12}$ is selected from the group consisting of —H, —CH$_3$, —CH$_2$CH$_3$, and —CH(CH$_3$)$_2$; and R$_{13}$ is selected from the group consisting of —H, —CH$_3$, —CH$_2$CH$_3$, —CH(CH$_3$)$_2$, —F, —Cl, —CF$_3$, and —CCl$_3$.

In some embodiments, X is N. In some embodiments, X is CH. In some embodiments, X is CF. In some embodiments, X is CCl. In some embodiments, X is CBr. In some embodiments, X is CI. In some embodiments, R$_{12}$ is —H. In some embodiments, R$_{12}$ is —CH$_3$. In some embodiments, R$_{12}$ is —CH$_2$CH$_3$. In some embodiments, R$_{12}$ is —CH(CH$_3$)$_2$. In some embodiments, R$_{13}$ is —H. In some embodiments, R$_{13}$ is —CH$_3$. In some embodiments, R$_{13}$ is —CH$_2$CH$_3$. In some embodiments, R$_{13}$ is —CH(CH$_3$)$_2$. In some embodiments, R$_{13}$ is F. In some embodiments, R$_{13}$ is Cl. In some embodiments, R$_{13}$ is —CF$_3$. In some embodiments, R$_{13}$ is —CCl$_3$.

In particular embodiments, in compounds of formula (V), R$_{12}$ is H.

Compounds may be of the following formula (VI):

(VI)

or a salt thereof, wherein:

X is selected from the group consisting of N, C—H, C—F, C—Cl, C—Br, C—I, and C—NO$_2$;

R$_{11}$ is Br;

R$_{12}$ is selected from the group consisting of —H, —CH$_3$, —CH$_2$CH$_3$, and —CH(CH$_3$)$_2$; and R$_{13}$ is selected from the group consisting of —H, —CH$_3$, —CH$_2$CH$_3$, —CH(CH$_3$)$_2$, —F, —Cl, —CF$_3$, and —CCl$_3$.

In some embodiments, X is N. In some embodiments, X is CH. In some embodiments, X is CF. In some embodiments, X is CCl. In some embodiments, X is CBr. In some embodiments, X is CI. In some embodiments, $R_{12}$ is —H. In some embodiments, $R_{12}$ is —CH$_3$. In some embodiments, $R_{12}$ is —CH$_2$CH$_3$. In some embodiments, $R_{12}$ is —CH(CH$_3$)$_2$. In some embodiments, $R_{13}$ is —H. In some embodiments, $R_{13}$ is —CH$_3$. In some embodiments, $R_{13}$ is —CH$_2$CH$_3$. In some embodiments, $R_{13}$ is —CH(CH$_3$)$_2$. In some embodiments, $R_{13}$ is F. In some embodiments, $R_{13}$ is Cl. In some embodiments, $R_{13}$ is —CF$_3$. In some embodiments, $R_{13}$ is —CCl$_3$.

In particular embodiments, in compounds of formula (VI), $R_2$ is H.

Suitable compounds include the following:

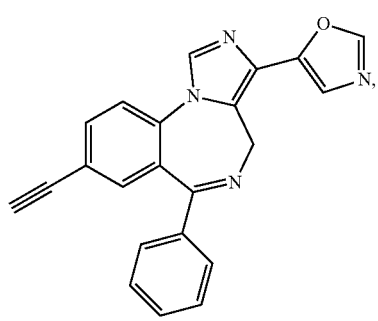

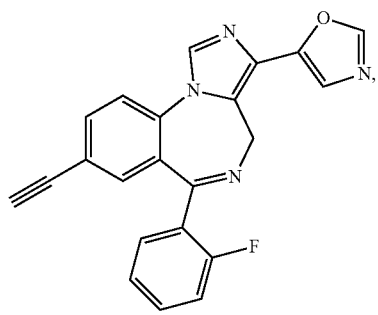

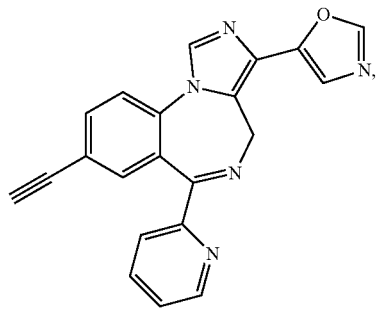

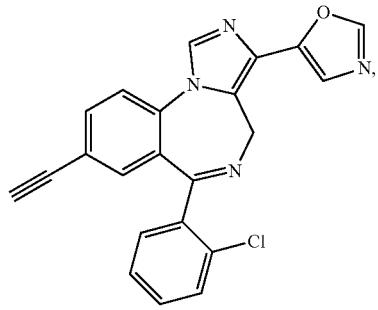

-continued

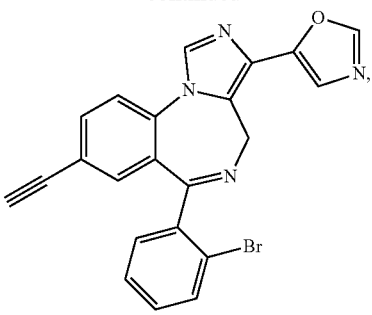

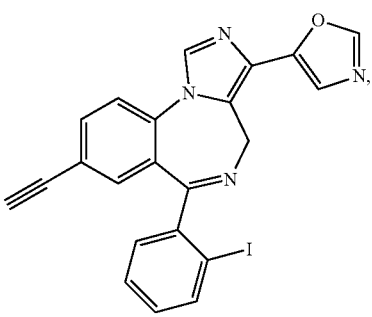

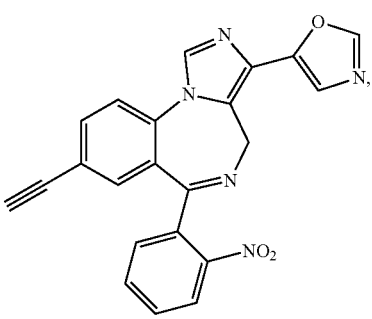

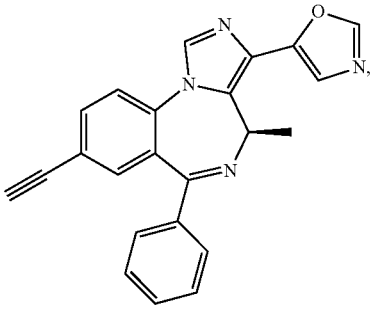

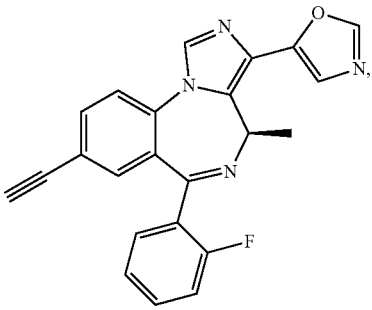

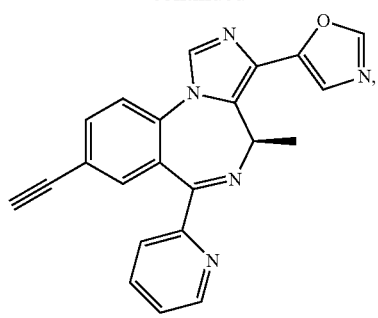
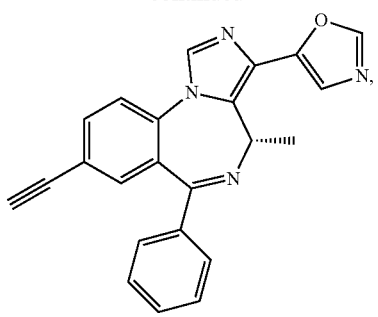
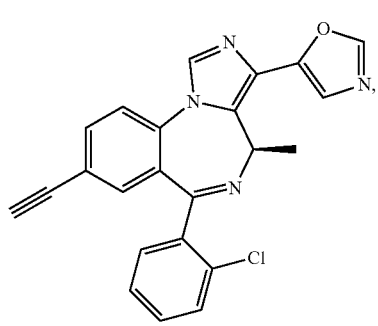
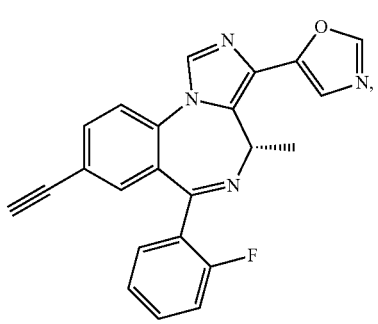
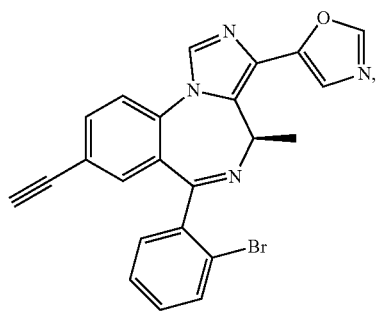
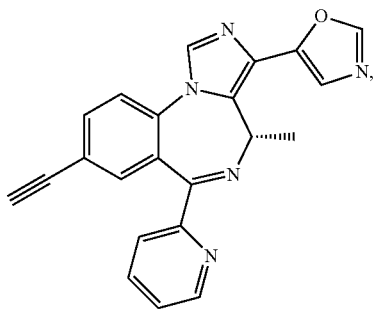
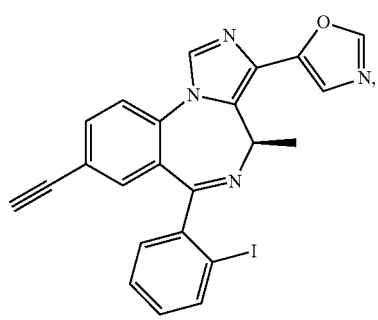
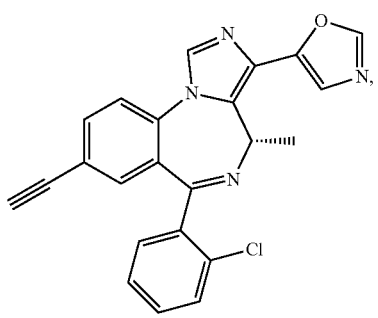
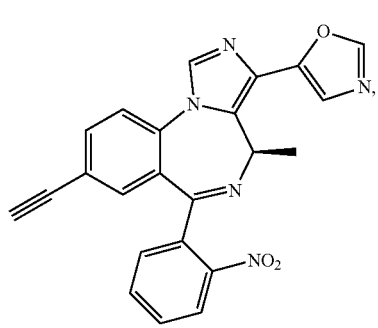
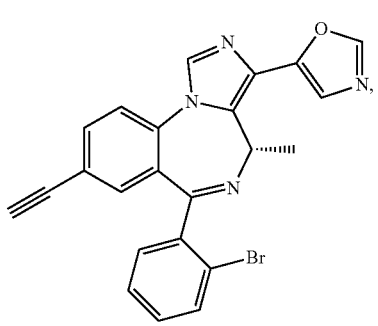

17
-continued
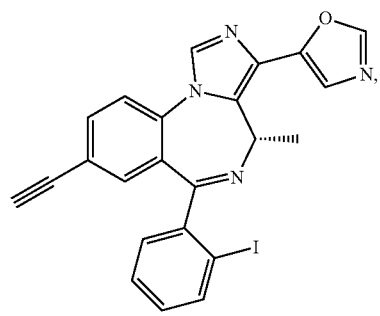
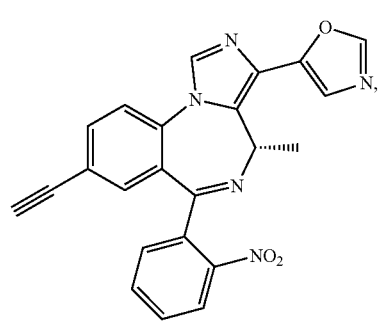
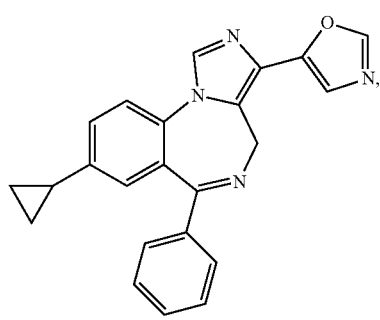
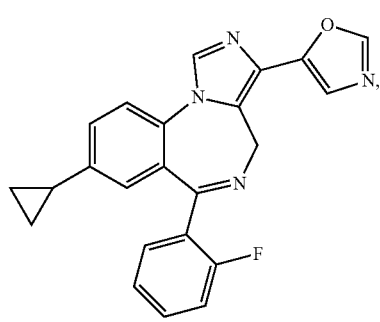
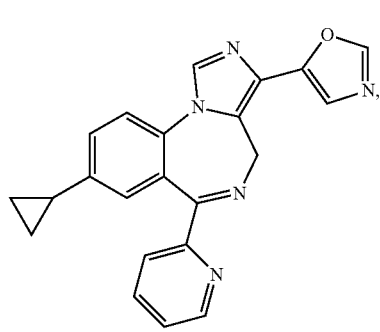
18
-continued
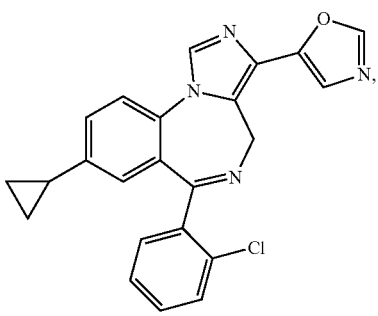
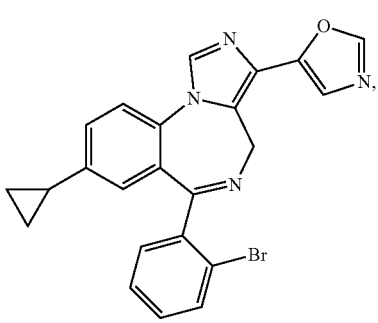
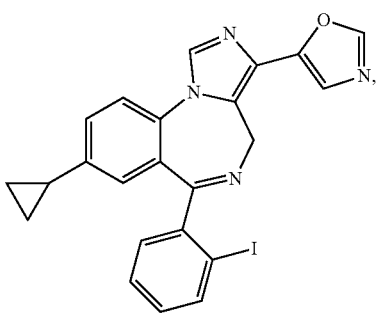
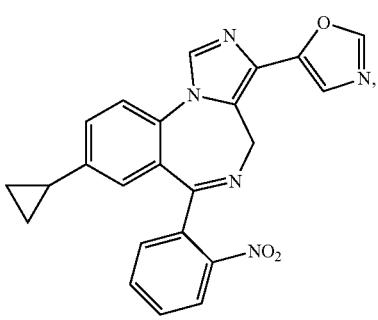
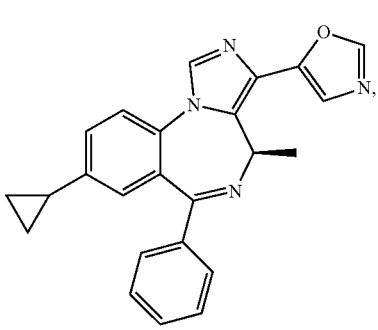

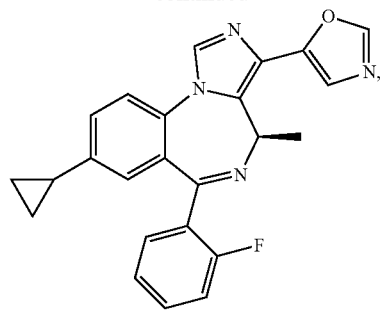
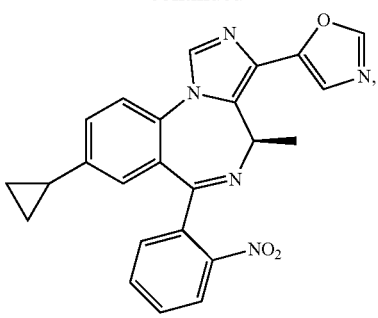
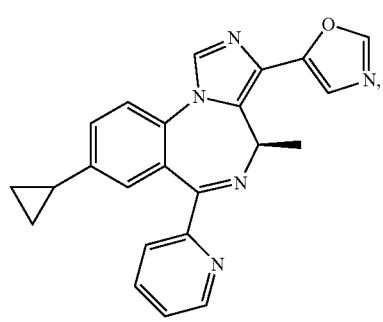
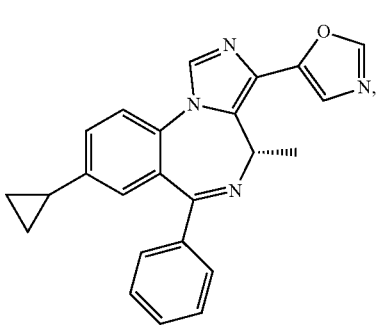
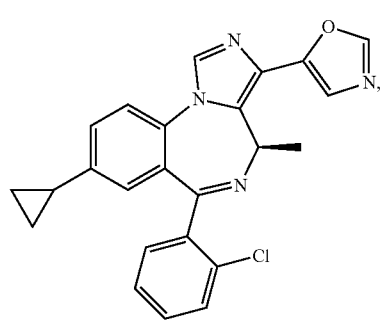
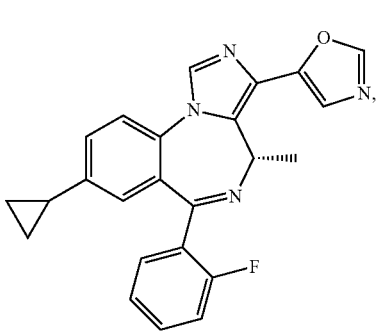
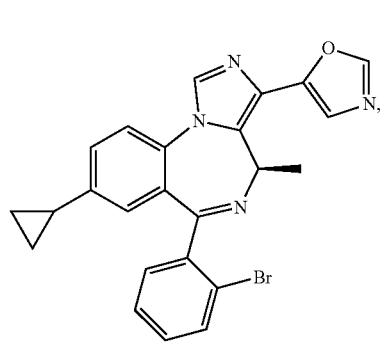
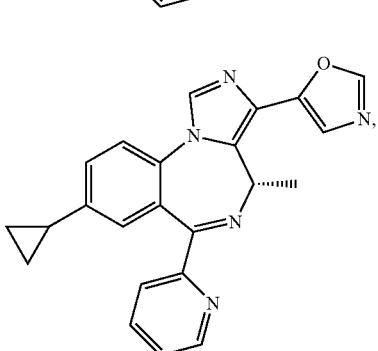
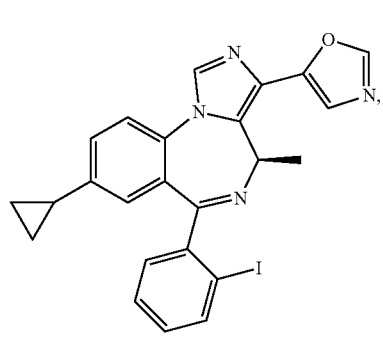
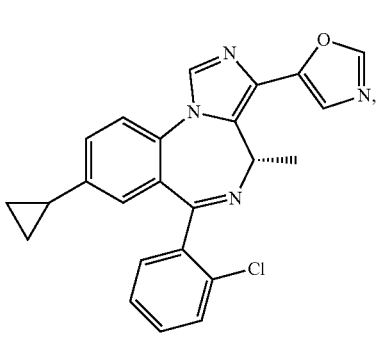

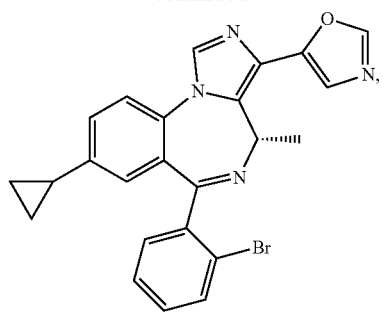
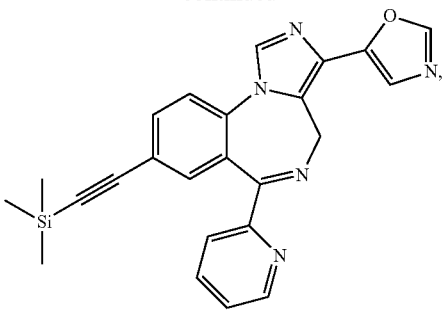
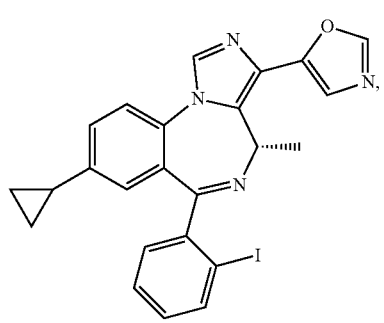
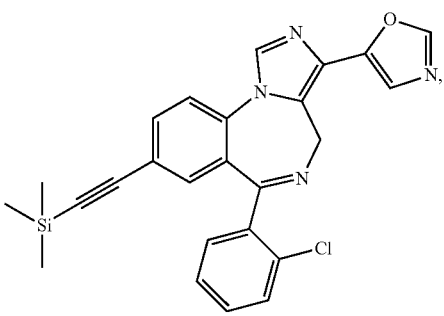
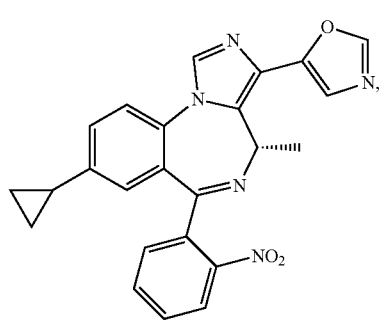
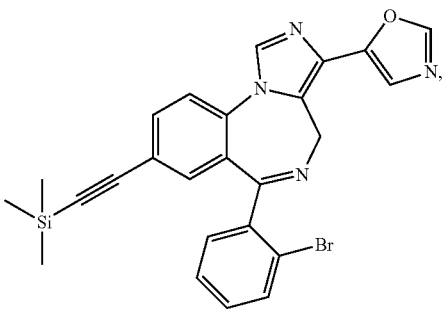
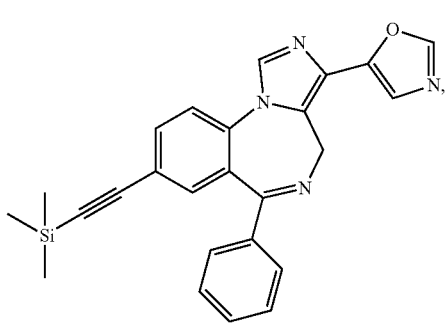
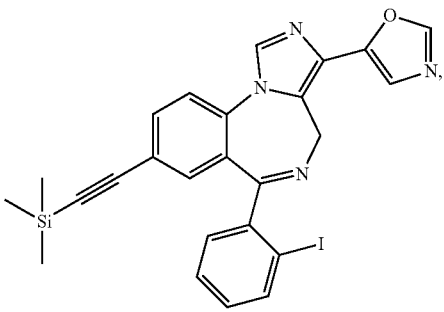
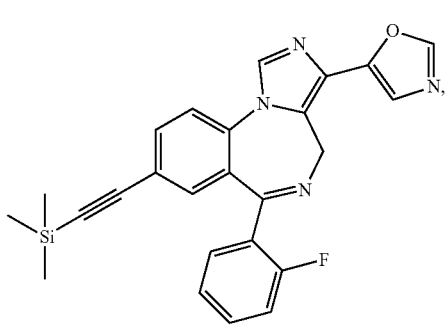
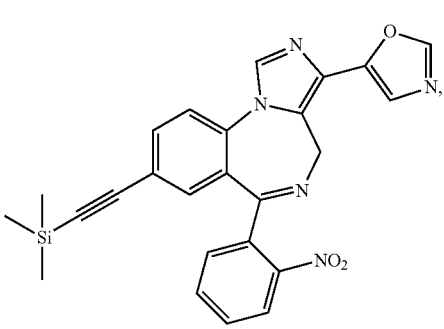

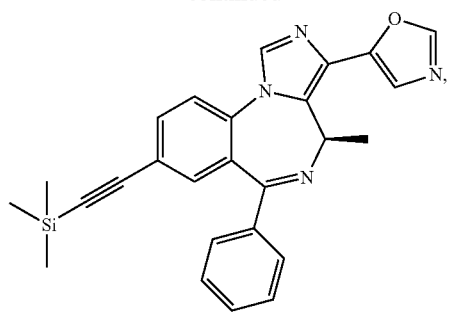
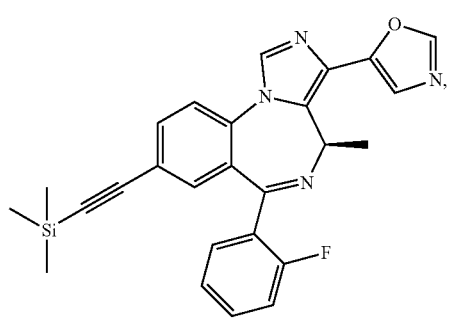
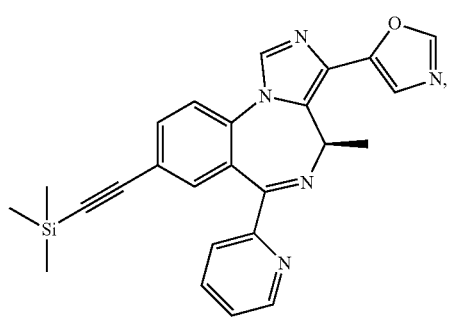
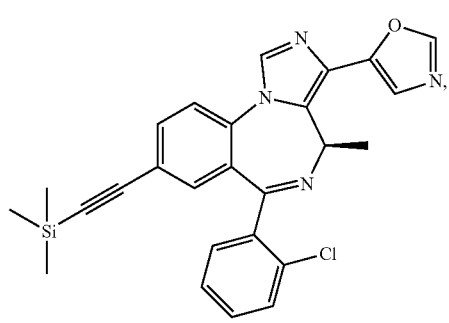
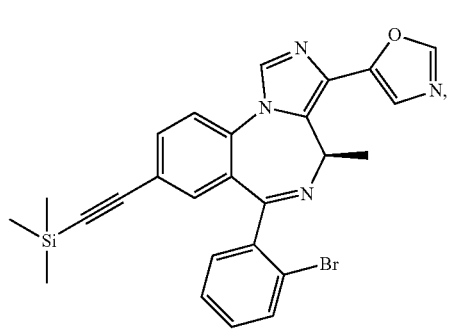
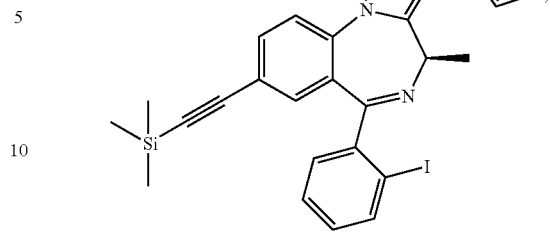
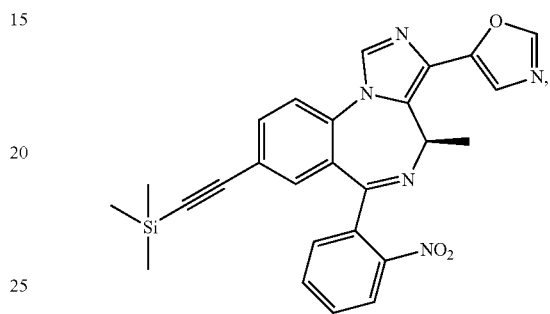
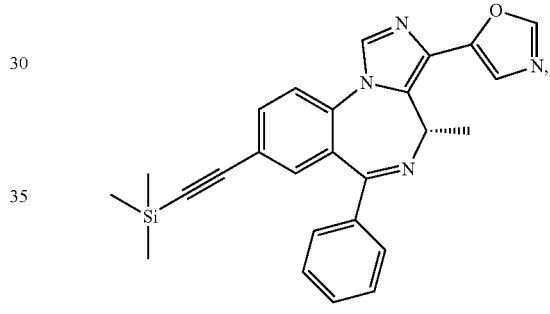
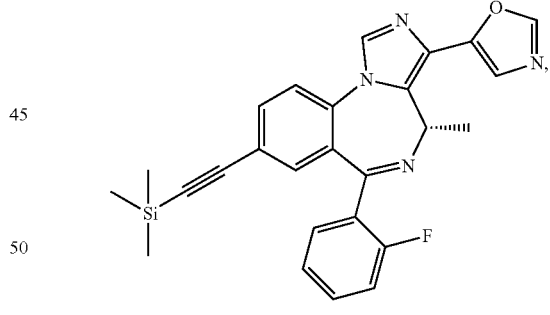
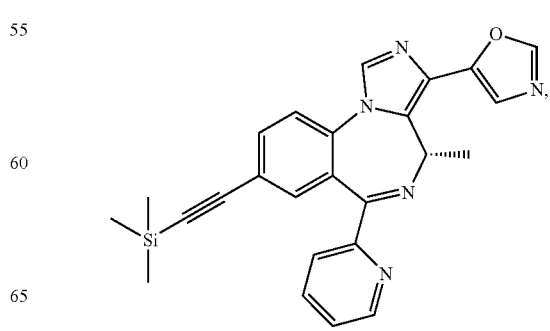

-continued
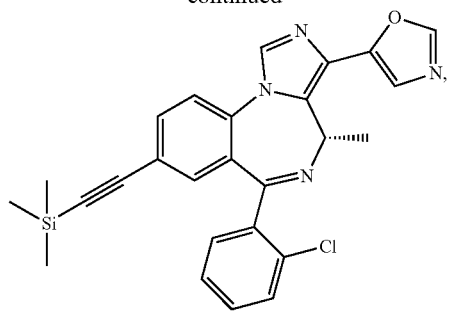
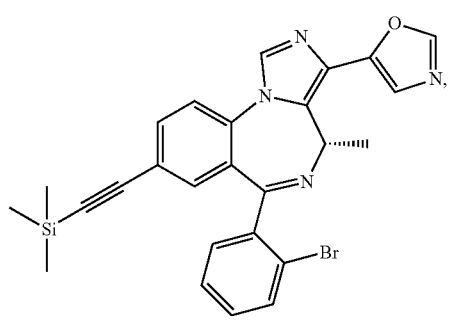
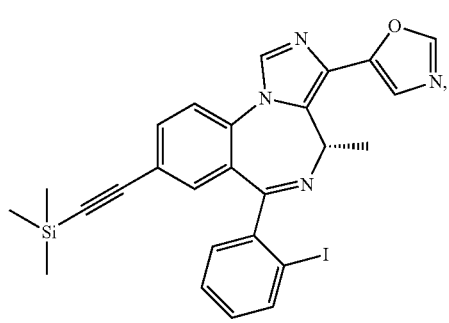
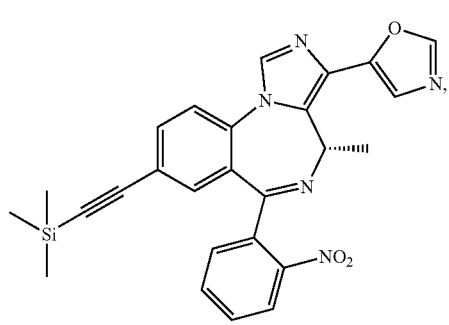
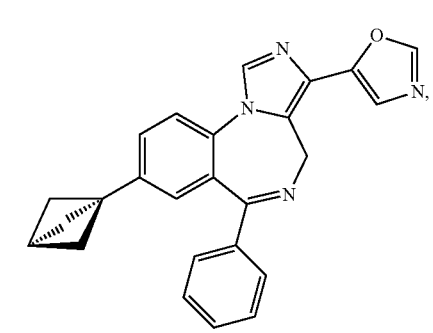
-continued
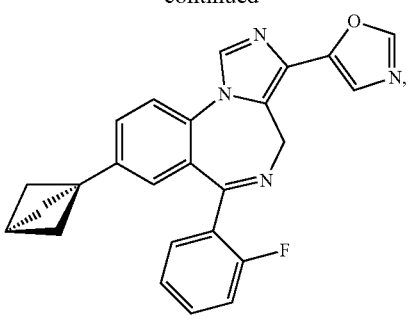
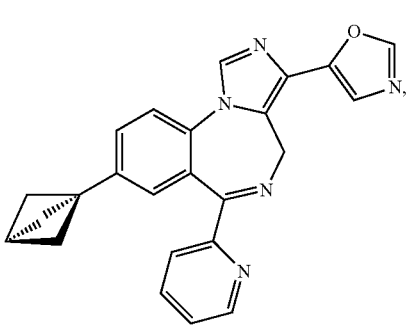
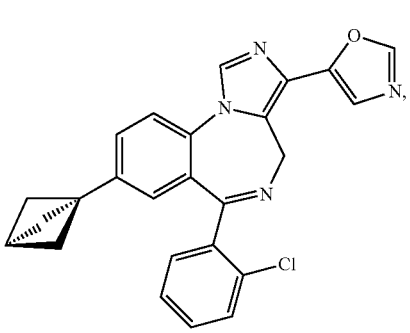
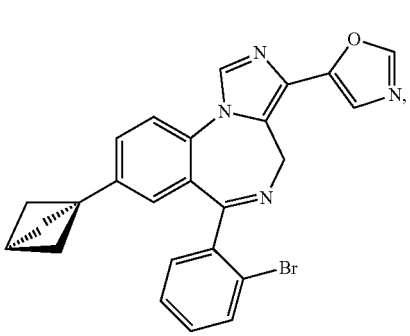
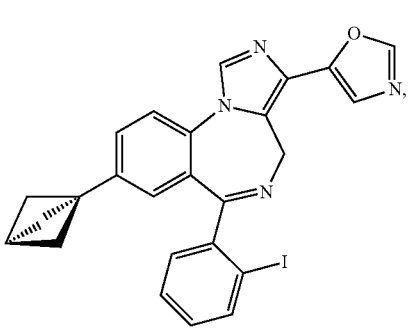

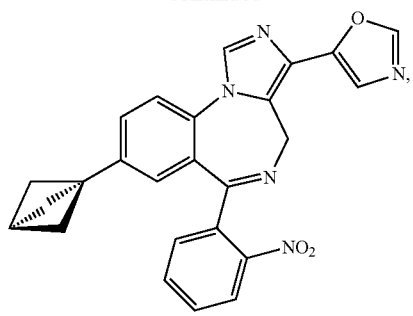
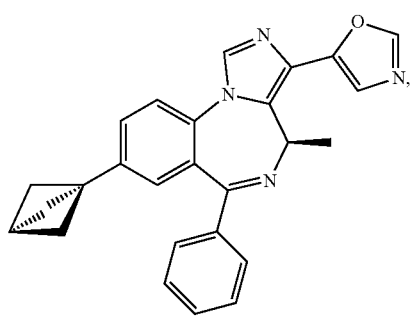
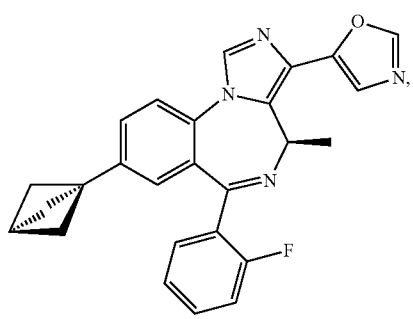
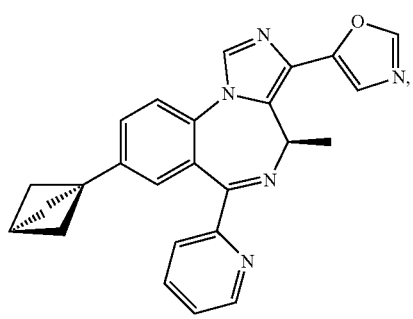
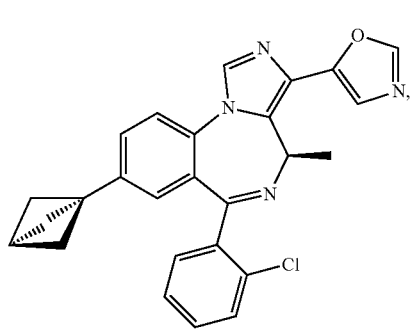
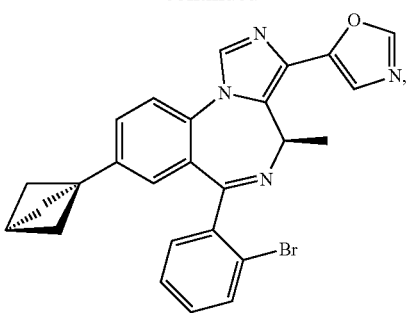
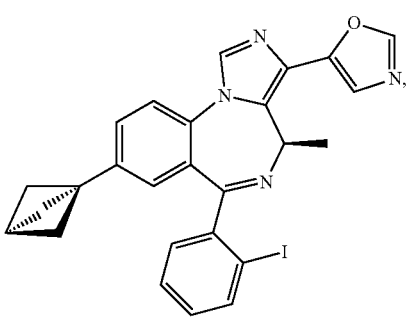
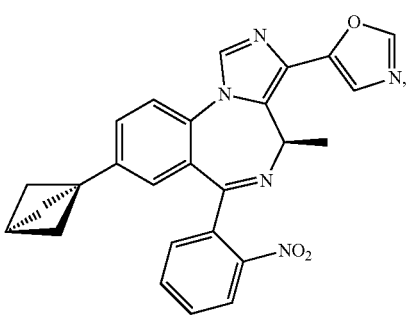
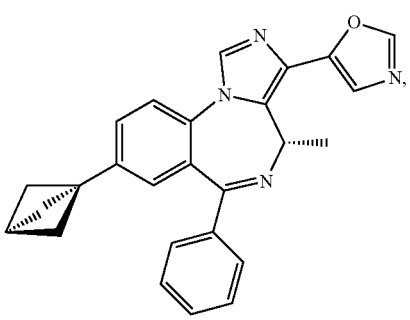
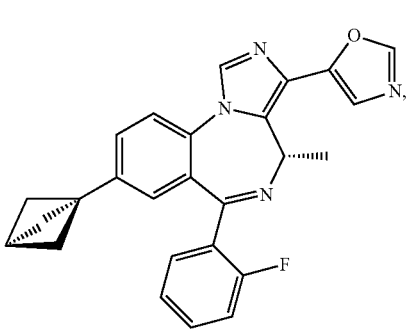

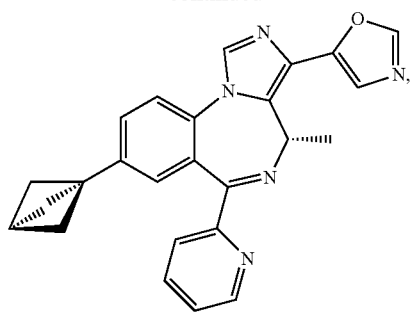
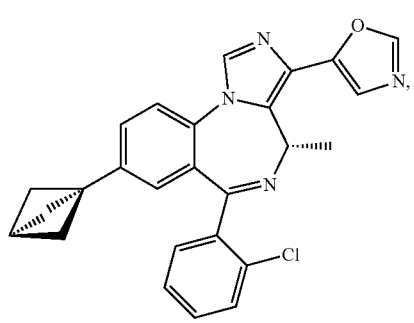
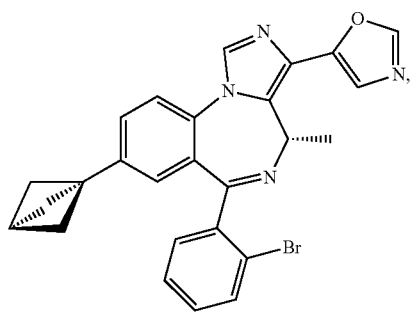
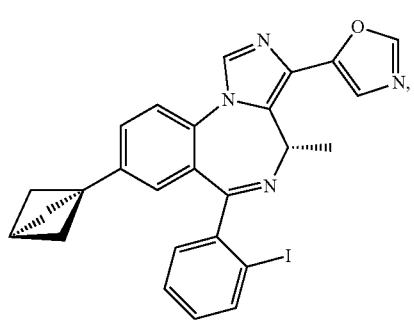
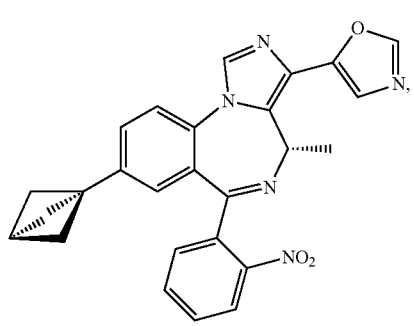
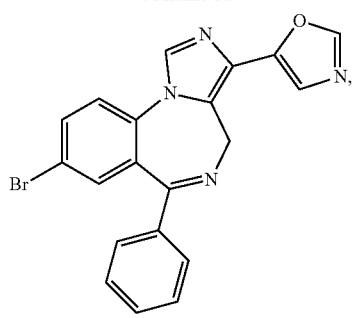
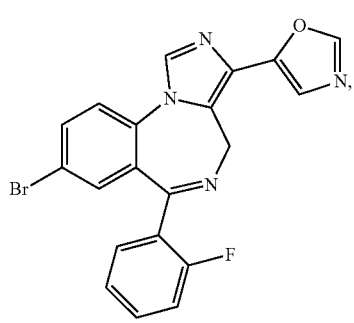
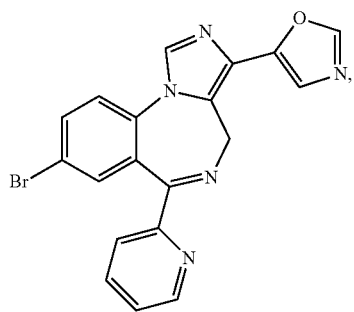
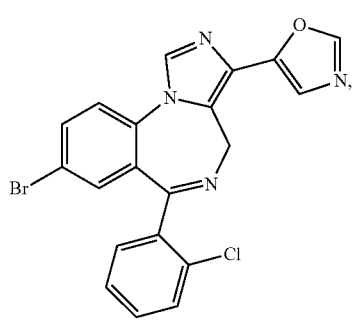
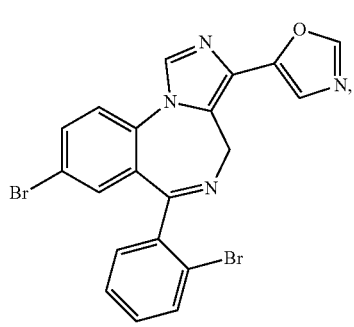

31
-continued
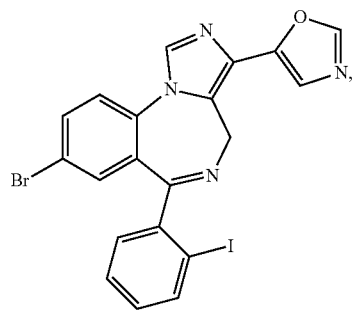
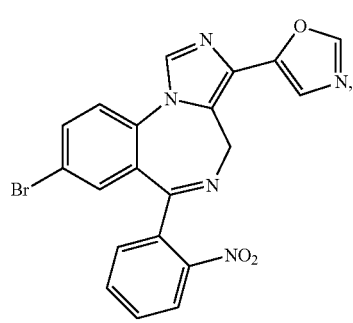
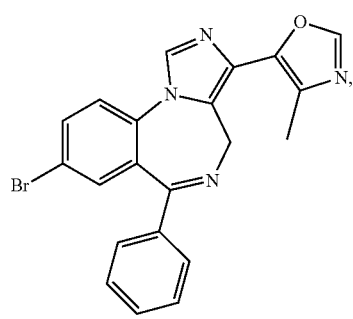
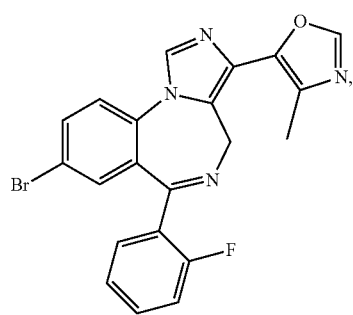
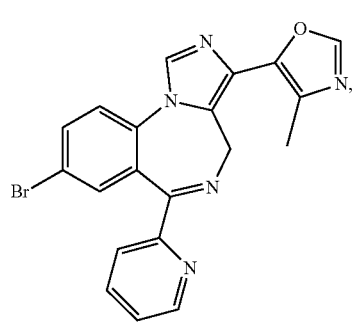
32
-continued
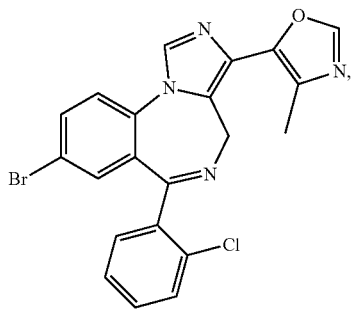
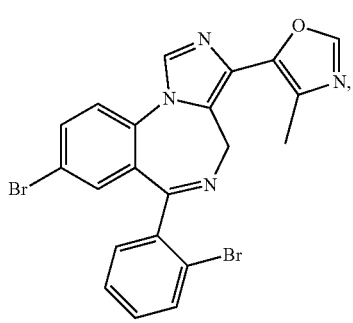
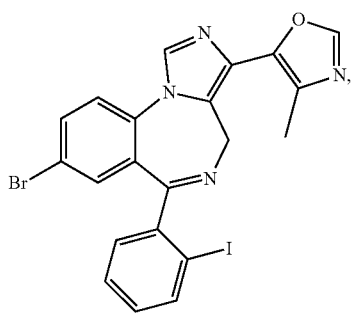
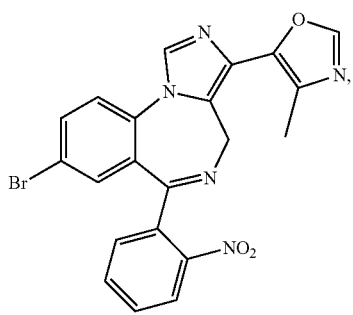
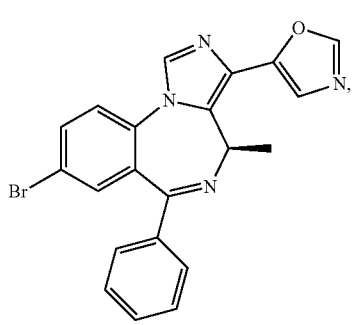

33
-continued
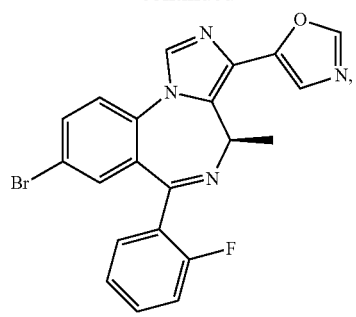
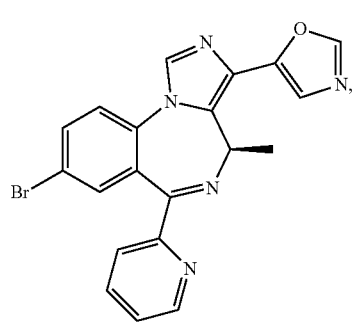
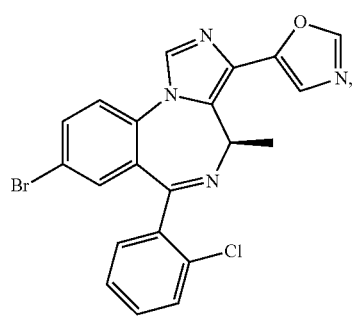
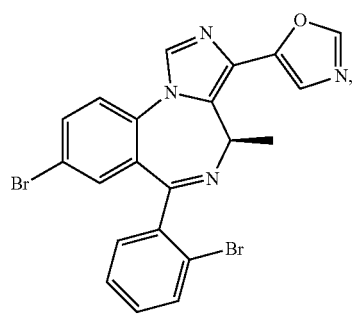
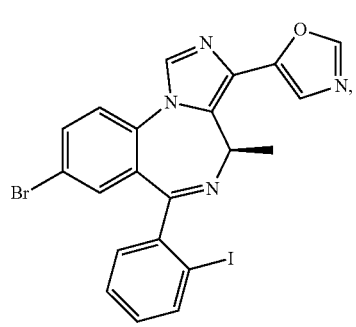
34
-continued
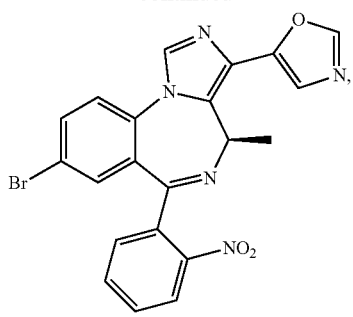
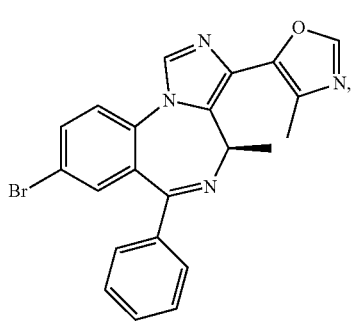
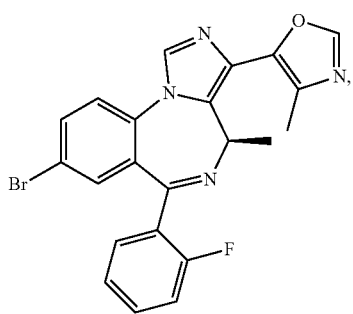
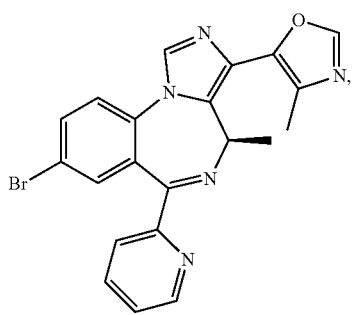
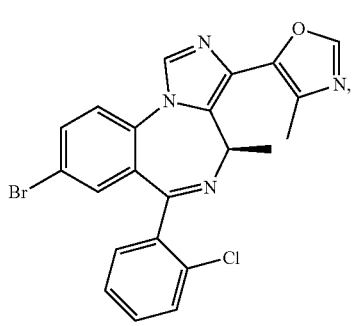

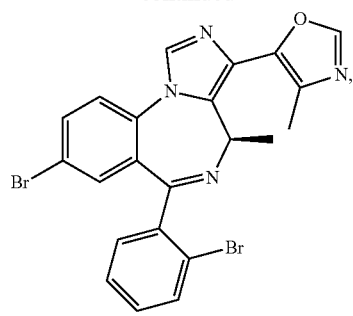
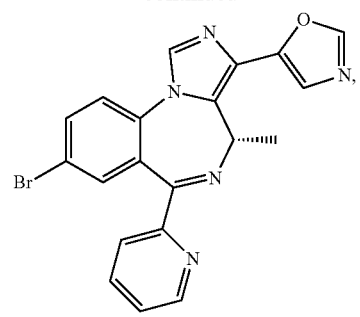
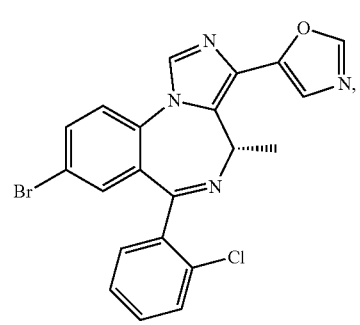
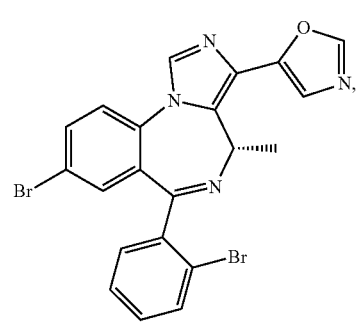
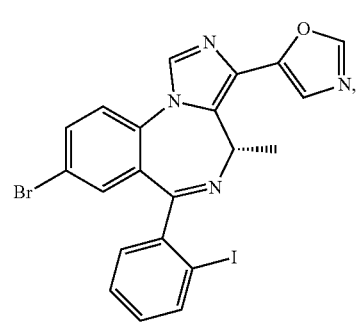
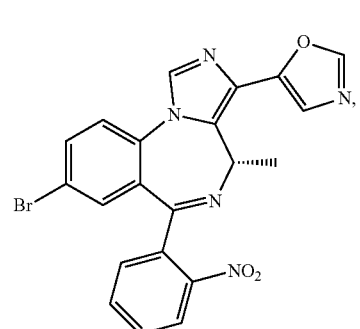

-continued

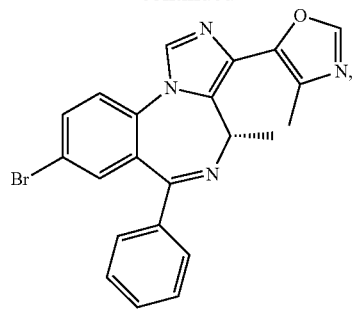

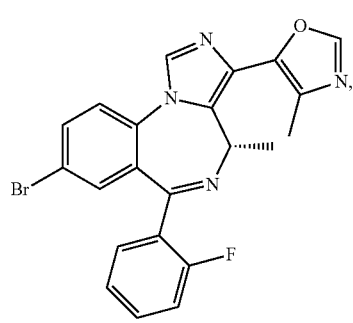

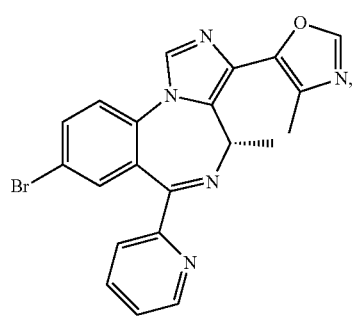

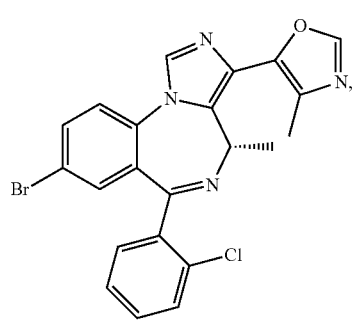

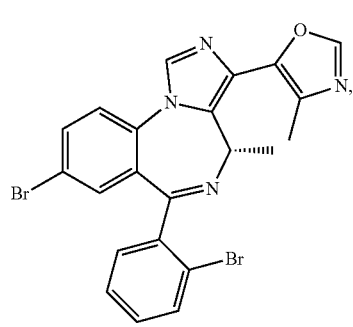

-continued

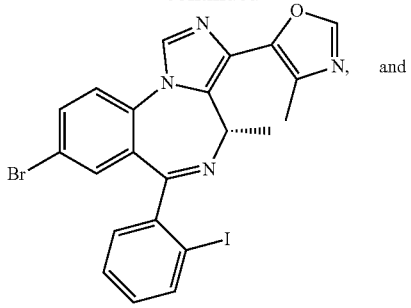

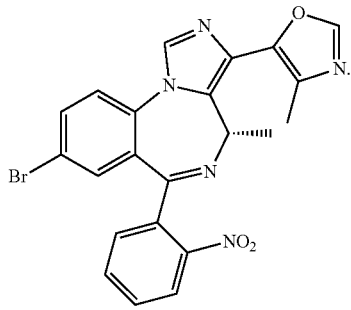 [SMILES: Cc1ncoc1-c1ncn2c1[C@H](C)N=C(c1ccccc1[N+](=O)[O-])c1cc(Br)ccc1-2]

In some embodiments, the compound is not

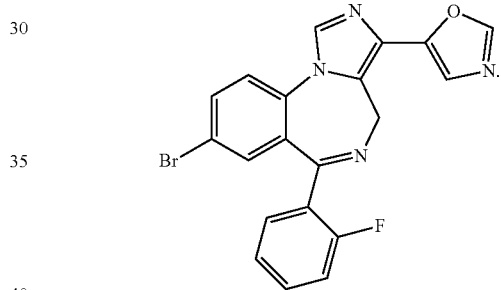

For compounds of formula (I), (II), (III), (IV), (V), and (VI), groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Compounds of formula (I), (II), (III), (IV), (V), and (VI) include compounds that differ only in the presence of one or more isotopically enriched atoms. For example, compounds may have the present structures except for the replacement of hydrogen by deuterium or tritium, or the replacement of a carbon by a $^{13}C$- or $^{14}C$-enriched carbon.

A compound of formula (I), (II), (III), (IV), (V), or (VI) can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure.

In addition to salt forms, the present invention may also provide compounds of formula (I), (II) (III), (IV), (V), or (VI) that are in a prodrug form. Prodrugs of the compounds are those compounds that readily undergo chemical changes under physiological conditions to provide the compounds. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds of formula (I), (II) (III), (IV), (V), and (VI) can be, for example, an enantiomerically enriched isomer of a stereoisomer described herein. Enantiomer, as used herein, refers to either of a pair of chemical compounds whose molecular structures have a mirror-image relationship to each other. For example, a compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

A preparation of a compound of formula (I), (II) (III), (IV), (V), or (VI) may be enriched for an isomer of the compound having a selected stereochemistry, e.g., R or S, corresponding to a selected stereocenter. For example, the compound may have a purity corresponding to a compound having a selected stereochemistry of a selected stereocenter of at least about 60%, 65%, 70%, 75%, 80%, 85%, 90%, 95%, 96%, 97%, 98%, or 99%. A compound can, for example, include a preparation of a compound disclosed herein that is enriched for a structure or structures having a selected stereochemistry, e.g., R or S, at a selected stereocenter.

In some embodiments, a preparation of a compound of formula (I), (II) (III), (IV), (V), or (VI) may be enriched for isomers (subject isomers) which are diastereomers of the compound. Diastereomer, as used herein, refers to a stereoisomer of a compound having two or more chiral centers that is not a mirror image of another stereoisomer of the same compound. For example, the compound may have a purity corresponding to a compound having a selected diastereomer of at least about 60%, 65%, 70%, 75%, 80%, 85%, 90%, 95%, 96%, 97%, 98%, or 99%.

When no specific indication is made of the configuration at a given stereocenter in a compound, any one of the configurations or a mixture of configurations is intended.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound of formula (I), (II) (III), (IV), (V), or (VI) can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Synthesis of Compounds

Compounds of formula (I), (II) (III), (IV), (V), and (VI) may be synthesized from commercially available starting materials. Exemplary syntheses are illustrated below in the Examples. The starting materials (1, 4, 9, and 14) in Schemes I, II, III, and IV have been previously synthesized ("Stereospecific anxiolytic and anticonvulsant agents with reduced muscle-relaxant, sedative-hypnotic and ataxic effects," Cook, J. M.; Zhou, H.; Huang, S.; Sarma, P.V.V.S.; Zhang, C., U.S. Patent Publication No. 2006/0003995 A1, Published Jan. 5, 2006).

Relevant references include the following:

van Leusen, A. M.; Hoogenboom, B. E.; Sideruis, H., "A novel and efficient synthesis of oxazoles from tosylmethylisocyanide and carbonyl compounds", *Tetrahedron Letters,* 13, 2369-2372, 1972;

Webb, M. R.; Donald, C.; Taylor, R. J. K., "A general route to the *Streptomyces*-derived inthomycin family: the first synthesis of (+)-inthomycin B", *Tetrahedron Letters,* 47, 549-552, 2006; and Bull, J. A.; Balskus, E. P.; Horan, R. A. J.; Langner, M.; Ley, S. V., "Total synthesis of potent antifungal marine bisoxazole natural products bengazoles A and B", *Chem. Eur. J.,* 13, 5515-5538, 2007

Other methods of synthesizing the compounds of the formulae herein will be evident to those of ordinary skill in the art. Synthetic chemistry transformations and protecting group methodologies (protection and deprotection) useful in synthesizing the compounds are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

Evaluation of Compounds

Compounds may be analyzed using a number of methods, including receptor binding studies and in vivo methods.

For example, the $GABA_A$ subunit selectivity of compounds can be evaluated, for example, using competitive binding assays. Such assays have been described (Choudhary et al. *Mol Pharmacol.* 1992, 42, 627-33; Savić et al. *Progress in Neuro-Psychopharmacology & Biological Psychiatry,* 2010, 34, 376-386). The assays involve the use of a radiolabeled compound known to bind to $GABA_A$ receptors, such as [³H]flunitrazepam. Membrane proteins can be harvested and incubated with the radiolabeled compound, and non-specific binding can be evaluated by comparing binding of the radiolabeled compound to another, non-labeled compound (e.g., diazepam). Bound radioactivity can be quantified by liquid scintillation counting. Membrane protein concentrations can be determined using commercially available assay kits (e.g., from Bio-Rad, Hercules, Calif.).

Compounds can also be evaluated in electrophysiological assays in *Xenopus* oocytes. Compounds can be preapplied to the oocytes before the addition of GABA, which can then be coapplied with the compounds until a peak response is observed. Between applications, oocytes can be washed to ensure full recovery from desensitization. For current measurements, the oocytes can be impaled with microelectrodes, and recordings performed using voltage clamps.

Compounds described herein may be $GABA_A$ receptor ligands which exhibit anxiolytic activity due to increased agonist efficacy at $GABA_A/\alpha 2$, $GABA_A/\alpha 3$, $GABA_A/\alpha_{2/3}$ and/or $GABA_A/\alpha 5$ receptors. The compounds may possess at least 2-fold, suitably at least 5-fold, and advantageously at least a 10-fold, selective efficacy for the $GABA_A/\alpha 2$, $GABA_A/\alpha 3$, and/or $GABA_A/\alpha 5$ receptors relative to the $GABA_A/\alpha 1$ receptors. However, compounds which are not selective in terms of their agonist efficacy for the $GABA_A/\alpha 2$, $GABA_A/\alpha 3$, and/or $GABA_A/\alpha 5$ receptors are also encompassed within the scope of the present invention. Such compounds will desirably exhibit functional selectivity by demonstrating anxiolytic activity with decreased sedative-hypnotic/muscle relaxant/ataxic activity due to decreased efficacy at $GABA_A/\alpha 1$ receptors.

GABAergic receptor subtype selective compounds which are ligands of the $GABA_A$ receptors acting as agonists or partial agonists are referred to hereinafter as "$GABA_A$ receptor agonists" or "$GABA_A$ receptor partial agonists" or "agonists" or "partial agonists". In particular these are compounds that are ligands of the benzodiazepine (BZ) binding site of the $GABA_A$ receptors, and hence acting as BZ site agonists or partial agonists. Such ligands also include compounds acting at the GABA site or at modulatory sites other than the benzodiazepine site of $GABA_A$ receptors.

GABAergic receptor subtype selective compounds act preferably by selectively or preferentially activating as agonists or partial agonists the $GABA_A/\alpha_2$ receptors, $GABA_A/\alpha_3$ receptors, or $GABA_A/\alpha_{2/3}$ as compared to the $GABA_A/\alpha_1$ receptors. A selective or preferential therapeutic agent has less binding affinity or efficacy to the $GABA_A/\alpha_1$ receptors compared to the $GABA_A/\alpha_2$, $GABA_A/\alpha_3$, or $GABA_A/\alpha_{2/3}$ receptors. Alternatively, the agent binds to $GABA_A/\alpha_1$, $GABA_A/\alpha_2$ and $GABA_A/\alpha_3$ receptors with a comparable affinity but exerts preferential efficacy of receptor activation at $GABA_A/\alpha_2$, $GABA_A/\alpha_3$, $GABA_A/\alpha_{2/3}$, or $GABA_A/\alpha_5$ receptors compared to the $GABA_A/\alpha_1$ receptors. A selective agent of the present invention can also have a greater or lesser ability to bind or to activate $GABA_A/\alpha_5$ receptors relative to $GABA_A/\alpha_2$ and $GABA_A/\alpha_3$ receptors. The Bz/GABA agonists act at the benzodiazepine site of the respective $GABA_A$ receptors but are not restricted to this drug binding domain in its receptor interactions.

Other methods for evaluating compounds are known to those skilled in the art. For example, an assessment of anxiolytic effects of compounds can be accomplished objectively and quantitatively with operant-based conflict procedures, as described in Fischer et al. *Neuropharmacology* 59 (2010) 612-618. Briefly, behavior which is positively reinforced can be suppressed in these procedures by response-contingent administration of a noxious stimulus such as mild electric shock. If a compound has an anxiolytic effect it increases the rates of responding that are normally suppressed by response-contingent delivery of shock. The strength of conflict procedures is their predictive validity with respect to expected therapeutic effects in humans. Results from the Fischer et al. indicate that benzodiazepine-like drugs that have pharmacological activity for $\alpha 2GABA_A$ and/or $\alpha 3GABA_A$ receptors and low receptor activity at $\alpha 1GABA_A$ and $\alpha 5GABA_A$ receptors may be useful, particularly as non-sedating anxiolytics and agents to treat neuropathic pain.

Anxiolytic activity and locomotor activity can evaluated in the light/dark box by a method developed by Crawley (*Neurosci Biobehav Rev* 1985, 9, 37-44). The light/dark box is an extremely simple noninvasive test for anxiolytic activity. Mice or rats are administered new agents 15-30 minutes prior to testing and placed in the dark portion of the light/dark box. The amount of time it takes the animals to enter the light side and how long they stay versus controls (e.g., diazepam) are a measure of anxiolytic activity. The amount of exploration (or lack thereof) can be used as a preliminary measure of sedation.

The marble burying assay (Deacon, *Nat Protocols,* 2006, 1, 122; Kinsey et al., *Pharmacol Biochem Behav* 2011, 98, 21) is another anxiolytic test. Mice or rats are pretreated the test compound 1 h before being placed in a cage filled with wood chip bedding. The rodents are then timed and the number of mables buried are counted. A reduction in marble burying compared to control is considered an anxiolytic effect.

In the elevated plus maze (Savic et al. *Pharmacol Biochem Behav* 2004, 79, 279-290), test compounds can be administrated ip 15 minutes prior to testing at which time mice can be placed in the center of the maze under a bright light condition. The number of crosses as well as the time spent in the open and closed arms of the maze for the following 15 minutes can be recorded. Control values for the percentage of entries into the open arms, percentage of time spent in the open arms, and total entries can be correlated to values obtained with controls (e.g., diazepam). Promising compounds may not suppress locomotor activity at up to 100 mg/kg and may be anxiolytic.

For evaluation of potential to treat schizophrenia, compounds may be tested using a mouse model as described in Gill et al. *Neuropsychopharmacology* 2011, 36: 1903-1911. This mouse model of schizophrenia arises from a development disturbance induced by the administration of a DNA-methylating agent, methylazoxymethanol acetate (MAM), to pregnant dams on gestational day 17. The MAM-treated offspring display structural and behavioral abnormalities, consistent with those observed in human patients with schizophrenia. Antagonism or genetic deletion of the $\alpha 5GABA_A$ receptor ($\alpha 5GABA_A$ R) leads to behaviors that resemble some of the behavioral abnormalities seen in schizophrenia, including prepulse inhibition to startle and impaired latent inhibition. The MAM model can be used to show the effectiveness of a benzodiazepine-positive allosteric modulator (PAM) compound selective for the 5 subunit of the $GABA_AR$. In Gill et al., the pathological increase in tonic dopamine transmission in the brain was reversed, and behavioral sensitivity to psychostimulants observed in MAM rats was reduced. The data suggests that such compounds would be effective in alleviating dopamine-mediated psychosis.

Compounds selective for $GABA_A$ receptor subunits can be tested for the ability to suppress seizures in several standard rat and mouse models of epilepsy, as described in U.S. Patent Application Publication No. US 2011/0261711. Anticonvulsant activity of compounds can be compared to diazepam. The standard models incorporated into anticonvulsant screening include the maximal electroshock test (MES), the subcutaneous Metrazol test (scMet), and evaluations of toxicity (TOX). The data for each condition can be presented as a ratio of either the number of animals protected or toxic (loss of locomotor activity) over the number of animals tested at a given time point and dose.

The MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on MES convulsions, 60 Hz of alternating current (50 mA in mice, 150 in rats) is delivered for by corneal electrodes which have been primed with an electrolyte solution containing an anesthetic agent (0.5% tetracaine HCL). For Test 1, mice are tested at various intervals following doses of 30, 100 and 300 mg/kg of test compound given by ip injection of a volume of 0.01 mL/g. In Test 2, rats are tested after a dose of 30 mg/kg (po) in a volume of 0.04 mL/g. Test 8 uses varying doses administered via i.p. injection, again in a volume of 0.04 mL/g. An animal is considered "protected" from MES-induced seizures upon abolition of the hindlimb tonic extensor component of the seizure (Swinyard, E. A., et al. in Antiepileptic Drugs, Levy, R. H. M., et al., Eds.; Raven Press: New York, 1989; pp 85-102; White, H. S., et al., Ital J Neurol Sci. 1995a, 16, 73-7; White, H. S., et al., in Antiepileptic Drugs, Levy, R. H. M., Meldrum, B. S., Eds.; Raven Press: New York, pp 99-110, 1995b).

Subcutaneous injection of the convulsant Metrazol produces clonic seizures in laboratory animals. The scMet test detects the ability of a test compound to raise the seizure threshold of an animal and thus protect it from exhibiting a clonic seizure. Animals can pretreated with various doses of the test compound (in a similar manner to the MES test, although a dose of 50 mg/kg (po) is the standard for Test 2 scMet). At the previously determined TPE of the test compound, the dose of Metrazol which will induce convulsions in 97% of animals ($CD_{97}$: 85 mg/kg mice) is injected into a loose fold of skin in the midline of the neck. The animals can be placed in isolation cages to minimize stress (Swinyard et al. J. Physiol. 1961, 132, 97-0.102) and observed for the next 30 minutes for the presence or absence of a seizure. An episode of clonic spasms, approximately 3-5 seconds, of the fore and/or hindlimbs, jaws, or vibrissae is taken as the endpoint. Animals which do not meet this criterion are considered protected.

To assess a compound's undesirable side effects (toxicity), animals may monitored for overt signs of impaired neurological or muscular function. In mice, the rotorod procedure (Dunham, M. S. et al. J. Amer. Pharm. Ass. Sci. Ed. 1957, 46, 208-209) is used to disclose minimal muscular or neurological impairment. When a mouse is placed on a rod that rotates at a speed of 6 rpm, the animal can maintain its equilibrium for long periods of time. The animal is considered toxic if it falls off this rotating rod three times during a 1-min period. In rats, minimal motor deficit is indicated by ataxia, which is manifested by an abnormal, uncoordinated gait. Rats used for evaluating toxicity are examined before the test drug is administered, since individual animals may have peculiarities in gait, equilibrium, placing response, etc., which might be attributed erroneously to the test substance. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone.

To further characterize the anticonvulsant activity of compounds, a hippocampus kindling screen can be performed. This screen is a useful adjunct to the traditional MES and scMet tests for identification of a substance potential utility for treating complex partial seizures.

Benzodiazepines can be highly effective drugs in certain treatment paradigms. They are routinely employed for emergency situations such as status epilepticus and other acute conditions. But their use in chronic convulsant diseases has been limited due to side effects such as sedation and with high doses respiratory depression, hypotension and other effects. Further it has long been purported that chronic administration of this class of drugs can lead to tolerance to the anticonvulsant effects. This has limited their utility as first line treatment for chronic anticonvulsant conditions. Discovery of a potent BDZ with a decreased side effect profile and efficacy over extended treatment periods would be highly desirable.

In order to assess the effects of tolerance of compounds, whether tolerance could be detected using a chronic (5 day) dose of the candidate drug can be studied. With typical benzodiazepines (for example diazepam), tolerance to the anticonvulsant effects of the drug are evident before 5 days have passed, consequently studies can be done for only 5 days. The dose to be used may be the predetermined ED50 against the scMet seizure model.

Compositions and Routes of Administration

In another aspect, the invention provides pharmaceutical compositions comprising one or more compounds of this invention in association with a pharmaceutically acceptable carrier. Such compositions may be in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that compounds may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50, or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Suitable dosage level is about 0.01 to 250 mg/kg per day, about 0.05 to 100 mg/kg per day, or about 0.05 to 5 mg/kg per day. The compounds may be administered on a regimen of 1 to 4 times per day, or on a continuous basis via, for example, the use of a transdermal patch.

Pharmaceutical compositions for enteral administration, such as nasal, buccal, rectal or, especially, oral administration, and for parenteral administration, such as intravenous, intramuscular, subcutaneous, peridural, epidural or intrathecal administration, are suitable. The pharmaceutical compositions comprise from approximately 1% to approximately 95% active ingredient, or from approximately 20% to approximately 90% active ingredient.

For parenteral administration including intracoronary, intracerebrovascular, or peripheral vascular injection/infusion preference is given to the use of solutions of the subunit selective GABAA receptor agonist, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Methods of Treatment

Compounds may be used in methods of treatment or prevention of anxiety disorders, depression, epilepsy, schizophrenia, and/or neuropathic pain.

Anxiety disorder is a term covering several different forms of a type of mental illness of abnormal and pathological fear and anxiety. Current psychiatric diagnostic criteria recognize a wide variety of anxiety disorders. Recent surveys have found that as many as 18% of Americans may be affected by one or more of them. The term anxiety covers four aspects of experiences an individual may have: mental apprehension, physical tension, physical symptoms and dissociative anxiety. Anxiety disorder is divided into generalized anxiety disorder, phobic disorder, and panic disorder; each has its own characteristics and symptoms and they require different treatment. The emotions present in anxiety disorders range from simple nervousness to bouts of terror. Standardized screening clinical questionnaires such as the Taylor Manifest Anxiety Scale or the Zung Self-Rating Anxiety Scale can be used to detect anxiety symptoms, and suggest the need for a formal diagnostic assessment of anxiety disorder.

Particular examples of anxiety disorders include generalized anxiety disorder, panic disorder, phobias such as agoraphobia, social anxiety disorder, obsessive-compulsive disorder, post-traumatic stress disorder, separation anxiety and childhood anxiety disorders.

Depression is a state of low mood and is generally caused by genetic, psychological and social factors. Depression can leave those affected feeling down and unable to enjoy activities. Approximately 4.3% of the world population suffers from depression, while lifetime prevalence ranges from 8-12%. Particular examples of depression are major depressive disorder, persistent depressive disorder and bipolar disorder, which itself has extreme lows as a characteristic.

Epilepsy is a common chronic neurological disorder that is characterized by recurrent unprovoked seizures. These seizures are transient signs and/or symptoms due to abnormal, excessive or synchronous neuronal activity in the brain. There are many different epilepsy syndromes, each presenting with its own unique combination of seizure type, typical age of onset, EEG findings, treatment, and prognosis. Exemplary epilepsy syndromes include, e.g., Benign centrotemporal lobe epilepsy of childhood, Benign occipital epilepsy of childhood (BOEC), Autosomal dominant nocturnal frontal lobe epilepsy (ADNFLE), Primary reading epilepsy, Childhood absence epilepsy (CEA), Juvenile absence epilepsy, Juvenile myoclonic epilepsy (JME), Symptomatic localization-related epilepsies, Temporal lobe epilepsy (TLE), Frontal lobe epilepsy, Rasmussen's encephalitis, West syndrome, Dravet's syndrome, Progressive myoclonic epilepsies, and Lennox-Gastaut syndrome (LGS). Genetic, congenital, and developmental conditions are often associated with epilepsy among younger patients. Tumors might be a cause for patients over age 40. Head trauma and central nervous system infections may cause epilepsy at any age.

Schizophrenia is a mental disorder characterized by a breakdown of thought processes and by poor emotional responsiveness. It most commonly manifests itself as auditory hallucinations, paranoid or bizarre delusions, or disorganized speech and thinking, and it is accompanied by significant social or occupational dysfunction. The onset of symptoms typically occurs in young adulthood, with a global lifetime prevalence of about 0.3-0.7%. Diagnosis is based on observed behavior and the patient's reported experiences. Genetics, early environment, neurobiology, and psychological and social processes appear to be important contributory factors. Current research is focused on the role of neurobiology, although no single isolated organic cause has been found. Particular types of schizophrenia include paranoid type, disorganized type, catatonic type, undifferentiated type, residual type, post-schizophrenic depression and simple schizophrenia.

Neuropathic pain encompasses a range of painful conditions of diverse origins including diabetic neuropathy, post-herpetic neuralgia and nerve injuries after surgery. It includes pain following paraplegia, hypersensitivity to non-painful stimuli (allodynia), for example after surgery or during migraine attacks, spontaneous pain, hyperalgesia and diffuse muscle tenderness of myofacial syndromes. Back pain, cancer pain and AIDS associated pain also qualify as neuropathic pain. Currently prescribed drugs for neuropathic pain are often addictive, are not effective for all patients and have various side effects including tolerance, addiction, sedation, liver toxicity. The financial burden from the loss of productivity in the US alone numbers in the billions of dollars notwithstanding the misery these patients suffer.

In another aspect, the invention provides a method of treating a disorder selected from an anxiety disorder, depression, epilepsy, schizophrenia and neuropathic pain, in a subject in need of treatment, comprising administering to the subject an effective amount of a compound of In an aspect, the invention provides a method of treating an anxiety disorder in a subject in need of treatment, comprising administering to the subject an effective amount of a compound of formula (I), (II) (III), (IV), (V), or (VI). In embodiments, the anxiety disorder is selected from the group consisting of generalized anxiety disorder, panic disorder, phobias such as agoraphobia, social anxiety disorder, obsessive-compulsive disorder, post-traumatic stress disorder, separation anxiety and childhood anxiety disorders.

In an aspect, the invention provides a method of treating depression in a subject in need of treatment, comprising administering to the subject an effective amount of a compound of formula (I), (II) (III), (IV), (V), or (VI).

In an aspect, the invention provides a method of treating schizophrenia in a subject in need of treatment, comprising administering to the subject an effective amount of a compound of formula (I), (II) (III), (IV), (V), or (VI). In embodiments, the schizophrenia may be selected from the group consisting of paranoid type, disorganized type, catatonic type, undifferentiated type, residual type, post-schizophrenic depression and simple schizophrenia.

In an aspect, the invention provides a method of treating epilepsy in a subject in need of treatment, comprising administering to the subject an effective amount of a compound of formula (I), (II) (III), (IV), (V), or (VI). In another aspect, the invention provides a method of treating seizures in a subject in need of treatment, comprising administering to the subject an effective amount of a compound of formula (I), (II) (III), (IV), (V), or (VI).

In an aspect, the invention provides a method of treating neuropathic pain in a subject in need of treatment, comprising administering to the subject an effective amount of a compound of formula (I), (II) (III), (IV), (V), or (VI).

The following non-limiting examples are intended to be purely illustrative of some aspects and embodiments, and show specific experiments that were carried out in accordance with the disclosure.

EXAMPLES

Example 1

Compound Syntheses

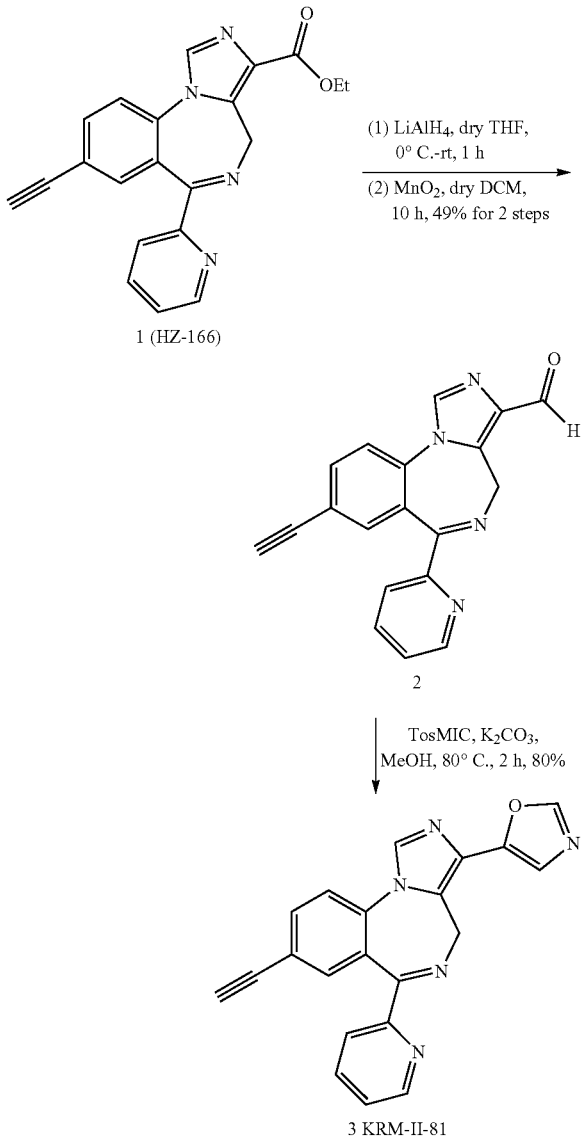

8-Ethynyl-6-(pyridin-2-yl)-4H-benzo[f]imidazo[1,5-a][1,4]diazepine-3-carbaldehyde (2)

The ethyl ester of 2'-pyridylbenzimidazodiazepine 1 (1.5 g, 4.21 mmol) was placed in an oven dried two neck round bottom flask and was then dissolved in dry THF. The reaction mixture was stirred at 0° C. and LiAlH$_4$ (320 mg, 8.42 mmol) was added to the reaction mixture at 0° C. After 10 min the reaction mixture was stirred at rt for up to 45 min under an argon atmosphere. After 45 min at rt analysis of the mixture by TLC (silica gel 1: 9 MeOH/EtOAc) indicated the absence of starting ester 1. The reaction mixture was slowly quenched with an aq saturated sodium sulfate solution (20 mL) at 0° C. and then the reaction mixture was diluted with ethyl acetate (50 mL). After this the mixture was filtered through a small bed of Celite. Water was added to the filtrate and it was extracted with ethyl acetate (3×30 mL). The combined organic layers were washed with water and brine successively and dried (Na$_2$SO$_4$). After this the solvent was removed under reduced pressure to furnish the mixture of alcohols (imine alcohol 40% and reduced imine alcohol 60%, via analysis by H$^1$NMR spectroscopy) as a yellow solid. This mixture of alcohols was used directly in the next step. The mixture of 2'-pyridylalcohols (4.45 g, 4.61 mmol) were dissolved in dry DCM (60 mL) under an argon atmosphere, and activated MnO$_2$ (4.01 g, 46.10 mmol) and Na$_2$CO$_3$ were added to the reaction mixture at 0° C. The mixture was stirred at room temperature for 12 hours. After completion of the reaction as indicated by TLC (complete conversion of alcohol to aldehyde), the reaction mixture was diluted with DCM (50 mL) and it was filtered through a small pad of Celite. The solvent was removed under reduced pressure to get the crude 2'-pyridyl aldehyde along with some other byproducts by TLC (1:9 MeOH/EtOAc). This material was purified by flash column chromatography using EtOAc/DCM (2:1 and 1 mL MeOH+1 mL TEA for 100 mL) to afford the pure 2' pyridyl aldehyde 2 as a white solid (650 mg, 49.2% over two steps); mp: 238-240° C.; $^1$H NMR (500 MHz, CDCl$_3$) δ 10.05 (s, 1H), 8.56 (d, J=5.0 Hz, 1H), 8.08 (d, J=7.5 Hz, 1H), 7.97 (s, 1H), 7.78 (ddd, J=1.5, 6.0 Hz, 1H), 7.77 (dd, J=1.5, 7.0 Hz, 1H), 7.55-7.57 (m, 2H), 7.38 (ddd, J=1.5, 5.0 Hz, 1H), 6.00 (br s, 1H), 4.17 (br s, 1H), 3.16 (s, 1H): $^{13}$C NMR (75 MHz, CDCl$_3$) δ 186.9, 167.7, 156.2, 148.6, 137.7, 137.1, 136.7, 136.3, 135.4, 135.3, 135.0, 127.1, 124.9, 124.0, 122.8, 121.5, 81.5, 79.7, 44.4. (ESI) MS: m/z 313 (M+H)$^+$.

5-(8-Ethynyl-6-(pyridin-2-yl)-4H-benzo[f]imidazo[1,5-a][1,4]diazepin-3-yl)oxazole (3, KRM-II-81)

The toluenesulfonylmethyl isocyanide (TosMIC, 640 mg, 3.30 mmol) was placed in a dry two neck round bottom flask and dissolved in dry MeOH (50 mL) under an argon atmosphere. At room temperature, K$_2$CO$_3$ (1.30 g, 9.99 mmol) was added as well as 2' pyridyldiazepine carboxaldehyde 2 (650 mg, 2.08 mmol) to the reaction mixture and it was heated to reflux for 3 to 4 h. After completion of the reaction on analysis by TLC (silica gel, 1:10 MeOH and EtOAc) which indicated the absence of aldehyde starting material and complete conversion into an oxazole of lower R$_f$. The reaction mixture was then quenched with cold water. After this, ⅓ of the solvent was removed under reduced pressure and the work up followed with ethyl acetate (3×30 mL). The combined organic layers were washed with water and brine successively and dried (Na$_2$SO$_4$). The solvent was then removed under reduced pressure and the residue was purified by silica gel flash chromatography to give the pure 2' pyridyldiazepine oxazole as a white solid (510 mg, 72%); mp: 220-222° C. $^1$H NMR (300 MHz, CDCl$_3$) δ 8.62 (d, J=4.2 Hz, 1H), 8.12 (s, 1H), 8.06 (d, J=7.8 Hz, 1H), 7.96 (s, 1H), 7.85 (ddd, J=1.8, 6.0 Hz, 1H), 7.79 (dd, J=1.8, 6.6 Hz, 1H), 7.62 (d, J=8.4 Hz, 1H), 7.55 (d, J=1.5 Hz, 1H), 7.53 (s, 1H), 7.41 (ddd, J=1.5, 4.8 Hz, 1H), 5.78 (d, J=12.9 Hz, 1H), 4.31 (d, J=12.9 Hz, 1H). $^{13}$C NMR (75 MHz, CDCl$_3$) δ 167.9, 156.7, 149.9, 149.0, 146.6, 137.0, 136.4, 135.8, 135.5, 135.3, 129.8, 127.5, 127.0, 124.9, 124.0, 122.8, 122.7, 121.0, 81.8,7, 79.5, 45.3; HRMS (ESI m/z) for C$_{21}$H$_{13}$N$_5$O calcd 352.1188, found 352.1193 (M+H)$^+$.

Scheme II. Synthesis of KRM-II-18B (8).

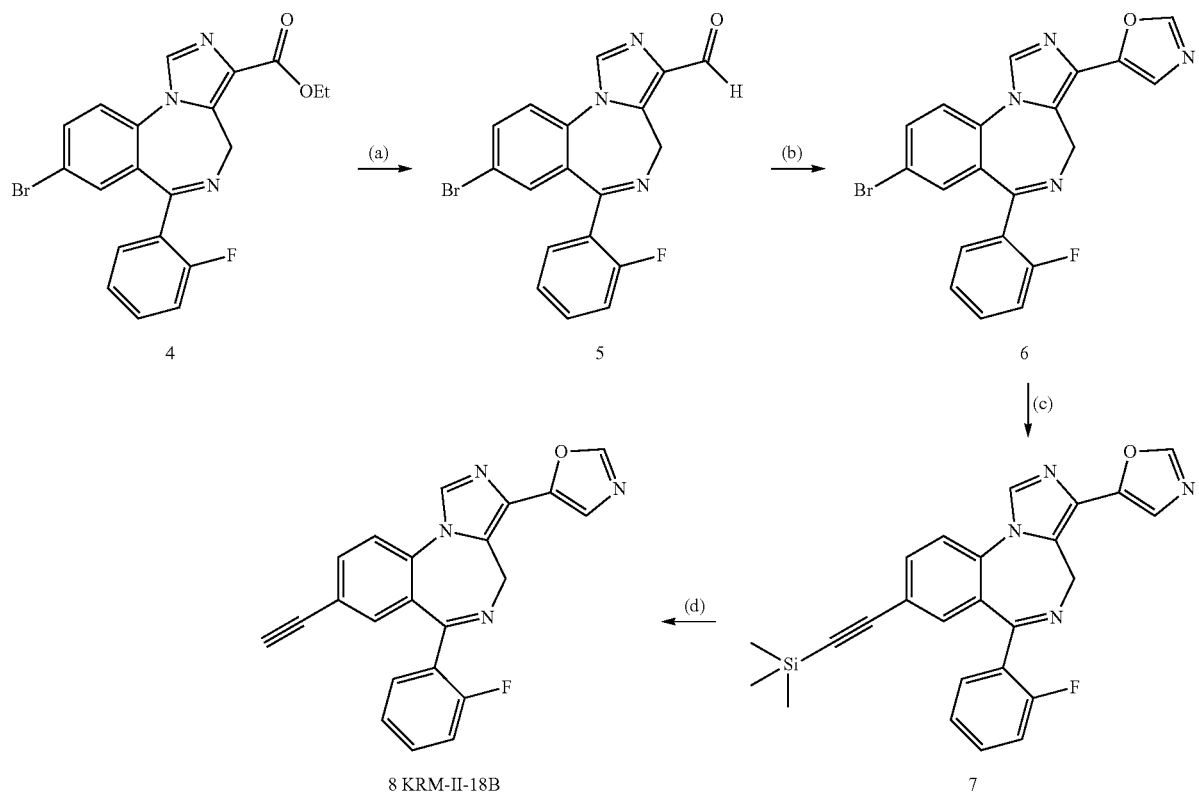

Reagents and conditions: (a) DIBAL-H, -78° C. 2 h, 75%, (b) TosMIC, K$_2$CO$_3$, MeOH, 80° C., 2 h, 77%,
(c) TMS acetylene, Pd(OAc)$_2$ (PPh$_3$)$_2$, TEA/CH$_3$CN, rf, 10 h, 92%, (d) TBAF xH$_2$O, THF, 0° C.-rt, 1 h, 88%,

8-Bromo-6-(2-fluorophenyl)-4H-benzo[f]imidazo[1,5-a][1,4]diazepine-3-carbaldehyde (5)

A solution of diisobutylaluminumhydride (6.25 mL of 1.2 M solution in toluene, 20% w/v) was added dropwise to a vigorously stirred solution of the ester 4 (1.5 g, 3.51 mmol) in anhydrous dichloromethane (40 mL) under an argon atmosphere at −78° C. (dry ice-ethyl acetate). After this, the reaction mixture was stirred for an additional 2-3 h at −78° C., and was monitored by TLC every 30 min after 1 h. The temperature must not get above −78° C. If the temperature gets above −78° C. or if the reaction continues more than 3 h at −78° C. other byproducts are formed (imine reduced aldehyde and ester to alcohol). After completion of the reaction, excess DIBAL-H was quenched by careful addition of dry methanol (5 mL), followed by 5% aq HCl (10 mL). After this the resulting mixture was allowed to warm to room temperature. If the reaction mixture formed an aluminum-related emulsion, a saturated aq solution of Rochelle's salt and DCM (50 mL) were added to the reaction mixture. It was then filtered through a small pad of Celite and then the organic layer was separated. The aq layer which remained was extracted with DCM (2×30 mL). The combined organic layers were washed with brine and dried ($Na_2SO_4$). The solvent was removed under reduced pressure to afford the crude aldehyde. This residue was purified by flash chromatography (2:1 ethyl acetate/hexane) to afford the pure diazepine aldehyde 5 as a white solid (1.0 g, 74.6%); mp 120-122° C.; $^1$H NMR (300 MHz, $CDCl_3$) δ 10.07 (s, 1H), 8.01 (s, 1H), 7.80 (dd, J=1.8, 6.6 Hz, 1H), 7.67 (ddd, J=1.5, 6.0 Hz, 1H), 7.45-7.52 (m, 3H), 7.25-7.30 (m, 1H), 7.04 (t, J=9.3 Hz, 1H), 6.02 (br s, 1H), 4.15 (br s, 1H). LCMS: m/z 385 (M+H).

General Synthetic Procedure for Oxazole Containing benzimidazodiazepines.

5-(8-Bromo-6-(2-fluorophenyl)-4H-benzo[f]imidazo[1,5-a][1,4]diazepin-3-yl)oxazole (6)

The toluenesulfonylmethyl isocyanide (TOSMIC, 300 mg, 1.56 mmol) was placed in a dry two neck round bottom flask and dissolved in dry MeOH (30 mL) under an argon atmosphere. At room temperature, $K_2CO_3$ (649 mg, 1.53 mmol) was added as well as the 2'fluoro diazepine carboxaldehyde 5 (647 mg, 1.62 mmol) to the reaction mixture and it was heated to reflux for 3 to 4 h. After completion of the reaction on analysis by TLC (silica gel, 2:1 EtOAc and hexane), which indicated the absence of aldehyde starting material and complete conversion to the oxazole of lower $R_f$, the reaction mixture was then quenched with cold water. After this, ⅓ of the solvent was removed under reduced pressure and the work up followed with ethyl acetate (3×40 mL). The combined organic layers were washed with water, brine successively and dried ($Na_2SO_4$). The solvent was then removed under reduced pressure and the residue was purified by silica gel flash chromatography to give the pure 2' 2'fluorodiazepine oxazole 6 as white solid (550 mg, 76.7% yield); mp: 190-192° C.; $^1$H NMR (300 MHz, $CDCl_3$) δ 8.01 (s, 1H), 7.92 (s, 1H), 7.77 (dd, J=2.1, 6.6 Hz, 1H), 7.77 (ddd, J=1.5, 6.0 Hz, 1H), 7.52 (s, 1H), 7.46-7.52 (m, 3H), 7.23-7.28 (m, 1H), 7.04 (t, J=8.4 Hz, 1H), 5.75 (br s, 1H), 4.26 (br s, 1H). $^{13}$C NMR (300 MHz, $CDCl_3$) δ 165.0, 161.8, 158.5, 149.8, 146.5, 135.1, 134.9, 133.6, 133.3, 132.5, 131.1, 130.4, 129.7, 127.6, 124.6, 124.0, 122.6, 120.9, 116.4, 116.1, 45.3; HRMS (ESI-TOF m/z) for $C_{20}H_{12}N_4OFBr$ calcd 423.0263, found 423.0251 (M+H)$^+$.

5-(6-(2-Fluorophenyl)-8-((trimethylsilyl)ethynyl)-4H-benzo[f]imidazo[1,5-a][1,4]diazepin-3-yl)oxazole (7)

The 2'fluorodiazepine diazepine bromide 6 (100 mg, 0.23 mmol) and bis(triphenylphosphine)-palladium (II) acetate (10 mg, 0.011 mmol) were added to an oven dried two neck round bottom flask, after which the round bottom flask was fitted with a rubber septum. It was then evacuated under vacuum and back filled with argon. After this, a mixed dry solvent system of $CH_3CN$:TEA (1:2 ratio) and trimethylsilylacetylene (0.04 mL, 0.26 mmol) were added to the round bottom flask with a syringe under a positive pressure of argon. The round bottom flask was fitted with a reflex condenser and the reaction mixture was degassed under vacuum and argon, the process was repeated three times, after which the reaction mixture was slowly heated to 90° C. After stirring for 10 h, the reaction mixture was diluted with ethyl acetate and filtered through a bed of Celite. The organic layer was washed with brine and dried ($Na_2SO_4$). The solvent was then removed under reduced pressure to furnish a crude solid. This material was purified by flash chromatography (3:1 ethyl acetate/hexane) to afford the pure trimethylsilylacetylene 2'fluorodiazepine intermediate as a light brown solid 7 (90 mg, 92.6% yield). $^1$H NMR (300 MHz, $CDCl_3$) δ 8.02 (s, 1H), 7.92 (s, 1H), 7.60-7.74 (m, 3H), 7.40-7.57 (m, 3H), 7.23-7.28 (m, 1H), 7.04 (t, J=9.0 Hz, 1H), 5.73 (br s, 1H), 4.24 (br s, 1H), 0.24 (s, 9H); HRMS (ESI-TOF m/z) for $C_{25}H_{21}N_4OFSi$ calcd 441.1543, found 441.1541 (M+H)$^+$.

5-(8-Ethynyl-6-(2-fluorophenyl)-4H-benzo[f]imidazo[1,5-a][1,4]diazepin-3-yl)oxazole KRM-II-18B (8)

A solution of 2'-fluorodiazepine trimethylsilylacetylene 7 (90 mg, 0.20 mmol) was dissolved in dry THF and kept at 0° C. after which tetrabutylammonium iodide (0.05 mL, 024 mmol) was added slowly to the reaction mixture at 0° C. After 10 min the reaction mixture was stirred at room temperature for 2 h under an argon atmosphere. After TLC (silica gel) indicated the absence of starting material, this reaction mixture was quenched by slow addition of ice cold water and the combined layers were extracted with ethyl acetate (3×20 mL). The combined organic layers were washed with water and brine. This solution was dried ($Na_2SO_4$) and the solvent was removed under reduced pressure to furnish a solid. This material was then purified by flash chromatography (4:1 ethyl acetate/hexane) to afford the pure 8-acetyleno-2'-fluorodiazepine oxazole 8 as a white solid (80 mg, 88% yield); mp 212-214; $^1$H NMR (300 MHz, $CDCl_3$) δ 8.03 (s, 1H), 7.93 (s, 1H), 7.75 (d, J=7.8 Hz, 1H), 7.57-7.63 (m, 2H), 7.44-7.53 (m, 3H), 7.23-7.28 (m, 1H), 7.04 (t, J=9.0 Hz, 1H), 5.74 (br s, 1H), 4.26 (br s, 1H), 3.16 (s, 1H). $^{13}$C NMR (300 MHz, $CDCl_3$) δ 165.5, 161.9, 158.5, 149.8, 146.5, 135.4, 135.0, 134.3, 132.3, 131.1, 129.8, 128.9, 127.8, 127.5, 124.5, 122.6, 121.6, 116.4, 116.1, 81.4, 79.6, 45.0; HRMS (ESI-TOF m/z) for $C_{22}H_{13}N_4OF$ calcd 369.1144, found 369.1146 (M+H)$^+$.

Scheme III. Synthesis of KRM-II-82

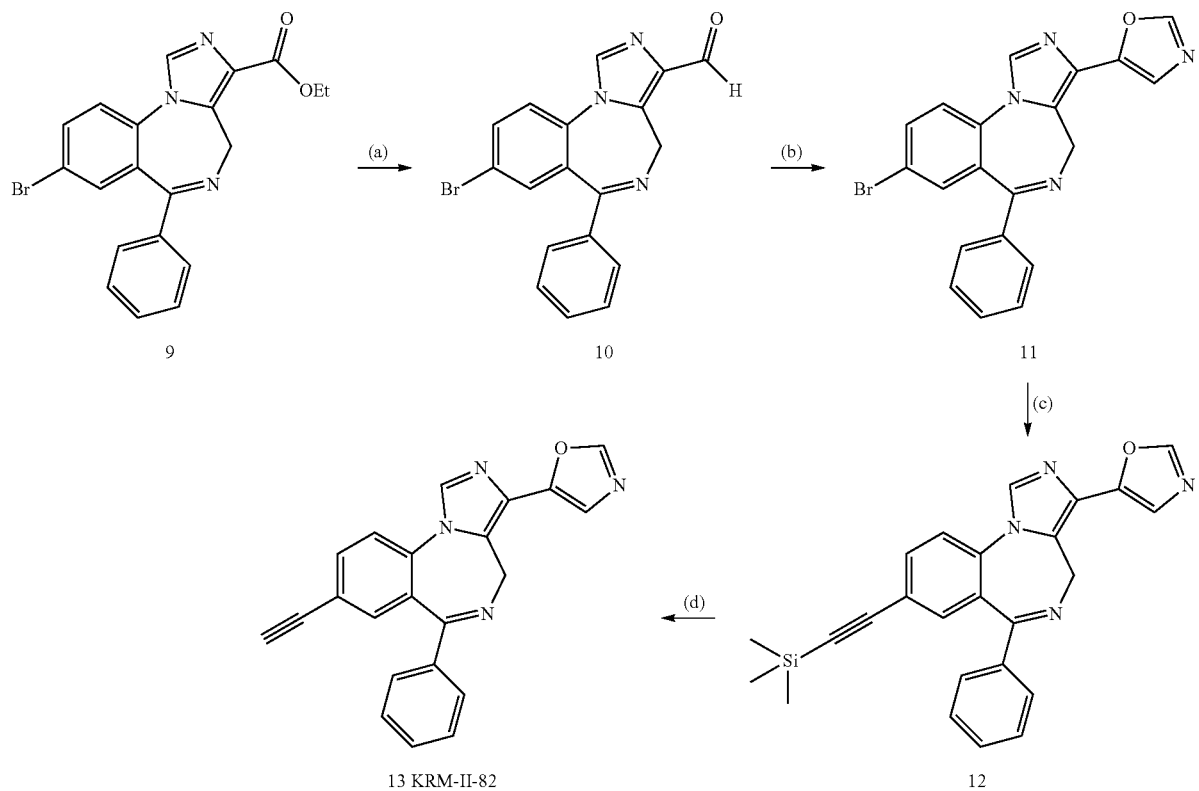

13 KRM-II-82

Reagents and conditions: (a) DIBAL-H, −78° C. 2 h, 76%, (b) TosMIC, K₂CO₃, MeOH, 80° C., 2 h, 78%, (c) TMS acetylene, Pd(OAc)₂ (PPh₃)₂, TEA/CH₃CN, rf, 10 h, 84%, (d) TBAF xH₂O, THF, 0° C.-rt, 1 h, 90%,

8-Bromo-6-phenyl-4H-benzo[f]imidazo[1,5-a][1,4]diazepine-3-carbaldehyde (10)

A solution of diisobutylaluminumhydride (8.5 mL of 1.2 M solution in toluene, 20% w/v) was added dropwise to a vigorously stirred solution of the ester 9 (2.7 g, 6.58 mmol) in anhydrous dichloromethane (50 mL) under an argon atmosphere at −78° C. (dry ice-ethyl acetate). After this the reaction mixture was stirred for an additional 2-3 h at −78° C., and was monitored by TLC every 30 min after 1 h. The temperature must not get above −78° C. If the temperature gets above −78° C. or if the reaction continues more than 3 h at −78° C. other byproducts are formed (imine reduced aldehyde and ester to alcohol). After completion of the reaction, excess DIBAL-H was quenched by careful addition of dry methanol (5 mL), followed by 5% aq HCl (10 mL). After this the resulting mixture was allowed to warm rt. If the reaction mixture forms an aluminum-related emulsion, a saturated aq solution of Rochelle's salt and DCM (50 mL) were added to the reaction mixture. It was then filtered through a small pad of Celite and then the organic layer was separated. The aq layer which remained was extracted with DCM (2×30 mL). The combined organic layers were washed with brine and dried (Na₂SO₄). The solvent was removed under reduced pressure to afford the crude aldehyde. This residue was purified by flash chromatography (2:1 ethyl acetate/hexane) to afford the pure diazepine aldehyde 10 as a white solid (2.0 g, 76%); mp 192-194° C.; $^1$H NMR (300 MHz, CDCl₃) δ 10.06 (s, 1H), 8.01 (s, 1H), 7.84 (d, J=8.4 Hz, 1H), 7.62 (s, 1H), 7.47-7.54 (m, 4H), 7.39-7.44 (m, 2H), 5.98 (d, J=12.6 Hz, 1H), 4.02 (d, J=12.3 Hz, 1H). LCMS: m/z 367 (M+2).

5-(8-Bromo-6-phenyl-4H-benzo[f]imidazo[1,5-a][1,4]diazepin-3-yl)oxazole (11)

The reaction was performed following the same procedure for 6 employing TosMIC (350 mg, 1.79 mmol), K₂CO₃ (7.4 g, 6.90 mmol) and diazepine aldehyde 10 (720 mg, 2.30 mmol). This afforded the crude compound which was purified by flash silica gel chromatography (4:1 ethyl acetate/hexane) to give a white solid 11 (601 mg, 78.0% yield): mp 225-227° C.; $^1$H NMR (300 MHz, CDCl₃) δ 8.05 (s, 1H), 7.92 (s, 1H), 7.81 (dd, J=1.8, 6.6 Hz, 1H), 7.82 (d, J=8.4 Hz, 1H), 7.53-7.57 (m, 3H), 7.43-7.49 (m, 2H), 7.39-7.43 (m, 2H), 5.75 (d, J=12.6 Hz, 1H), 4.24 (d, J=12.6 Hz, 1H). $^{13}$C NMR (300 MHz, CDCl₃) δ 167.9, 156.7, 149.9, 148.9, 146.6, 137.0, 136.4, 135.8, 135.4, 135.3, 129.8, 127.5, 127.0, 124.9, 124.0, 122.8, 122.6, 121.0, 45.3; HRMS (ESI-TOF m/z) for C₂₀H₁₃N₄OBr calcd 405.0349, found 405.0345 (M+H)⁺.

5-(6-Phenyl-8-((trimethylsilyl)ethynyl)-4H-benzo[f]imidazo[1,5-a][1,4]diazepin-3-yl)oxazole (12)

The trimethylsilylacetylenodiazepine 12 was prepared according to the method described for 7, employing the bromodiazepine oxazole 11 (700 mg, 1.72 mmol), bis(triphenylphosphine)palladium(II)acetate (64 mg, 0.0864 mmol) and trimethylsilyl acetylene (0.3 mL, 2.07 mmol).

The residue which resulted was purified by silica gel flash column chromatography (3:1 ethyl acetate/hexane) to give a light yellow solid 12 (650 mg, 89.6% yield); mp 107-109° C.; $^1$H NMR (300 MHz, CDCl$_3$) δ 8.05 (s, 1H), 7.92 (s, 1H), 7.81 (dd, J=1.8, 6.6 Hz, 1H), 7.82 (d, J=8.4 Hz, 1H), 7.53-7.57 (m, 3H), 7.43-7.49 (m, 2H), 7.39-7.43 (m, 2H), 5.75 (d, J=12.6 Hz, 1H), 4.24 (d, J=12.6 Hz, 1H), 0.25 (s, 9H); HRMS (ESI-TOF m/z) for C$_{25}$H$_{22}$N$_4$OSi calcd 423.1638, found 423.1636 (M+H)$^+$.

5-(8-Ethynyl-6-phenyl-4H-benzo[f]imidazo[1,5-a][1,4]diazepin-3-yl)oxazole KRM-II-82 (13)

The acetylenodiazepine oxazole 13 was prepared, according to the method described for 8, which employed the TMS-acetylenodiazepine oxazole 12 (500 mg, 1.18) and TBAF (0.5 mL, 1.76 mmol). After workup, the residue was purified by silica gel flash column chromatography (4:1 ethyl acetate/hexane) to afford acetylenodiazepine oxazole 13 as a white solid (370 mg, 90% yield); mp 120-122° C. $^1$H NMR (300 MHz, CDCl$_3$) δ 8.08 (s, 1H), 7.93 (s, 1H), 7.81 (dd, J=1.8, 6.6 Hz, 1H), 7.81 (d, J=8.4 Hz, 1H), 7.53-7.57 (m, 3H), 7.43-7.49 (m, 2H), 7.39-7.43 (m, 2H), 5.75 (d, J=12.9 Hz, 1H), 4.24 (d, J=12.9 Hz, 1H), 3.18 (s, 1H). $^{13}$C NMR (300 MHz, CDCl$_3$) δ 167.9, 156.7, 149.9, 148.9, 146.6, 137.0, 136.4, 135.8, 135.4, 135.3, 129.8, 127.5, 127.0, 124.9, 124.0, 122.8, 122.6, 121.0, 81.8, 79.5, 45.2; HRMS (ESI-TOF m/z) for C$_{22}$H$_{14}$N$_4$O calcd 351.1246, found 351.1240 (M+H)$^+$.

8-Bromo-6-(pyridin-2-yl)-4H-benzo[f]imidazo[1,5-a][1,4]diazepine-3-carboxaldehyde (15)

The ethyl ester of 2'-pyridylbenzimidazodiazepine 14 (500 mg, 1.22 mmol) was placed in an oven dried two neck round bottom flask and was then dissolved in dry THF. The reaction mixture was stirred at 0° C. and LiAlH$_4$ (93 mg, 2.43 mmol) was added to the reaction mixture at 0° C. After 10 min the reaction mixture was stirred at rt up to 45 min under an argon atmosphere. After 45 min at rt analysis of the mixture by TLC (silica gel 1: 9 MeOH/EtOAc) indicated the absence of starting ester 14. The reaction mixture was slowly quenched with a saturated aq solution of sodium sulfate (10 mL) at 0° C. and then the reaction mixture was diluted with ethyl acetate (30 mL). After this the mixture was filtered through a small pad of Celite and then the filtrate was extracted with ethyl acetate (3×30 mL). The combined organic layers were washed with water and brine successively. After this, the solvent was removed under reduced pressure to furnish the mixture of alcohols (imine alcohol 60% and reduced imine alcohol 40%, via analysis by H$^1$NMR spectroscopy) as a yellow solid. This mixture of alcohols was used directly in the next step. The mixture of 2'-pyridylalcohols (455 mg, 1.22 mmol) were dissolved in dry DCM (30 mL) under an argon atmosphere, and activated MnO$_2$ (278 mg, 14.4 mmol) was added to the reaction mixture at 0° C. The mixture was stirred at rt overnight. After completion of the reaction as indicated by TLC Scheme IV. Alternate Synthetic Route to KRM-II-81 (3).

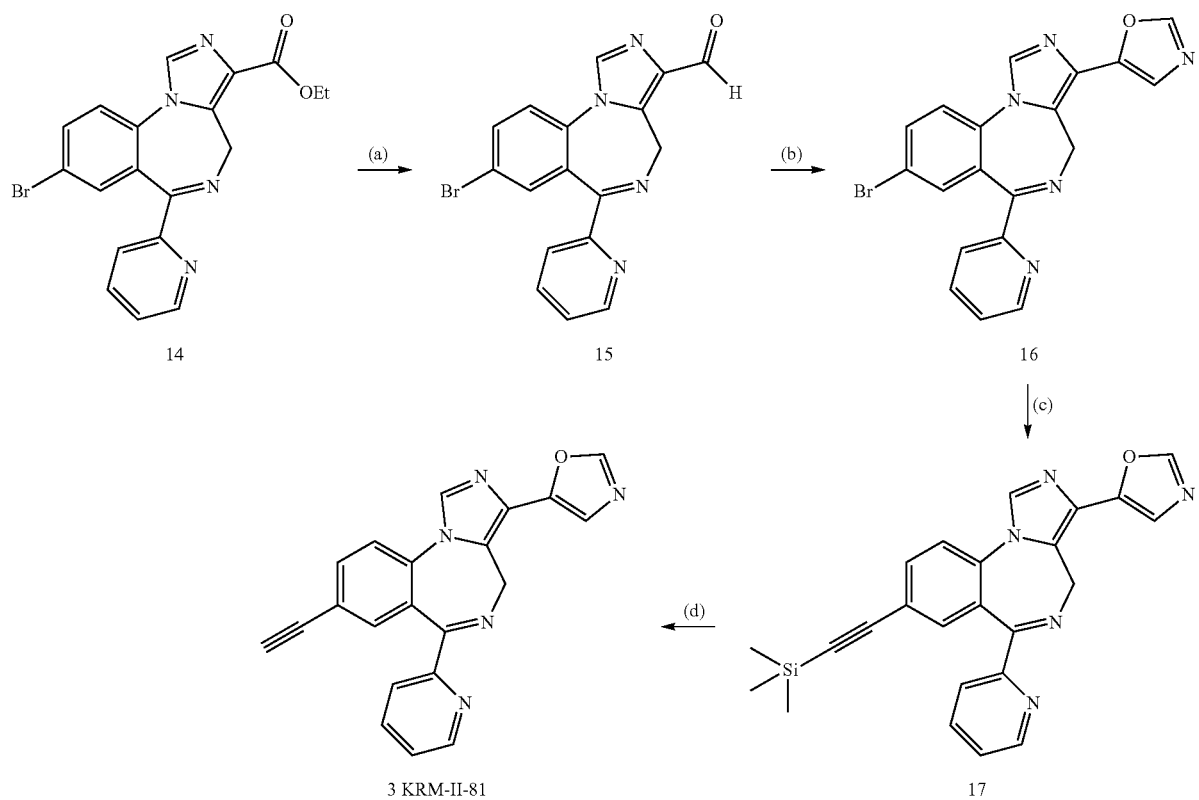

Reagents and conditions: (a) (i) LiAlH$_4$, dry THF, 0° C.-rt, 1 h, (ii) MnO$_2$, dry CH$_2$Cl$_2$, 57% over 2 steps)
(b) TosMIC, K$_2$CO$_3$, MeOH, 80° C., 2 h, 73%, (c) TMS acetylene, Pd(OAc)$_2$ (PPh$_3$)$_2$, TEA/CH$_3$CN, rf, 10 h, 80%,
(d) TBAF xH$_2$O, THF, 0° C.-rt, 1 h, 82%, (complete conversion of alcohol to aldehyde), the reaction mixture was diluted with DCM/EtOAc (30 mL) and was filtered through a small pad of Celite. The solvent was removed under reduced pressure to get the crude 2'-pyridyl aldehyde along with some other byproducts by TLC (1:9 MeOH/EtOAc). This material was purified by flash column chromatography using EtOAc/DCM (2:1 and 1 mL MeOH+1 mLTEA for 100 mL) to afford the pure 2' pyridyl aldehyde 15 as a white solid (289 mg, 56.7% over two steps); mp: 220-222° C. $^1$H NMR (300 MHz, CDCl$_3$) δ 10.07 (s, 1H), 8.56 (d, J=2.4 Hz, 1H), 8.13 (d, J=7.8 Hz, 1H), 7.96 (s, 1H), 7.80-7.86 (m, 2H), 7.62 (s, 1H), 7.49 (d, J=8.4 Hz, 1H), 7.40 (t, J=7.2 Hz, 1H), 6.10 (br s, 1H), 4.15 (br s, 1H). LCMS: m/z 368 (M+2)$^+$.

5-(8-Bromo-6-(pyridin-2-yl)-4H-benzo[f]imidazo[1, 5-a][1,4]diazepin-3-yl)oxazole (16)

The 2' pyridyldiazepine oxazole 16 was prepared according to the method described for 6 employing TosMIC (160 mg, 0.81 mmol), K$_2$CO$_3$ (223 mg, 18.46 mmol) and 2' pyridyldiazepine carboxaldehyde 15 (200 mg, 1.62 mmol). This afforded the crude oxazole which was purified by flash silica gel chromatography (silica gel, 1:10 MeOH and EtOAc) to give pure 2' pyridyldiazepine oxazole 16 as a white solid (160 mg, 73%); mp: 226-228° C.; $^1$H NMR (500 MHz, CDCl$_3$) δ 8.62 (d, J=4.5 Hz, 1H), 8.24 (s, 1H), 8.08 (d, J=8.0 Hz, 1H), 7.96 (s, 1H), 7.82-7.87 (m, 2H), 7.57-7.59 (m, 2H), 7.40-7.43 (m, 1H), 5.78 (d, J=12.5 Hz, 1H), 4.32 (d, J=12.5 Hz, 1H), (ESI) MS: m/z 368 (M+H)$^+$.)$^+$. $^{13}$C NMR (300 MHz, CDCl$_3$) δ 167.2, 155.9, 150.1, 148.7, 145.4, 137.2, 135.3, 135.2, 134.4, 133.3, 129.6, 128.3, 126.9, 125.1, 124.5, 124.1, 123.4, 120.8, 44.9; HRMS (ESI-TOF m/z) for C$_{19}$H$_{12}$N$_5$OBr calcd 406.0299, found 406.0298 (M+H)$^+$.

5-(6-(Pyridin-2-yl)-8-((trimethylsilyl)ethynyl)-4H-benzo[f]imidazo[1,5-a][1,4]diazepin-3-yl)oxazole (17)

The 2'pyridyltrimethylsilylacetylenodiazepine 17 was prepared, according to the method described for 7, which employed the 2' pyridyldiazepine bromide 16 (160 mg, 0.394 mmol) bis(triphenylphosphine)palladium(II)acetate (15.0 mg, 0.02 mmol) and trimethylsilyl acetylene (0.3 mL, 2.07 mmol). After work up, the residue which resulted was purified by silica gel flash column chromatography (4:1 ethyl acetate/DCM and 1 mL MeOH and 1 mL TEA for 100 mL) to give a light brown solid 17 (133 mg, 80%). $^1$H NMR (300 MHz, CDCl$_3$) δ 8.63 (d, J =4.1 Hz, 1H), 8.26 (s, 1H), 8.06 (d, J=8.0 Hz, 1H), 7.97 (s, 1H), 7.82-7.88 (m, 2H), 7.57-7.59 (m, 2H), 7.40-7.43 (m, 1H), 5.78 (d, J=12.1 Hz, 1H), 4.32 (d, J=12.1 Hz, 1H), 0.24 (s, 9H).

5-(8-Ethynyl-6-(pyridin-2-yl)-4H-benzo[f]imidazo[1,5-a][1,4]diazepin-3-yl)oxazole KRM-II-81 (3)

The 2'-pyridyl-8-acetylenediazepines oxazole 3 was prepared, according to the method described for 8, employing the 2'-pyridyltrimethylsilylacetylene diazepine 17 (600 mg, 1.4 mmol), and TBAF (0.48 mL, 1.7 mmol). After workup the residue was purified by flash chromatography (4:1 ethyl acetate/DCM, 1 mL MeOH and 1 mL TEA for 100 mL) to afford the pure 2'-pyridyl-8-acetylenediazepines oxazole 3 as a white solid (410 mg, 82%); mp: 230-232° C.; $^1$H NMR (300 MHz, CDCl$_3$) δ 8.62 (d, J=4.2 Hz, 1H), 8.12 (s, 1H), 8.06 (d, J=7.8 Hz, 1H), 7.96 (s, 1H), 7.85 (ddd, J=1.8, 6.0 Hz, 1H), 7.79 (dd, J=1.8, 6.6 Hz, 1H), 7.62 (d, J=8.4 Hz, 1H), 7.55 (d, J=1.5 Hz, 1H), 7.53 (s, 1H), 7.41 (ddd, J=1.5, 4.8 Hz, 1H), 5.78 (d, J=12.9 Hz, 1H), 4.31 (d, J=12.9 Hz, 1H). $^{13}$C NMR (300 MHz, CDCl$_3$) δ 167.9, 156.7, 149.9, 149.0, 146.6, 137.0, 136.4, 135.8, 135.5, 135.3, 129.8, 127.5, 127.0, 124.9, 124.0, 122.8, 122.7, 121.0, 81.8, 79.5, 45.3; HRMS (ESI-TOF m/z) for C$_{21}$H$_{13}$N$_5$O calcd 352.1188, found 352.1193 (M+H)$^+$.

Example 2

Compound Assays

Explanation of Terms

EC3: A concentration of GABA eliciting 3% of the maximal GABA-elicited current amplitude of the individual oocyte.

log [M]: Represents the logarithm of molar concentration Assays of Competitive Binding to αxβ3γ2 GABAA Receptors The GABA$_A$ subunit selectivity of several compounds prepared as described above were determined using competitive binding assays. Competition binding assays were performed in a total volume of 0.5 mL at 4° C. for 1 h using [$^3$H]flunitrazepam as the radioligand (Savić, M. M.; Cook, J. M. et al. Progr. Neuro. Psychopharm. Biol. Psy. 2010, 34, 376-386). A total of 6 μg of cloned human GABA$_A$ receptor DNA containing desired α subtype along with β2 and γ2 subunits were used for transfecting HEK 293T cell line using Fugene 6 (Roche Diagnostic) transfecting reagent. Cells were harvested 48 h after transfection, washed with Tris-HCl buffer (pH 7.0) and Tris Acetate buffer (pH 7.4) and resulting pellets were stored at −80° C. until assayed. On the day of the assay, pellets containing 20-50 μg of GABA$_A$ receptor harvested with hypotonic buffer (50 mM Tris-acetate, pH 7.4, at 4° C.) was incubated with the radiolabel as previously described. Non-specific binding was defined as radioactivity bound in the presence of 100 μM diazepam and represented less than 20% of total binding. Membranes were harvested with a Brandel cell harvester followed by three ice-cold washes onto polyethyleneimine-pretreated (0.3%) Whatman GF/C filters. Filters were dried overnight and then soaked in Ecoscint A liquid scintillation cocktail (National Diagnostics; Atlanta, Ga.). Bound radioactivity was quantified by liquid scintillation counting. Membrane protein concentrations were determined using an assay kit from Bio-Rad (Hercules, Calif.) with bovine serum albumin as the standard.

Electrophysiological Experiments

Oocytes will be injected according to a standard method (Savic et al. Prog. Neuropsychopharmacol. Biol. Psychiatry 2010, 34(2):376-386) with different combinations of cDNA's comprised of different α-GABAergic cDNA's in combination with β3 and γ2 GABAergic cDNAs to express the different GABA$_A$ ion channels (Savic et al. Prog. Neuropsychopharmacol. Biol. Psychiatry 2010, 34(2):376-386). These will be used for the oocyte studies, applying an EC3 of GABA and then the drug being tested. For electrophysiological recordings, oocytes will be placed on a nylon-grid in a bath of Xenopus Ringer solution (XR, containing 90 mM NaCl, 5 mM HEPES-NaOH (pH 7.4), 1 mM MgCl$_2$, 1 mM KCl and 1 mM CaCl$_2$) The oocytes will be constantly washed by a flow of 6 ml/min XR which could be switched to XR containing GABA and/or drugs. Drugs were diluted into XR from DMSO-solutions resulting in a final concentration of 0.1% DMSO perfusing the oocytes. Drugs will be preapplied for 30 sec before the addition of GABA, which will be coapplied with the drugs until a peak response was observed. Between two applications, oocytes will be washed in XR for up to 15 min to ensure full recovery from desensitization. For current measurements the oocytes will be impaled with two microelectrodes (2-3 mΩ) which were filled with 2 mM KCl. All recordings will be performed at room temperature at a holding potential of −60 mV using a Warner OC-725C two-electrode voltage clamp (Warner Instruments, Hamden, Conn.). Data will be digitized, recorded and measured using a Digidata 1322A data acquisition system (Axon Instruments, Union City, Calif.). Results of concentration response experiments will be fitted using GraphPad Prism 3.00 (GraphPad Software, San Diego, Calif.).

The equation to be used for fitting concentration response curves will be Y=Bottom+(Top-Bottom)/(1+10^((Log EC50−X)*HillSlope)); X represents the logarithm of concentration, Y represents the response; Y starts at Bottom and goes to Top with a sigmoid shape. This is identical to the "four parameter logistic equation."

Concentration-effect curves can be prepared for various compounds tested on α1β3γ2, α2β3γ2, α3β3γ2, and α5β3γ2 $GABA_A$ receptors, using an EC3 GABA concentration.

Metabolic Stability for $GABA_A$ Receptor Ligands Using Human Liver Microsomes

The metabolic stability of $GABA_A$ receptor ligands using human liver microsomes will be studied. The test articles will be incubated at two concentrations (1 and 10 μM) and aliquots (100 μL) were removed at various time points (0, 15, 30, and 60 minutes), and analyzed by LC-MS/MS.

Example 3

Binding and Brain Fractions

KRM-II-81 was shown to have a great affinity in the nanomolar range for the α3-subtype (0.97 μM), complemented by a low affinity for the α1-subtype (testing was halted at greater than 20 μM). This α3 binding is comparable to the nonsedating anxiolytic, HZ-166 (0.84 μM). In a 10 mg/kg oral dose in rats, a concentration of 644 ng/g of KRM-II-81 was found unbound in the brain, indicating a great pharmacokinetic-profile. In addition, KRM-II-81 was not found to be a substrate of CYP3A4, CYP2D6, or CYP2C9; all of which are responsible for the metabolism of many other clinically used drugs.

Example 4

Marble Burying Assay

The marble burying assay is designed to measure the anxiolytic-effect of a compound. When mice are nervous, they will bury marbles. As there becomes a decrease in amount of marbles buried, the better anxiolytic effect of a compound. Herein, KRM-II-81 is shown to be a better anxiolytic than HZ-166, which is a published anxiolytic (Fischer et al. *Neuropharmacology*, 2010, 59, 612). KRM-II-81 also displayed less sedative effects than HZ-166 based on the rotarod assay, which implies that it have little to no amnesic or addictive properties.

Example 5

Pharmacokinetics

A 10 mg/kg P.O. dose was given for each of the compounds; however, HZ-166 used mice while KRM-II-81 used rats. Although these are different species, the numbers can still be compared. Data are summarized in TABLE 1.

TABLE 1

Highest concentration of compound, $C_{max}$, found in blood at time $T_{max}$.

|  | HZ-166 | KRM-II-81 |
|---|---|---|
| $C_{max}$ | 4.11 ng/mL | 1746 ng/mL |
| $T_{max}$ | 5.58 hours | 1.3 hours |

This data shows that the concentration of KRM-II-81 is nearly 500-times more concentrated in the blood than HZ-166. This leads to a higher concentration of the compound getting into the brain, which leads to a more effective compound. This data coupled with the brain unbound concentration ($[brain]_u$) of 644 ng/g and an 18% free fraction gives KRM-II-81 an exceptional profile. This is also superior to MP-III-080, which was also evaluated for the brain concentrations one hour after a 10 mg/kg oral dose. MP-III-080 produced a $[brain]_u$ of 340 ng/g and an 11% free fraction.

In vitro metabolism studies were done in mouse, rat, human, and dogs cells (TABLE 2).

TABLE 2

Percent of compound metabolized by in individual species.

| Mouse % Metabolized | Rat % Metabolized | Human % Metabolized | Dog % Metabolized |
|---|---|---|---|
| 10.1 | 9.6 | 8.6 | 5.9 |

In summary, the max concentration of the nonsedating anxiolytic/anticonvulsant/antinociceptive agent HZ-166 in rodents was 4.11 ng/mL; while KRM-II-81 came in at 1746 ng/mL. KRM-II-81 was found in the blood at nearly a 500-times higher concentration.

Example 6

Synthesis of Compounds

Figure 1:
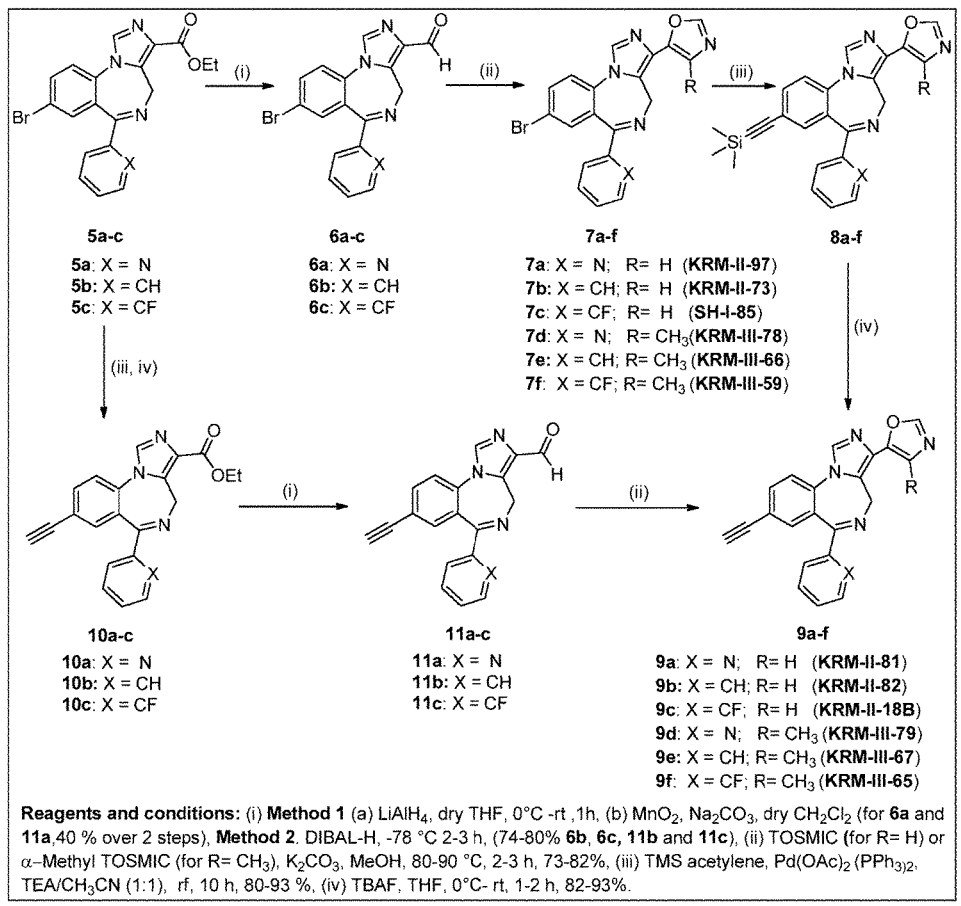
FIG. 1 is a synthetic scheme for the synthesis of the bioisosteres.
Figure 2:
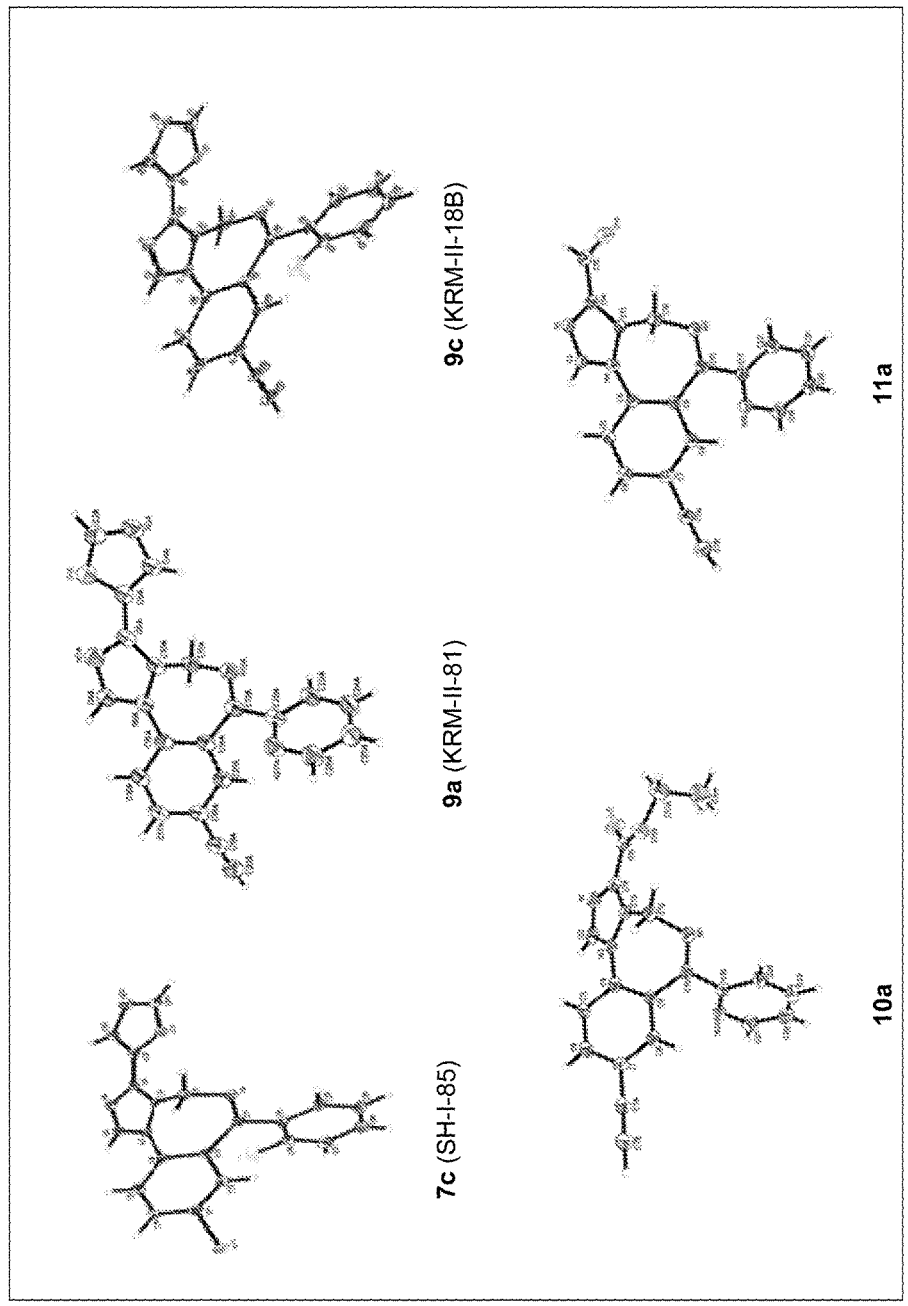
FIG. 2 are ORTEP views of the crystal structure of 7c (SH-I-85), 9a (KRM-II-81), 9c (KRM-II-18B), 10a, and 11a (displacement ellipsoids are at the 50% level).
Figure 3A:
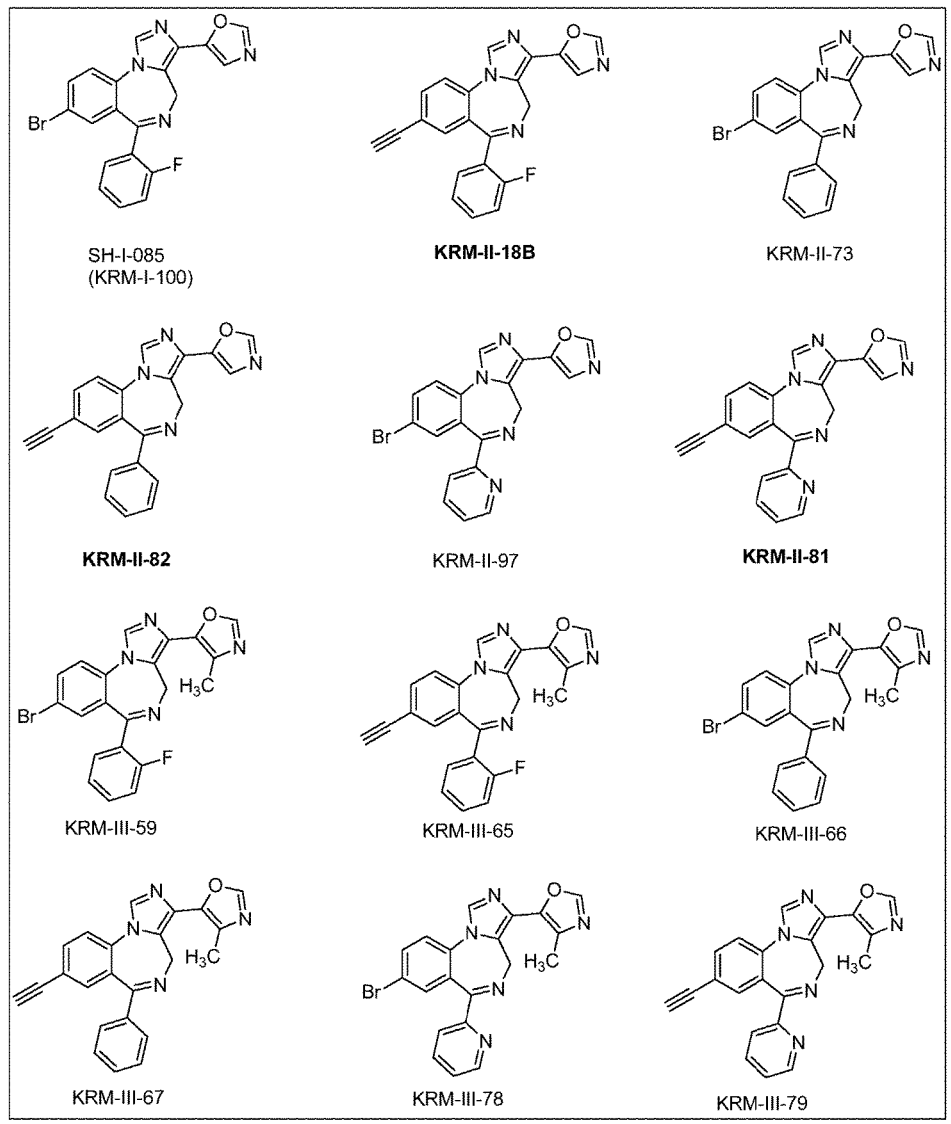
FIG. 3 are structures of compounds. Shown in A) are the imidazobenzodiazepine-bioisosteres, and shown in B) are structurally related compounds.
Figure 3B:
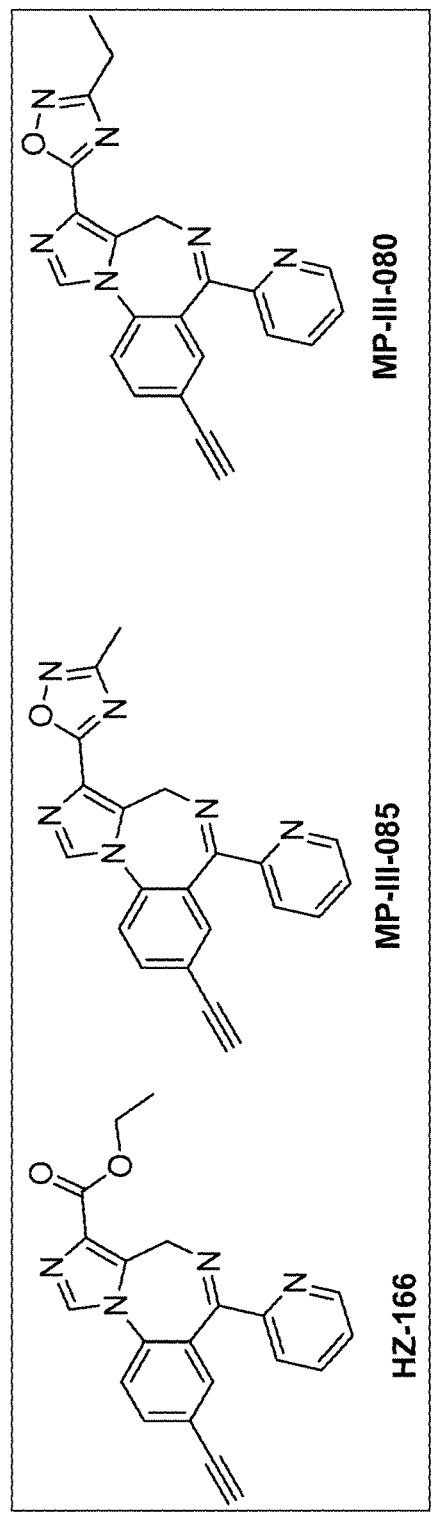

Compounds shown in FIG. 3 were synthesized according to the scheme shown in FIG. 1, with intermediates further shown in FIG. 2.

8-Bromo-6-(pyridin-2-yl)-4H-benzo[f]imidazo[1,5-a][1,4]diazepine-3-carbaldehyde (6a), Method 1

The ethyl ester of 2'-pyridyl benzimidazodiazepine 5a (500 mg, 1.21 mmol) was placed in an oven dried two neck round bottom flask and was then dissolved in dry THF. The reaction mixture was stirred at 0° C. and LiAlH$_4$ (50 mg, 1.34 mmol) was added to the reaction mixture at 0° C. After 10 min the reaction mixture was stirred at room temperature up to 45 min to 1 h under an argon atmosphere. After 45-60 min at room temperature analysis of the mixture by TLC (silica gel 1:9 MeOH/EtOAc) indicated the absence of starting ester 5a. The reaction mixture was slowly quenched with a saturated aqueous solvent of sodium sulfate (10 mL) at 0° C. and then the reaction mixture was diluted with ethyl acetate (30 mL). After this, the mixture was filtered through a small pad of Celite and then the filtrate was extracted with ethyl acetate (3×30 mL). The combined organic layers were washed with brine and dried over Na$_2$SO$_4$. The solvent was then removed under reduced presser to furnish the mixture of alcohols (imine alcohol 60% and reduced imine alcohol 40%, via analysis by H¹NMR spectroscopy) as a yellow solid. This mixture of alcohols was used directly in the next step. The mixture of 2'-pyridylalcohols (455 mg, 1.22 mmol) was dissolved in dry DCM (30 mL) under an argon atmosphere, after which $Na_2CO_3$ (384 mg, 3.66 mmol) and activated $MnO_2$ (278 mg, 14.4 mmol) were added to the reaction mixture at 0° C. The mixture was stirred at room temperature overnight. After completion of the reaction as indicated by TLC, the reaction mixture was diluted with DCM (30 mL) and was filtered through a small pad of Celite. The solvent was removed under reduced pressure to give the crude 2'-pyridyl aldehyde along with some other byproducts by TLC (1:9 MeOH/EtOAc). This material was purified by flash column chromatography using EtOAc/DCM/Hexane (2:1:1 and 1 mL MeOH+1 mLTEA for 100 mL) to afford the pure 2' pyridyl aldehyde 6a as a white solid (180 mg, 39.8% over two steps); mp: 220-222 OC. ¹H NMR (300 MHz, $CDCl_3$) δ 10.07 (s, 1H), 8.56 (d, J=2.4 Hz, 1H), 8.13 (d, J=7.8 Hz, 1H), 7.96 (s, 1H), 7.80-7.86 (m, 2H), 7.62 (s, 1H), 7.49 (d, J=8.4 Hz, 1H), 7.40 (t, J=7.2 Hz, 1H), 6.10 (br s, 1H), 4.15 (br s, 1H). (ESI) MS: m/z 368 (M+H)⁺. ¹³C NMR (75 MHz, $CDCl_3$) δ 186.7, 167.6, 156.3, 148.5, 137.7, 137.1, 136.8, 136.4, 135.5, 135.4, 135.0, 127.1, 124.9, 124.1, 122.9, 121.6, 81.5, 79.8, 44.3; HRMS (ESI-TOF m/z) for $C_{17}H_{11}BrN_4O$ calcd 367.0176 found 367.0189 (M+H)+.

8-Bromo-6-phenyl-4H-benzo[f]imidazo[1,5-a][1,4] diazepine-3-carbaldehyde (6b), Method 2

A solution of diisobutylaluminum hydride (8.5 mL of 1.0 M solution in hexane) was added dropwise to a vigorously stirred solution of the ester 5b (2.7 g, 6.58 mmol) in anhydrous dichloromethane (50 mL) under an argon atmosphere at −78° C. (dry ice-ethyl acetate). The reaction mixture was stirred for an additional 2-3 h at −78° C., and was monitored by TLC every 30 min. The temperature cannot be allowed to above −78° C. If the temperature gets above −78° C. other byproducts are formed (imine reduced aldehyde and alcohols). After completion of the reaction excess DIBAL-H was quenched by careful addition of dry methanol (5 mL), followed by 5% aq HCl (10 mL). After this the resulting mixture was allowed to warm to room temperature. If the reaction mixture forms an aluminum emulsion, a saturated solution aqueous solution of Rochelle's salt and DCM (50 mL) were added to the reaction mixture. It was then filtered through a pad of Celite and then the organic layer was separated. The aqueous layer which remained was extracted with DCM (2×30 mL). The combined organic layers were washed with brine and dried ($Na_2SO_4$). The solvent was removed under reduced pressure to afford the crude aldehyde. This residue was purified by flash chromatography (2:1 ethyl acetate/hexane) to afford the pure diazepine aldehyde 6b as a white solid, (2.0 g, 78%); mp 192-194° C. ¹H NMR (300 MHz, $CDCl_3$) δ 10.06 (s, 1H), 8.01 (s, 1H), 7.84 (d, J=8.4 Hz, 1H), 7.62 (s, 1H), 7.47-7.54 (m, 4H), 7.39-7.44 (m, 2H), 5.98 (d, J=12.6 Hz, 1H), 4.02 (d, J=12.3 Hz, 1H). ¹³C NMR (75 MHz, $CDCl_3$) δ 186.6, 168.2, 138.9, 138.3, 136.7, 135.2, 135.0, 134.8, 134.1, 130.9, 129.8, 129.3, 128.4, 124.2, 121.1, 44.2; HRMS (ESI-TOF m/z) for $C_{18}H_{12}BrN_3O$ calcd 366.0230 found 366.0236 (M+H)+.

8-Bromo-6-(2-fluorophenyl)-4H-benzo[f]imidazo[1,5-a][1,4]diazepine-3-carbaldehyde (6c)

The aldehyde 6c was prepared according to the method described for pyridine 6b, employing the 2'-F ethyl ester 5c (1.5 g, 3.51 mmol) and DIBAL-H (6.25 mL of 1.2 M solution in toluene, 20% w/v), to afford the pure aldehyde 6c as a white solid (1.0 g, 74.6%); mp 120-122° C. ¹H NMR (300 MHz, $CDCl_3$): δ 10.07 (s, 1H), 8.01 (s, 1H), 7.80 (dd, J=1.8, 6.6 Hz, 1H), 7.67 (ddd, J=1.5, 6.0 Hz, 1H), 7.45-7.52 (m, 3H), 7.25-7.30 (m, 1H), 7.04 (t, J=9.3 Hz, 1H), 6.02 (br s, 1H), 4.15 (br s, 1H). ¹³C NMR (75 MHz, $CDCl_3$) δ 186.6, 165.6, 161.8, 158.5, 137.8, 136.8, 135.4, 135.2, 134.1, 133.5, 132.6, 132.4, 131.3, 129.2, 127.6, 127.5, 122.5, 122.1, 116.4, 116.1, 44.2. HRMS (ESI-TOF m/z) for $C_{18}H_{11}BrFN_3O$ calcd 384.0145 found 384.0142 (M+H)+.

General Synthetic Procedure for oxazole Containing benzimidazodiazepines Through Van Leusen Reaction Via Baldwin's Rules 5-(8-Bromo-6-(pyridin-2-yl)-4H-benzo[f]imidazo[1,5-a][1,4]diazepin-3-yl)oxazole (7a)

The 2' pyridyldiazepine carboxaldehyde 6a (200 mg, 0.54 mmol) was placed in a dry two neck round bottom flask and dissolved in dry MeOH (30 mL) under an argon atmosphere. At rt, toluenesulfonylmethyl isocyanide (TosMIC, 130 mg, 0.65 mmol) was added as well as $K_2CO_3$ (225 mg, 1.6 mmol), The reaction mixture was heated to reflux for 3 to 4 h. After completion of the reaction on analysis by TLC (silica gel, 1:10 MeOH and EtOAc) this indicated the absence of aldehyde starting material and complete conversion to an oxazole of lower $R_f$. The reaction mixture was then quenched with cold water. After this 33% of the solvent was removed under reduced pressure and the solution was extracted with ethyl acetate (3×40 mL). The combined organic layers were washed with water and brine successively and dried ($Na_2SO_4$). The solvent was then removed under reduced pressure and the residue was purified by silica gel flash chromatography using EtOAc/DCM/Hexane (2:1:1 and 1 mL MeOH+1 mLTEA for 100 mL) to give the pure 2' pyridyldiazepine oxazole as white solid (170 mg, 77%); mp: 226-228° C. ¹H NMR (500 MHz, $CDCl_3$) δ 8.62 (d, J=4.5 Hz, 1H), 8.24 (s, 1H), 8.08 (d, J=8.0 Hz, 1H), 7.96 (s, 1H), 7.82-7.87 (m, 2H), 7.57-7.59 (m, 2H), 7.40-7.43 (m, 1H), 5.78 (d, J=12.5 Hz, 1H), 4.32 (d, J=12.5 Hz, 1H), (ESI) MS: m/z 368 (M+H)⁺.)⁺. ¹³C NMR (300 MHz, $CDCl_3$) δ 167.2, 155.9, 150.1, 148.7, 145.4, 137.2, 135.3, 135.2, 134.4, 133.3, 129.6, 128.3, 126.9, 125.1, 124.5, 124.1, 123.4, 120.8, 44.9; HRMS (ESI m/z) for $C_{19}H_{12}BrN_5O$ calcd 406.0299, found 406.0298 (M+H)⁺.

5-(8-Bromo-6-phenyl-4H-benzo[f]imidazo[1,5-a][1,4]diazepin-3-yl)oxazole (7b)

The reaction was performed following the same procedure for 7a, employing diazepine aldehyde 6b (720 mg, 1.9 mmol), TosMIC (460 mg, 2.36 mmol) and $K_2CO_3$ (977 mg, 7.08 mmol). This afforded the crude oxazole which was purified by flash silica gel chromatography (4:1 ethyl acetate/hexane) to give a white solid 7b (601 mg, 78% yield); mp 225-227° C. ¹H NMR (300 MHz, $CDCl_3$) δ 8.05 (s, 1H), 7.92 (s, 1H), 7.81 (dd, J=1.8, 6.6 Hz, 1H), 7.82 (d, J=8.4 Hz, 1H), 7.53-7.57 (m, 3H), 7.43-7.49 (m, 2H), 7.39-7.43 (m, 2H), 5.75 (d, J=12.6 Hz, 1H), 4.24 (d, J=12.6 Hz, 1H). ¹³C NMR (300 MHz, $CDCl_3$) δ 167.9, 156.7, 149.9, 148.9, 146.6, 137.0, 136.4, 135.8, 135.4, 135.3, 129.8, 127.5, 127.0, 124.9, 124.0, 122.8, 122.6, 121.0, 45.3; HRMS (ESI m/z) for $C_{20}H_{13}N_4OBr$ calcd 405.0349, found 405.0345 (M+H)⁺.

5-(8-Bromo-6-(2-fluorophenyl)-4H-benzo[f]imidazo[1,5-a][1,4]diazepin-3-yl)oxazole (7c)

The 2'-F oxazole 7c was prepared according to the method described for 7a employing 2'-F diazepine aldehyde 6c (649 mg, 1.53 mmol), TosMIC (330 mg, 1.68 mmol) and $K_2CO_3$ (640 mg, 4.60 mmol). This afforded the crude oxazole which was purified by flash silica gel chromatography (3:1 ethyl acetate/hexane) to give 2'-F oxazole 7c as a white solid (550 mg, 76.7% yield); mp: 190-192° C. $^1$H NMR (300 MHz, $CDCl_3$) δ 8.01 (s, 1H), 7.92 (s, 1H), 7.77 (dd, J=2.1, 6.6 Hz, 1H), 7.77 (ddd, J=1.5, 6.0 Hz, 1H), 7.52 (s, 1H), 7.46-7.52 (m, 3H), 7.23-7.28 (m, 1H), 7.04 (t, J=8.4 Hz, 1H), 5.75 (br s, 1H), 4.26 (br s, 1H). $^{13}$C NMR (300 MHz, $CDCl_3$) δ 165.0, 161.8, 158.5, 149.8, 146.5, 135.1, 134.9, 133.6, 133.3, 132.5, 131.1, 130.4, 129.7, 127.6, 124.6, 124.0, 122.6, 120.9, 116.4, 116.1, 45.3; HRMS (ESI-TOF m/z) for $C_{20}H_{12}N_4OFBr$ calcd 423.0263, found 423.0251 (M+H)$^+$.

5-(8-Bromo-6-(pyridin-2-yl)-4H-benzo[f]imidazo[1,5-a][1,4]diazepin-3-yl)-4-methyloxazole (7d)

The 2'-N methyl oxazole 7d was prepared according to the method described for 7a, employing 2'-N aldehyde 6a (300 mg, 0.815 mmol), 1-((1-isocyanoethyl)sulfonyl)-4-methylbenzene (α-methyl TosMIC, 196 mg, 0.978 mmol) and $K_2CO_3$ (340 mg, 2.44 mmol). This afforded the crude oxazole which was purified by flash silica gel chromatography EtOAc/DCM (1:1 and 1 mL MeOH+1 mLTEA for 100 mL) to give 2'-N methyl oxazole 7d as a half white solid (250 mg, 73% yield); mp 228-230° C. $^1$H NMR (500 MHz, $CDCl_3$) δ 8.60 (d, J=3.6 Hz, 1H), 8.07 (d, J=7.5 Hz, 1H), 7.96 (s, 1H), 7.77-7.86 (m, 3H), 7.57 (s, 1H), 7.47 (d, J=8.7 Hz, 1H), 7.38 (t, J=5.4 Hz, 1H), 5.71 (d, J=11.7 Hz, 1H), 4.28 (d, J=12.3 Hz, 1H), 2.52 (s, 3H); $^{13}$C NMR (300 MHz, $CDCl_3$) δ 167.0, 156.4, 148.7, 140.6, 136.9, 135.2, 134.9, 134.8, 132.7, 129.8, 128.4, 128.1, 124.8, 124.1, 123.8, 120.1, 45.2, 12.37; HRMS (ESI-TOF m/z) for $C_{20}H_{14}N_5OBr$ calcd 420.0450, found 420.0456 (M+H)$^+$.

5-(8-Bromo-6-phenyl-4H-benzo[f]imidazo[1,5-a][1,4]diazepin-3-yl)-4-methyloxazole (7e)

The methyl 2'-H methyl oxazole compound 7e was prepared according to the method described for 7a, employing the 2'-H aldehyde 6b (500 mg, 1.366 mmol), 1-((1-isocyanoethyl)sulfonyl)-4-methylbenzene (α-methyl TosMIC, 342 mg, 1.6 mmol) and $K_2CO_3$ (565 mg, 4.0 mmol). This afforded the crude solid which was purified by flash chromatography (4:1 ethyl acetate/hexane) to give a half white 2'-H methyl oxazole as a solid 7e (450 mg, 78% yield); mp 236-238° C. $^1$H NMR (300 MHz, $CDCl_3$) δ 7.99 (s, 1H), 7.85 (s, 1H), 7.80 (dd, J=3.0, 8.4 Hz, 1H), 7.58 (d, J=2.1 Hz, 1H), 7.47-7.53 (m, 3H), 7.37-7.42 (m, 3H), 5.67 (d, J=13.2 Hz, 1H), 4.20 (d, J=12.6 Hz, 1H), 2.52 (s, 3H). $^{13}$C NMR (75 MHz, $CDCl_3$) δ 168.0, 148.6, 140.6, 139.3, 135.0, 134.9, 134.8, 134.4, 132.7, 130.6, 130.3, 129.6, 129.3, 128.4, 128.2, 124.1, 120.2, 45.1, 12.3; HRMS (ESI-TOF m/z) for $C_{21}H_{15}N_4OBr$ calcd 419.0500, found 419.0502 (M+H)$^+$.

5-(8-Bromo-6-(2-fluorophenyl)-4H-benzo[f]imidazo[1,5-a][1,4]diazepin-3-yl)-4-methyloxazole (7f)

The 2'-F methyl oxazole 7f was prepared according to the method described for 7a, employing the 2'-F aldehyde 6c (300 mg, 0.782 mmol), 1-((1-isocyanoethyl)sulfonyl)-4-methylbenzene (α-methyl TosMIC, 196 mg, 0.938 mmol) and $K_2CO_3$ 325 mg, 2.34 mmol). This afforded the crude solid which was purified by flash chromatography (4:1 ethyl acetate/hexane) to give a half white 2'-F methyl oxazole as a solid 7f (260 mg, 76% yield); mp 138-140° C. $^1$H NMR (500 MHz, $CDCl_3$) δ 8.04 (s, 1H), 7.84 (s, 1H), 7.78 (d, J=8.0 Hz, 1H), 7.77 (t, J=7.0 Hz, 1H), 7.46-7.52 (m, 3H), 7.23-7.28 (m, 1H), 7.05 (t, J=8.5 Hz, 1H), 5.72 (br s, 1H), 4.24 (br s, 1H), 2.53 (s, 3H); $^{13}$C NMR (75 MHz, $CDCl_3$) δ 164.8, 161.8, 158.5, 148.75, 140.65, 135.1, 134.7, 133.7, 133.2, 132.8, 132.4, 132.3, 131.2, 131.1, 130.4, 129.9, 128.2, 127.6, 127.5, 124.5, 124.1, 120.7, 116.4, 116.1, 45.3, 12.3. HRMS (ESI-TOF m/z) for $C_{21}H_{14}N_4OFBr$ calcd 437.0403 found 437.0408 (M+H)$^+$.

General Synthetic Procedures for Sonogashira Coupling

5-(6-(Pyridin-2-yl)-8-((trimethylsilyl)ethynyl)-4H-benzo[f]imidazo[1,5-a][1,4]diazepin-3-yl)oxazole (8a)

The 2'-N bromide 7a (200 mg, 0.50 mmol) and bis(triphenylphosphine)-palladium (II) acetate (18 mg, 0.024 mmol) were added to an oven dried two neck round bottom flask, after which the round bottom flask was fitted with a rubber septum. It was then evacuated under vacuum and back filled with argon three times. After this, a mixed dry solvent system of $CH_3CN$:TEA (1:2 ratio) and trimethylsilylacetylene (0.3 mL, 2.07 mmol) were added to the round bottom flask with a syringe under a positive pressure of argon. The round bottom flask was fitted with a reflex condenser and the reaction mixture was degassed under vacuum and argon, the process was repeated two to three times, after which the reaction mixture was slowly heated to 90° C. After stirring for 10 h, the reaction mixture was filtered through a bed of Celite. The organic layer was washed with brine and dried ($Na_2SO_4$). The solvent was then removed under reduced pressure to furnish a crude solid. This material was purified by flash chromatography using EtOAc/DCM/Hexane (2:1:1 and 1 mL MeOH+1 mLTEA for 100 mL) to afford the pure 2'-N trimethylsilylacetylene intermediate as a light brown solid (170 mg, 80.6% yield); mp 208-210° C. $^1$H NMR (300 MHz, $CDCl_3$) δ 8.63 (d, J=4.1 Hz, 1H), 8.26 (s, 1H), 8.06 (d, J=8.0 Hz, 1H), 7.97 (s, 1H), 7.82-7.88 (m, 2H), 7.57-7.59 (m, 2H), 7.40-7.43 (m, 1H), 5.78 (d, J=12.3 Hz, 1H), 4.32 (d, J=12.3 Hz, 1H), 0.22 (s, 9H); $^{13}$C NMR (75 MHz, $CDCl_3$) δ 167.6, 149.8, 146.5, 139.5, 135.3, 134.8, 132.1, 131.9, 131.6, 130.5, 130.2, 129.3, 128.6, 128.3, 127.8, 127.1, 122.5, 122.4, 122.2, 102.5, 97.4, 44.9, −0.0.22; HRMS (ESI-TOF m/z) for $C_{24}H_{21}N_5OSi$ calcd 424.1816, found 424.1810 (M+H)$^+$.

5-(6-Phenyl-8-((trimethylsilyl)ethynyl)-4H-benzo[f]imidazo[1,5-a][1,4]diazepin-3-yl)oxazole (8b)

The 2'-H trimethylsilylacetylenediazepine oxazole 8b was prepared according to the method described for 8a, employing the 2'-H bromodiazepine oxazole 7b (700 mg, 1.72 mmol), bis(triphenylphosphine)palladium(II)acetate (64 mg, 0.0864 mmol) and trimethylsilylacetylene (0.3 mL, 2.07 mmol). The residue which resulted was purified by silica gel flash column chromatography (4:1 ethyl acetate/hexane) to give a white solid 8b (650 mg, 89.6% yield); mp 126-128° C. $^1$H NMR (300 MHz, $CDCl_3$) δ 8.00 (s, 1H), 7.93 (s, 1H), 7.81 (dd, J=1.5, 8.4 Hz, 1H), 7.65-7.72 (m, 1H), 7.51-7.57 (m, 4H), 7.38-7.47 (m, 4H), 5.70 (d, J=12.6 Hz, 1H), 4.19 (d, J=12.6 Hz, 1H), 0.25 (s, 9H); $^{13}$C NMR (300 MHz, $CDCl_3$)

δ 168.8, 149.8, 146.5, 139.5, 135.3, 134.8, 132.1, 131.9, 131.6, 130.5, 130.2, 129.3, 128.6, 128.3, 127.8, 127.1, 122.5, 122.4, 122.2, 102.5, 97.4, 44.9, −0.23; HRMS (ESI-TOF m/z) for $C_{25}H_{22}N_4OSi$ calcd 423.1630, found 423.1636 $(M+H)^+$.

5-(6-(2-Fluorophenyl)-8-((trimethylsilyl)ethynyl)-4H-benzo[f]imidazo[1,5-a][1,4]diazepin-3-yl)oxazole (8c)

The 2'-F trimethylsilylacetylenediazepine oxazole 8c was prepared according to the method described for 8a, employing the 2'-F bromodiazepine oxazole 7c (100 mg, 0.23 mmol) bis(triphenylphosphine)palladium(II)acetate (10 mg, 0.011 mmol) and trimethylsilylacetylene (0.04 mL, 0.26 mmol). After work up the residue which resulted was purified by silica gel flash column chromatography (4:1 ethyl acetate/hexane) to give a light brown solid 8c (90 mg, 92.6% yield). $^1$H NMR (300 MHz, $CDCl_3$) δ 8.02 (s, 1H), 7.92 (s, 1H), 7.60-7.74 (m, 3H), 7.40-7.57 (m, 3H), 7.23-7.28 (m, 1H), 7.04 (t, J=9.0 Hz, 1H), 5.73 (br s, 1H), 4.24 (br s, 1H), 0.24 (s, 9H). $^{13}$C NMR (75 MHz, $CDCl_3$) δ 165.6, 161.9, 158.4, 148.7, 140.7, 135.4, 134.7, 134.3, 133.7, 132.7, 132.1, 131.1, 131.3, 129.9, 128.8, 128.3, 128.1, 124.4, 122.4, 116.5, 116.2, 102.5, 97.2, 45.1, −0.23; HRMS (ESI-TOF m/z) for $C_{25}H_{21}N_4OFSi$ calcd 441.1543, found 441.1541 $(M+H)^+$.

4-Methyl-5-(6-phenyl-8-((trimethylsilyl)ethynyl)-4H-benzo[f]imidazo[1,5-a][1,4]diazepin-3-yl)oxazole (8e)

The 2'-H trimethylsilylacetylenediazepine methyl oxazole 8e was prepared according to the method described for 8a, employing the bromo 2'-H trimethylsilylacetylenediazepine methyl oxazole 7e (250 mg, 1.72 mmol), bis(triphenylphosphine)palladium(II)acetate (17 mg, 0.0238 mmol) and trimethylsilyl acetylene (0.074 mL, 0.52 mmol). The residue which resulted was purified by silica gel flash column chromatography (4:1 ethyl acetate/hexane) to give a light brown solid 8b (188 mg, 90% yield); mp130-132° C. $^1$H NMR (300 MHz, $CDCl_3$) δ 8.00 (s, 1H), 7.93 (s, 1H), 7.81 (dd, J=1.5, 8.4 Hz, 1H), 7.65-7.72 (m, 1H), 7.51-7.57 (m, 4H), 7.38-7.47 (m, 4H), 5.70 (d, J=12.6 Hz, 1H), 4.19 (d, J=12.6 Hz, 1H), 0.25 (s, 9H); $^{13}$C NMR (300 MHz, $CDCl_3$) δ 168.8, 149.8, 146.5, 139.5, 135.3, 134.8, 132.1, 131.9, 131.6, 130.5, 130.2, 129.3, 128.6, 128.3, 127.8, 127.1, 122.5, 122.4, 122.2, 102.5, 97.4, 44.9, −0.23; HRMS (ESI-TOF m/z) for $C_{26}H_{24}N_4OSi$ calcd 437.1638, found 437.1636 $(M+H)^+$.

5-(6-(2-Fluorophenyl)-8-((trimethylsilyl)ethynyl)-4H-benzo[f]imidazo[1,5-a][1,4]diazepin-3-yl)-4-methyloxazole (8f)

The 2'-F trimethylsilylacetylenediazepine methyl oxazole 8f was prepared according to the method described for 8a, employing the bromo 2'-F trimethylsilylacetylenediazepine methyl oxazole 7f (900 mg, 2.059 mmol), bis(triphenylphosphine)palladium(II)acetate (77 mg, 0.103 mmol) and trimethyl silylacetylene (0.321 mL, 2.65 mmol). The residue which resulted was purified by silica gel flash column chromatography (4:1 ethyl acetate/hexane) to give a brown solid 8f (800 mg, 87% yield); mp 209-211° C. $^1$H NMR (300 MHz, $CDCl_3$) δ 8.03 (s, 1H), 7.83 (s, 1H), 7.71 (dd, J=1.8, 8.1 Hz, 1H), 7.63 (td, J=1.8, 7.5 Hz, 1H), 7.40-7.53 (m, 3H), 7.23-7.28 (m, 1H), 7.04 (t, J=10.2 Hz, 1H), 5.69 (br s, 1H), 4.21 (br s, 1H), 2.53 (s, 3H), 0.25 (s, 9H); $^{13}$C NMR (75 MHz, $CDCl_3$) δ 165.4, 161.9, 158.5, 148.6, 140.7, 135.3, 134.6, 134.2, 133.7, 132.7, 132.1, 131.0, 131.2, 129.9, 128.8, 128.2, 128.0, 124.4, 122.4, 116.4, 116.1, 102.6, 97.1, 45.1, 12.3, −0.23; HRMS (ESI-TOF m/z) for $C_{26}H_{23}N_4OFSi$ calcd 455.1690, found 455.1698 $(M+H)^+$.

5-(8-Ethynyl-6-(pyridin-2-yl)-4H-benzo[f]imidazo[1,5-a][1,4]diazepin-3-yl)oxazole (9a)

A solution of 2'-N trimethylsilylacetylene oxazole intermediate 8a (150 mg, 0.35 mmol) was dissolved in dry THF and kept at 0° C. after which tetrabutylammonium iodide (0.12 mL, 0.39 mmol) was added slowly to the reaction mixture at 0° C. After 10 min the reaction mixture was stirred at room temperature for 2 h under an argon atmosphere. After TLC on silica gel indicated the absence of starting material, this reaction mixture was quenched by slow addition of ice cold water and the combined layers were extracted with ethyl acetate (3×30 mL). The combined organic layers were washed with water and brine. This solution was dried over $Na_2SO_4$ and the solvent was removed under reduced pressure to furnish a solid. This material was then purified by flash chromatography using EtOAc/DCM/Hexane (2:1:1 and 1 mL MeOH +1 mLTEA for 100 mL) to afford the pure 2'-N acetyleno oxazole 9a as a white solid (101 mg, 82% yield); mp 220-222° C. $^1$H NMR (300 MHz, $CDCl_3$) δ 8.62 (d, J=4.2 Hz, 1H), 8.12 (s, 1H), 8.06 (d, J=7.8 Hz, 1H), 7.96 (s, 1H), 7.85 (ddd, J=1.8, 6.0 Hz, 1H), 7.79 (dd, J=1.8, 6.6 Hz, 1H), 7.62 (d, J=8.4 Hz, 1H), 7.55 (d, J=1.5 Hz, 1H), 7.53 (s, 1H), 7.41 (ddd, J=1.5, 4.8 Hz, 1H), 5.78 (d, J=12.9 Hz, 1H), 4.31 (d, J=12.9 Hz, 1H). $^{13}$C NMR (75 MHz, $CDCl_3$) δ 167.9, 156.7, 149.9, 149.0, 146.6, 137.0, 136.4, 135.8, 135.5, 135.3, 129.8, 127.5, 127.0, 124.9, 124.0, 122.8, 122.7, 121.0, 81.8,7, 79.5, 45.3; HRMS (ESI-TOF m/z) for $C_{21}H_{13}N_5O$ calcd 352.1188, found 352.1193 $(M+H)^+$.

5-(8-Ethynyl-6-phenyl-4H-benzo[f]imidazo[1,5-a][1,4]diazepin-3-yl)oxazole (9b)

The 2'-H acetyleno oxazole 9b was prepared according to the method described for 7a, employing the 2'-H trimethylsilylacetylenodiazepine oxazole 8b (500 mg, 1.18) and TBAF (0.5 mL, 1.76 mmol). After workup, the residue was purified by silica gel flash column chromatography (4:1 ethyl acetate/hexane) to afford 2'-H acetyleno oxazole 9b as a white solid (370 mg, 90% yield); mp 120-122° C. $^1$H NMR (300 MHz, $CDCl_3$) δ 8.08 (s, 1H), 7.93 (s, 1H), 7.81 (dd, J=1.8, 6.6 Hz, 1H), 7.81 (d, J=8.4 Hz, 1H), 7.53-7.57 (m, 3H), 7.43-7.49 (m, 2H), 7.39-7.43 (m, 2H), 5.75 (d, J=12.9 Hz, 1H), 4.24 (d, J=12.9 Hz, 1H), 3.18 (s, 1H). $^{13}$C NMR (300 MHz, $CDCl_3$) δ 167.9, 156.7, 149.9, 148.9, 146.6, 137.0, 136.4, 135.8, 135.4, 135.3, 129.8, 127.5, 127.0, 124.9, 124.0, 122.8, 122.6, 121.0, 81.8, 79.5, 45.2; HRMS (ESI-TOF m/z) for $C_{22}H_{14}N_4O$ calcd 351.1246, found 351.1240 $(M+H)^+$.

5-(8-Ethynyl-6-(2-fluorophenyl)-4H-benzo[f]imidazo[1,5-a][1,4]diazepin-3-yl)oxazole (9c)

The 2'-F acetyleno oxazole 9c was prepared according to the method described for 9a, employing the 2'-F TMS-acetyleno-2'-fluorodiazepine oxazole 8c (90 mg, 0.20 mmol), and TBAF (0.05 mL, 024 mmol). After workup the residue was purified by silica gel flash column chromatography (4:1 ethyl acetate/hexane) to give the 2'-F acetyleno oxazole 9c as a white solid (80 mg, 88% yield); mp 212-214° C. $^1$H NMR (300 MHz, CDCl$_3$) δ 8.03 (s, 1H), 7.93 (s, 1H), 7.75 (d, J=7.8 Hz, 1H), 7.57-7.63 (m, 2H), 7.44-7.53 (m, 3H), 7.23-7.28 (m, 1H), 7.04 (t, J=9.0 Hz, 1H), 5.74 (br s, 1H), 4.26 (br s, 1H), 3.16 (s, 1H). $^{13}$C NMR (300 MHz, CDCl$_3$) δ 165.5, 161.9, 158.5, 149.8, 146.5, 135.4, 135.0, 134.3, 132.3, 131.1, 129.8, 128.9, 127.8, 127.5, 124.5, 122.6, 121.6, 116.4, 116.1, 81.4, 79.6, 45.0; HRMS (ESI-TOF m/z) for C$_{22}$H$_{13}$N$_4$OF calcd 369.1144, found 369.1146 (M+H)$^+$.

5-(8-Ethynyl-6-phenyl-4H-benzo[f]imidazo[1,5-a][1,4]diazepin-3-yl)-4-methyloxazole (9e)

The 2'-H acetyleno methyl oxazole 9e was prepared according to the method described for 9a, employing the TMS-acetyleno-2'-H methyl oxazole 8c (250 mg, 0.573 mmol), and TBAF (0.19 mL, 0.68 mmol). After workup the residue was purified by silica gel flash column chromatography (4:1 ethyl acetate/hexane) to give the 2'-H acetyleno methyl oxazole 9e as a white solid (190 mg, 91% yield); mp 228-230° C. $^1$H NMR (300 MHz, CDCl$_3$) δ 8.01 (s, 1H), 7.85 (s, 1H), 7.77 (dd, J=1.8, 8.4 Hz, 1H), 7.56-7.60 (m, 2H), 7.49-7.53 (m, 2H), 7.37-7.46 (m, 3H), 5.67 (d, J=12.9 Hz, 1H), 4.20 (d, J=12.9 Hz, 1H), 3.17 (s, 1H), 2053 (s, 3H); $^{13}$C NMR (300 MHz, CDCl$_3$) δ 168.5, 148.7, 140.6, 139.5, 135.9, 135.8, 135.3, 134.5, 132.8, 130.5, 130.3, 129.3, 128.3, 128.2, 128.0, 122.6, 121.0, 81.5, 79.6, 45.3, 12.3; HRMS (ESI-TOF m/z) for C$_{23}$H$_{16}$N$_4$O calcd 365.1400 found 365.1397 (M+H)$^+$.

5-(8-Ethynyl-6-(2-fluorophenyl)-4H-benzo[f]imidazo[1,5-a][1,4]diazepin-3-yl)-4-methyloxazole (9f)

The 2'-F acetyleno methyl oxazole 9e was prepared according to the method described for 9a, employing the TMS-acetyleno-2'-H methyl oxazole 8c (500 mg, 1.147 mmol), and TBAF (0.390 mL, 1.37 mmol). After workup the residue was purified by silica gel flash column chromatography (4:1 ethyl acetate/hexane) to give the 2'-F acetyleno methyl oxazole 9f as a white solid (395 mg, 90% yield); mp 145-147° C. $^1$H NMR (300 MHz, CDCl$_3$) δ 8.03 (s, 1H), 7.84 (s, 1H), 7.74 (d, J=7.8 Hz, 1H), 7.55-7.65 (m, 2H), 7.46 (s, 2H), 7.22-7.28 (m, 1H), 7.03 (t, J=8.1 Hz, 1H), 5.70 (br s, 1H), 4.25 (br s, 1H), 3.16 (s, 1H), 2.53 (s, 3H). $^{13}$C NMR (75 MHz, CDCl$_3$) δ 165.4, 161.9, 158.5, 148.7, 140.6, 135.4, 134.6, 134.2, 132.8, 132.2, 132.1, 131.2, 131.1, 129.9, 128.9, 128.3, 127.9, 127.8, 124.5, 124.4, 122.5, 121.4, 116.4, 116.1, 81.5, 79.9, 45.1, 12.3; HRMS (ESI-TOF m/z) for C$_{23}$H$_{15}$N$_4$OF calcd 383.1300 found 383.1303 (M+H)$^+$.

General Synthetic Procedures for Sonogashira Coupling and Desilylation

Ethyl-8-ethynyl-6-(pyridin-2-yl)-4H-benzo[f]imidazo[1,5-a][1,4]diazepine-3-carboxylate (10a)

The 2'-N bromide ethyl ester 5a (17.0 g, 41.2 mmol) and bis(triphenylphosphine)-palladium (II) acetate (1.50 g, 2.06 mmol) were added to an oven dried two neck round bottom flask, after which the round bottom flask was fitted with a rubber septum. It was then evacuated under vacuum and back filled with argon three times. After this, a mixed dry solvent system of CH$_3$CN:TEA (1:2 ratio) and trimethylsilylacetylene (6.4 mL, 45.40 mmol) were added to the round bottom flask with a syringe under a positive pressure of argon. The round bottom flask was fitted with a reflex condenser and the reaction mixture was degassed under vacuum and argon, the process was repeated two to three times, after which the reaction mixture was slowly heated to 90° C. After stirring for 10 h, the reaction mixture was filtered through a bed of Celite. The organic layer was washed with brine and dried (Na$_2$SO$_4$). The solvent was then removed under reduced pressure to furnish a crude solid. This material was purified by flash chromatography using EtOAc/DCM/Hexane (2:1:1 and 1 mLTEA for 100 mL) to afford the pure 2'-N trimethylsilyl acetyleno intermediate (14.12 g, 80% yield) as a light brown solid. And this intermediate (14.12 mg, 3.30 mmol) was dissolved in dry THF and kept at 0° C. after which tetrabutylammonium iodide (10.30 mL, 3.62 mmol) was added slowly to the reaction mixture at 0° C. After 10 min the reaction mixture was stirred at room temperature for 2 h under an argon atmosphere. After TLC on silica gel indicated the absence of starting material, this reaction mixture was quenched by slow addition of ice cold water and the combined layers were extracted with ethyl acetate (2×150 mL). The combined organic layers were washed with water and brine. This solution was dried over Na$_2$SO$_4$ and the solvent was removed under reduced pressure to furnish a solid. This material was then purified by flash chromatography using EtOAc/DCM/Hexane (2:1:1 and 1 mLTEA for 100 mL) to afford the pure 2'-N acetyleno ethyl ester 10a as a white solid (9.63 g, 82% yield); mp 248-250° C. $^1$H NMR (300 MHz, CDCl$_3$) δ 8.58 (d, J=4.8 Hz, 1H), 8.07 (d, J=7.8 Hz, 1H), 7.92 (s, 1H), 7.82 (td, J=1.8, 7.8 Hz, 1H), 7.57-7.59 (dd, J=1.5, 8.4 Hz, 1H), 7.54-7.57 (m, 2H), 7.37 (td, J=0.9, 4.8 Hz, 1H), 6.14 (d, J=9.9 Hz, 1H), 4.42 (q, J=3.9, 7.2 Hz, 2H), 4.16 (d, J=10.2 Hz, 1H), 3.17 (s, 1H), 1.44 (t, J=7.2 Hz, 1H); $^{13}$C NMR (75 MHz, CDCl$_3$) δ 167.5, 162.9, 156.2, 148.6, 138.3, 137.1, 136.1, 135.4, 135.3, 134.5, 129.2, 127.0, 124.9, 124.1, 122.9, 121.3, 81.6, 79.5, 60.8, 45.0, 14.4; HRMS (ESI-TOF m/z) for C$_{21}$H$_{16}$N$_4$O calcd 357.1340, found 357.1346 (M+H)$^+$.

Ethyl 8-ethynyl-6-phenyl-4H-benzo[f]imidazo[1,5-a][1,4]diazepine-3-carboxylate (10b)

The 2'-H acetyleno ethyl ester 10b was prepared according to the method described for 10a, employing the 2'-H bromodiazepine ethyl ester 5b (10.0 g, 24.40 mmol), bis(triphenylphosphine)palladium(II)acetate (913 mg, 1.22 mmol) and trimethylsilylacetylene (3.82 mL, 26.84 mmol). The residue was purified by flash chromatography (3:1 ethyl acetate/hexane) to afford the 2'-H trimethylsilyl acetyleno intermediate (9.48 mg, 91.0% yield). And this intermediate (9.48 mg, 22.20 mmol). was treated with tetrabutylammonium iodide (7.0 mL, 24.42 mmol), this resulting material was purified by flash column chromatography using EtOAc/Hexane (4:1) to afford the pure 2'-H acetyleno ethyl ester 10b as a white solid (7.33 mg, 93.0% yield); mp 237-239° C. $^1$H NMR (300 MHz, CDCl$_3$) δ 8.00 (s, 1H), 7.81 (dd, J=1.8, 8.3 Hz, 1H), 7.65-7.72 (m, 2H), 7.51-7.57 (m, 3H), 7.38-7.47 (m, 2H), 6.11 (d, J=12.6 Hz, 1H), 4.41-4.48 (m, 2H), 4.19 (d, J=12.6 Hz, 1H), 3.20 (s, 1H), 1.44 (t, J=7.3 Hz, 3H); $^{13}$C NMR (75 MHz, CDCl$_3$) δ 168.3, 138.8, 138.4, 136.7, 135.3, 135.0, 134.8, 134.1, 130.9, 129.8, 129.2, 128.3, 124.2, 121.1, 81.3, 80.0, 60.6, 44.2, 14.7; HRMS (ESI-TOF m/z) for C$_{22}$H$_{17}$N$_3$O$_2$ calcd 356.1390 found 356.1394 (M+H)+.

Ethyl-8-ethynyl-6-(2-fluorophenyl)-4H-benzo[f]imidazo[1,5-a][1,4]diazepine-3-carboxylate (10c)

The 2'-F acetyleno ethyl ester 10c was prepared according to the method described for 10a, employing the 2'-F bromodiazepine ethyl ester 5c (7 g, 16.35 mmol), bis(triphenylphosphine)palladium(II)acetate (612 mg, 0.817 mmol) and trimethylsilylacetylene (2.56 mL, 18.0 mmol). The residue was purified by flash chromatography (3:1 ethyl acetate/hexane) to afford the 2'-F trimethylsilyl acetyleno intermediate (6.47 g, 89.0% yield). And this intermediate (6.47 g, 14.55 mmol) was treated with tetrabutylammonium iodide (4.54 mL, 16.0 mmol), this resulting material was purified by flash column chromatography using EtOAc/Hexane (4:1) to afford the pure 2'-F acetyleno ethyl ester 10c as a white solid (4.89 g, 90.0% yield); mp 232-234° C. $^1$H NMR (300 MHz, CDCl$_3$) δ 7.97 (s, 1H), 7.64 (dd, J=1.5, 8.1 Hz, 1H), 7.65 (td, J=1.8, 7.5 Hz, 1H), 7.57 (d, J=8.4 Hz, 1H), 7.42-7.48 (m, 2H), 7.23-7.28 (m, 1H), 7.02 (t, J=9.9 Hz, 1H), 6.11 (br s, 1H), 4.43 (q, J=3.6, 6.9 Hz, 2H), 4.14 (br s, 1H), 3.16 (s, 1H), 1.43 (t, J=6.9 Hz, 3H); $^{13}$C NMR (300 MHz, CDCl$_3$) δ 165.5, 162.8, 161.8, 158.5, 138.3, 135.5, 135.3, 134.5, 134.3, 134.1, 134.0, 132.3, 132.2, 131.2, 129.4, 129.0, 127.7, 127.5, 124.4, 122.7, 121.9, 116.3, 116.0, 81.3, 79.8, 60.7, 44.8, 14.8; HRMS (ESI-TOF m/z) for C$_{22}$H$_{16}$N$_3$O$_2$F calcd 374.1290, found 374.1299 (M+H)$^+$.

8-Ethynyl-6-(pyridin-2-yl)-4H-benzo[f]imidazo[1,5-a][1,4]diazepine-3-carbaldehyde (11a), Method 1

The reaction was performed following the same procedure for 6a, employing the 2'-pyridyl ethyl ester (HZ-166) 10a (3.0 g, 8.42 mmol) and LiAlH$_4$ (360 mg, 9.27 mmol). This afforded the crude mixture of alcohols (1:0.4 ratio); this mixture of alcohols was used directly in the next step. The mixture of 2'-pyridylalcohols (2.5 g, 8.00 mmol) was dissolved in dry DCM (200 mL) under an argon atmosphere, after which Na$_2$CO$_3$ (2.8 g, 24 mmol) and activated MnO$_2$ (10.5 g, 120 mmol) were added to the reaction mixture at 0° C. The mixture was stirred at room temperature overnight. After 12-14 h, the reaction mixture was diluted with DCM (50 mL) and was filtered through a pad of Celite. The desired aldehyde 11a was purified by flash silica gel chromatography (2:1:1 ethyl acetate/DCM/hexane and 1 mL MeOH+1 mLTEA for 100 mL) to give a white solid 11a (1.02 g, 40% yield for 2 steps); mp 238-240° C. $^1$H NMR (500 MHz, CDCl$_3$) δ 10.05 (s, 1H), 8.56 (d, J=5.0 Hz, 1H), 8.08 (d, J=7.5 Hz, 1H), 7.97 (s, 1H), 7.78 (ddd, J=1.5, 6.0 Hz, 1H), 7.77 (dd, J=1.5, 7.0 Hz, 1H), 7.55-7.57 (m, 2H), 7.38 (ddd, J=1.5, 5.0 Hz, 1H), 6.00 (br s, 1H), 4.17 (br s, 1H), 3.16 (s, 1H): $^{13}$C NMR (75 MHz, CDCl$_3$) δ 186.9, 167.7, 156.2, 148.6, 137.7, 137.1, 136.7, 136.3, 135.4, 135.3, 135.0, 127.1, 124.9, 124.0, 122.8, 121.5, 81.5, 79.7, 44.4 HRMS (ESI-TOF m/z) for C$_{19}$H$_{12}$N$_4$O calcd 113.1080 found 313.1084 (M+H)+.

8-Ethynyl-6-phenyl-4H-benzo[f]imidazo[1,5-a][1,4]diazepine-3-carbaldehyde (11b) Method 2

The aldehyde 11b was prepared according to the method described for pyridine 6b, employing the 2'H 8-ethynyl ethyl ester 10b (4.5 g, 12.6 mmol) and DIBAL-H (22.5 mL of 1.2 M solution in toluene, 20% w/v), to afford the pure compound 11b as a white solid (3.15 g, 80.0%); mp 117-119° C. $^1$H NMR (300 MHz, CDCl$_3$) δ 10.07 (s, 1H), 8.01 (s, 1H), 7.80 (dd, J=1.8, 8.1 Hz, 1H), 7.58-7.62 (m, 2H), 7.46-7.53 (m, 3H), 7.36-7.43 (m, 2H), 5.98 (d, J=12 Hz, H), 4.13 (d, J=12 Hz, 1H). 3.20 (s, 1H). $^{13}$C NMR (75 MHz, CDCl$_3$) δ 186.7, 168.3, 138.8, 138.4, 136.7, 135.3, 135.0, 134.8, 134.1, 130.9, 129.8, 129.2, 128.3, 124.2, 121.1, 81.3, 80.0, 44.2; HRMS (ESI-TOF m/z) for C$_{20}$H$_{13}$N$_3$O calcd 312.0231 found 312.0236 (M+H)+.

8-Ethynyl-6-(2-fluorophenyl)-4H-benzo[f]imidazo[1,5-a][1,4]diazepine-3-carbaldehyde (11c)

The aldehyde 11c was prepared according to the method described for pyridine 6b, employing the 2'F 8-ethynyl ethyl ester 10c (770 mg, 2.06 mmol) and DIBAL-H (4 mL of 1.2 M solution in toluene, 20% w/v), to afford the pure aldehyde 11c as a white solid (530 mg, 78.0%); mp 190-192° C. $^1$H NMR (300 MHz, CDCl$_3$) δ 10.08 (s, 1H), 8.04 (s, 1H), 7.77 (d, J=8.4 Hz, 1H), 7.67 (t, J=7.5 Hz, 1H), 7.60 (d, J=8.4 Hz, 1H), 7.44-7.50 (m, 2H), 7.25-7.30 (m, 1H), 7.04 (t, J=9.0 Hz, 1H), 6.00 (br s, 1H), 4.13 (br s, 1H), 3.18 (s, 1H). $^{13}$C NMR (75 MHz, CDCl$_3$) δ 186.7, 165.7, 161.8, 158.5, 137.8, 136.8, 135.4, 135.2, 134.1, 133.7, 132.5, 132.4, 131.2, 129.2, 127.5, 127.4, 122.6, 122.2, 116.4, 116.1, 81.3, 80.0, 44.2; HRMS (ESI-TOF m/z) for C$_{20}$H$_{12}$FN$_3$O calcd 330.1030 found 330.1037 (M+H)+.

General Synthetic Procedure for oxazole Containing benzimidazodiazepines Through Van Leusen Reaction Via Baldwin's Rules 5-(8-Ethynyl-6-(pyridin-2-yl)-4H-benzo[f]imidazo[1,5-a][1,4]diazepin-3-yl)oxazole (9a)

The 2'-N aldehyde 11a (1.1 g, 3.52 mmol) was placed in a dry two neck round bottom flask and dissolved in dry MeOH (100 mL) under an argon atmosphere. At rt, TosMIC (825 mg, 4.23 mmol) was added as well as K$_2$CO$_3$ (1.30 g, 9.75 mmol) to the reaction mixture and it was allowed to heat reflux for 2 to 3 h. After completion of the reaction on analysis by TLC (silica gel, 1:10 MeOH and EtOAc) which indicated the absence of aldehyde starting material and complete conversion of oxazole of lower R$_f$. The reaction mixture was then quenched with cold water. After this 33% of the solvent was removed under reduced pressure and the work up followed with ethyl acetate (3×30 mL). The combined organic layers were washed with water and brine successively and dried (Na$_2$SO$_4$). The solvent was then removed under reduced pressure and the residue was purified by silica gel flash chromatography to give the pure 2'-N oxazole 9a as a white solid (910 mg, 73.4%); mp: 220-222° C. $^1$H NMR (300 MHz, CDCl$_3$) δ 8.62 (d, J=4.2 Hz, 1H), 8.12 (s, 1H), 8.06 (d, J=7.8 Hz, 1H), 7.96 (s, 1H), 7.85 (ddd, J=1.8, 6.0 Hz, 1H), 7.79 (dd, J=1.8, 6.6 Hz, 1H), 7.62 (d, J=8.4 Hz, 1H), 7.55 (d, J=1.5 Hz, 1H), 7.53 (s, 1H), 7.41 (ddd, J=1.5, 4.8 Hz, 1H), 5.78 (d, J=12.9 Hz, 1H), 4.31 (d, J=12.9 Hz, 1H). $^{13}$C NMR (75 MHz, CDCl$_3$) δ 167.9, 156.7, 149.9, 149.0, 146.6, 137.0, 136.4, 135.8, 135.5, 135.3, 129.8, 127.5, 127.0, 124.9, 124.0, 122.8, 122.7, 121.0, 81.8.7, 79.5, 45.3; HRMS (ESI-TOF m/z) for C$_{21}$H$_{13}$N$_5$O calcd 352.1188, found 352.1193 (M+H)$^+$.

5-(8-Ethynyl-6-phenyl-4H-benzo[f]imidazo[1,5-a][1,4]diazepin-3-yl)oxazole (9b)

The 2'-H oxazole compound 9b was prepared according to the method described for 9a, employing the 2'-H aldehyde 11b (3.30 g, 10.61 mmol), TosMIC, 2.50 g, 12.7 mmol) and K$_2$CO$_3$ (4.3 g, 31.80 mmol). This afforded the crude solid which was purified by flash chromatography (4:1 ethyl acetate/hexane) to give a white solid 9b (2.90 g, 78% yield); mp 120-122° C. $^1$H NMR (300 MHz, CDCl$_3$) δ 8.08 (s, 1H), 7.93 (s, 1H), 7.81 (dd, J=1.8, 6.6 Hz, 1H), 7.81 (d, J=8.4 Hz, 1H), 7.53-7.57 (m, 3H), 7.43-7.49 (m, 2H), 7.39-7.43 (m, 2H), 5.75 (d, J=12.9 Hz, 1H), 4.24 (d, J=12.9 Hz, 1H), 3.18 (s, 1H). $^{13}$C NMR (300 MHz, CDCl$_3$) δ 167.9, 156.7, 149.9, 148.9, 146.6, 137.0, 136.4, 135.8, 135.4, 135.3, 129.8, 127.5, 127.0, 124.9, 124.0, 122.8, 122.6, 121.0, 81.8, 79.5, 45.2; HRMS (ESI-TOF m/z) for $C_{22}H_{14}N_4O$ calcd 351.1246, found 351.1240 (M+H)$^+$.

5-(8-Ethynyl-6-(2-fluorophenyl)-4H-benzo[f]imidazo[1,5-a][1,4]diazepin-3-yl)oxazole (9c)

The 2'-F oxazole 9c was prepared according to the method described for 9a, employing the 2'-N aldehyde 11c (500 mg, 1.51 mmol), TosMIC, 366 mg, 1.82 mmol) and $K_2CO_3$ (629 mg, 4.56 mmol). This afforded the crude solid which was purified by flash chromatography (4:1 ethyl acetate/hexane) to give 2'-F oxazole as a white solid 9b (446 mg, 80% yield); mp 212-214° C. $^1$H NMR (300 MHz, CDCl$_3$) δ 8.03 (s, 1H), 7.93 (s, 1H), 7.75 (d, J=7.8 Hz, 1H), 7.57-7.63 (m, 2H), 7.44-7.53 (m, 3H), 7.23-7.28 (m, 1H), 7.04 (t, J=9.0 Hz, 1H), 5.74 (br s, 1H), 4.26 (br s, 1H), 3.16 (s, 1H). $^{13}$C NMR (300 MHz, CDCl$_3$) δ 165.5, 161.9, 158.5, 149.8, 146.5, 135.4, 135.0, 134.3, 132.3, 131.1, 129.8, 128.9, 127.8, 127.5, 124.5, 122.6, 121.6, 116.4, 116.1, 81.4, 79.6, 45.0; HRMS (ESI-TOF m/z) for $C_{22}H_{13}N_4OF$ calcd 369.1144, found 369.1146 (M+H)$^+$.

5-(8-Ethynyl-6-(pyridin-2-yl)-4H-benzo[f]imidazo[1,5-a][1,4]diazepin-3-yl)-4-methyloxazole (9d)

The 8-ethynyl 2'-N methyl oxazole 9d was prepared according to the method described for 9a, employing 2'-N aldehyde 11a (700 mg, 2.23 mmol), α-methyl TosMIC (560 mg, 2.683 mmol) and $K_2CO_3$ (925 mg, 6.709 mmol). This afforded the crude oxazole which was purified by flash silica gel chromatography EtOAc/DCM (1:1 and 1 mL MeOH+1 mLTEA for 100 mL) to give 8-ethynyl 2'-N methyl oxazole 9d as a half white solid (600 mg, 74% yield); mp 209-211° C. $^1$H NMR (500 MHz, CDCl$_3$) δ 8.60 (d, J=4.5 Hz, 1H), 8.04 (d, J=7.5 Hz, 1H), 7.98 (s, 1H), 7.86 (s, 1H), 7.81 (t, J=7.5 Hz, 1H), 7.76 (dd, J=1.5, 8.5 Hz, 1H), 7.57 (d, J=8.5 Hz, 1H), 7.54 (d, J=1.0 Hz, 1H), 7.37 (t, J=7.5 Hz, 1H), 5.70 (d, J=12.0 Hz, 1H), 4.28 (d, J=12.5 Hz, 1H), 3.16 (s, 1H), 2.53 (s, 3H); $^{13}$C NMR (75 MHz, CDCl$_3$) δ 167.6, 156.7, 148.8, 148.7, 140.7, 136.8, 136.2, 135.9, 135.3, 134.8, 132.8, 129.8, 128.2, 126.9, 124.7, 123.9, 122.7, 120.7, 81.8, 79.2, 45.3, 12.3; HRMS (ESI-TOF m/z) for $C_{22}H_{15}N_5O$ calcd 366.1340 found 366.1349 (M+H)$^+$.

5-(8-Ethynyl-6-phenyl-4H-benzo[f]imidazo[1,5-a][1,4]diazepin-3-yl)-4-methyloxazole (9e)

The 8-ethynyl 2'-H methyl oxazole 9e was prepared according to the method described for 9a, employing the 2'-H aldehyde 11b (250 mg, 0.803 mmol), α-methyl TosMIC (201 mg, 0.967 mmol) and $K_2CO_3$ (332 mg, 2.4 mmol). This afforded the crude solid which was purified by flash chromatography (4:1 ethyl acetate/hexane) to give half white 8-ethynyl 2'-H methyl oxazole as a solid 9e (242 mg, 82% yield); mp 228-230° C. (300 MHz, CDCl$_3$) δ 8.01 (s, 1H), 7.85 (s, 1H), 7.77 (dd, J=1.8, 8.4 Hz, 1H), 7.56-7.60 (m, 2H), 7.49-7.53 (m, 2H), 7.37-7.46 (m, 3H), 5.67 (d, J=12.9 Hz, 1H), 4.20 (d, J=12.9 Hz, 1H), 3.17 (s, 1H), 2053 (s, 3H); $^{13}$C NMR (300 MHz, CDCl$_3$) δ 168.5, 148.7, 140.6, 139.5, 135.9, 135.8, 135.3, 134.5, 132.8, 130.5, 130.3, 129.3, 128.3, 128.2, 128.0, 122.6, 121.0, 81.5, 79.6, 45.3, 12.3; HRMS (ESI-TOF m/z) for $C_{23}H_{16}N_4O$ calcd 365.1400 found 365.1397 (M+H)$^+$.

5-(8-Ethynyl-6-(2-fluorophenyl)-4H-benzo[f]imidazo[1,5-a][1,4]diazepin-3-yl)-4-methyloxazole (9f)

The 8-ethynyl 2'-F methyl oxazole 9f was prepared according to the method described for 9a, employing the 8-ethynyl 2'-F aldehyde 11c (500 mg, 1.52 mmol), α-methyl TosMIC (381 mg, 1.82 mmol) and $K_2CO_3$ (630 mg, 4.55 mmol). This afforded the crude solid which was purified by flash chromatography (4:1 ethyl acetate/hexane) to give a half white 8-ethynyl 2'-F methyl oxazole as a solid 9f (450 mg, 78% yield); mp 145-147° C.; $^1$H NMR (300 MHz, CDCl$_3$) δ 8.03 (s, 1H), 7.84 (s, 1H), 7.74 (d, J=7.8 Hz, 1H), 7.55-7.65 (m, 2H), 7.46 (s, 2H), 7.22-7.28 (m, 1H), 7.03 (t, J=8.1 Hz, 1H), 5.70 (br s, 1H), 4.25 (br s, 1H), 3.16 (s, 1H), 2.53 (s, 3H). $^{13}$C NMR (75 MHz, CDCl$_3$) δ 165.4, 161.9, 158.5, 148.7, 140.6, 135.4, 134.6, 134.2, 132.8, 132.2, 132.1, 131.2, 131.1, 129.9, 128.9, 128.3, 127.9, 127.8, 124.5, 124.4, 122.5, 121.4, 116.4, 116.1, 81.5, 79.9, 45.1, 12.3; HRMS (ESI-TOF m/z) for $C_{23}H_{15}N_4OF$ calcd 383.1300 found 383.1303 (M+H)$^+$.

Example 7

In Vitro Analysis

FLIPR Binding

The FLIPR functional assay is used to determine the $EC_{50}$ at the α1 and α3 $GABA_A$ receptor subtypes. A high $EC_{50}$ for the α1 subtype would indicate a low chance of adverse effects, including sedation, ataxia, and muscle relaxation. A low α3 $EC_{50}$ would indicate potential effectiveness as an anxiolytic, antihyperalgesic, and likely an anticonvulsant. See, for example, Liu et al. (*Assay. Drug. Dev. Technol.* 2008, 6, 781-6) and Joesch et al. (*J. Biomol. Screen.* 2008, 13, 218-28).

Compounds tested were synthesized internally and solubilized in DMSO at a 10 mM concentration. GABA was purchase from Sigma (#A2129) and prepared at 100 mM in water.

HEK-293 cells were stably transfected with the α1, β3, γ2 GABA A receptor subunits (GenBank accession numbers NM_000806.3, NM_000814.5, and NM_198904.1, respectively) or α3, β3, γ2 (NM_000808 for α3) where obtained from ChanTest Co. (Catalog # CT6216 and CT6218, respectively).

Cells were cultivated in Dulbeco's Modified Eagle's Medium (DMEM, Sigma D5796) supplemented with 10% Fetal Bovine Serum (FBS, Gibco 16000), 0.5 mg/mL Geneticin (Gibco), 0.04 mg/mL Hygromycin B (Gibco), 0.1 mg/mL Zeocin (Gibco) and 20 mM HEPES (Sigma). Cells were grown at 37° C. in a humidified atmosphere of 5% $CO_2$. In the experiments described here frozen cells were used. For this purpose, cells were gown and maintained under confluency during 2-3 weeks and then frozen down at different cell densities using Recovery™ Cell Culture Freezing Medium (Gibco).

18 hours prior to the experiment, cells were quickly thawed at 37° C. and seeded on Poly-D-Lys 384 plates (Corning 356663) at a density of 25,000 cells/well and in 25 μL of complete cell medium as described above.

Membrane potential changes induced by the flux of ions through the receptor were measured as relative fluorescence units (RFU) using the Fluorometric Imaging Plate Reader (FLIPR Tetra®, Molecular Devices) and the FLIPR Membrane Potential Blue Assay kit (Molecular Devices). Prior to the addition of the compounds the medium was removed and cells were loaded with 20 μL of dye prepared in assay buffer composed of Hank's Balanced Salt Solution (HBSS with $Ca^{+2}$ and $Mg^{+2}$; Gibco 14025) with 20 mM Hepes. After 1 hour of incubation at room temperature (RT), the plate was placed into the FLIPR instrument and experiments were run adding first 10 µL from the $1^{st}$ addition plate (compound plate) and after a 3 minutes incubation adding 20 µL of the $2^{nd}$ addition or agonist plate. The response to this last GABA addition was monitored for another 3 minutes.

$1^{st}$ addition plates or compound plates. First addition plates containing the compounds to be tested were prepared as follows: compounds in 10 mM dimethyl sulfoxide (DMSO) stock were serially diluted from column 3 to 12 and 13 to 22 in 100% DMSO using Corning 3657 plates and a Tecan Freedom Evo® platform. Then, compounds were further diluted 1:100 in assay buffer. A GABA $EC_0$ (assay buffer alone) and $EC_{100}$ (150 or 100 µM final GABA concentration after $1^{st}$ addition for α1 or α3-containing receptor cell lines, respectively) were also included in these plates and used as minimum and maximum response controls, respectively, to analyse any possible compound agonist response.

$2^{nd}$ addition plate or agonist plate. Second addition plates were generated using a GABA $EC_{20}$ to test potentiation profile of the compounds. $EC_{20}$ and $EC_{100}$ GABA (final assay concentrations) were used as minimum and maximum response controls, respectively. $EC_{20}$ was 2 or 1.2 µM final GABA concentration for α1 or α3-containing receptor cell lines, respectively.

Data Analysis. The difference between the maximum and the minimum (Max-Min) fluorescence reached during the first addition or read interval and the second read interval were used for data analysis (agonist and potentiation, respectively). Data was normalized according to the following formula:

$$\% \text{ activation} = 100 \times \left( \frac{\text{Test well} - \text{Median } EC0 \text{ or } 20 \text{ Control}}{\text{Median } EC100 \text{ Control} - \text{Median } EC0 \text{ or } EC20 \text{ Control}} \right)$$

wherein "Test well" refers to those that contain test compounds.

$EC_{50}$ and maximum stimulation values were determined from concentration-response curves at 10 distinct concentrations. The four-parameter logistic model was used to fit each data set.

All compounds (HZ-166, MP-III-085, MP-III-080, KRM-II-81, KRM-II-82, KRM-II-18B, KRM-II-97, KRM-II-73, and SH-I-085) displayed a α1 $EC_{50}$ above 20 µM (the highest concentration tested) while also exhibiting 3 activity, with $EC_{50}$ in, or near, the nanomolar range (TABLE 3).

Liver Microsomal Stability Studies

In vitro liver microsomal studies were completed to measure the stability of the compounds against degradation in various species' liver microsomes.

Compound was incubated in hepatic microsomes over a 30-minute incubation period at 37° C. Incubations both with and without NADPH (2 mM) were performed in a 96-well plate format. The reaction was initiated with the addition of substrate and was terminated by protein precipitation. All incubations were performed using a final substrate concentration of 4 µM in 50 mM sodium phosphate buffer, pH 7.4. The final organic solvent content was 0.5% acetonitrile and 0.02% DMSO. The amount of enzyme present was fixed at 1.11 mg/mL protein irrespective of the species of microsomes used. Samples were analyzed by LC/MS-MS to determine the percent loss in the NAPDH incubations relative to the NADPH free incubations.

Although HZ-166 and other BZDs had been shown to be stable against human liver microsomes, short half lives in in vivo studies indicated poor stability in rodents, which can be a hindrance in fully evaluating compounds in preclinical studies in rodents. Results are shown in TABLE 3.

TABLE 3

Compound binding affinities (α1 and α3) and liver microsomal stability.

| Compound | α1 Binding $EC_{50}$ (µM) | α3 Binding $EC_{50}$ (µM) | Human | Dog | Mouse | Rat |
|---|---|---|---|---|---|---|
| | | | Liver microsome stability (reported in % remaining) Conditions: 37° C., 4 µM compound, 30 minutes | | | |
| HZ-166 | >20 | 0.844 | 80 | 97 | 54 | 50 |
| MP-III-085 | >20 | 5.15 | 81 | 93 | 85 | 93 |
| MP-III-080 | >20 | 3.02 | 91 | 97 | 92 | 94 |
| KRM-II-81 | >20 | 0.937 | 91 | 94 | 90 | 90 |
| KRM-II-82 | >20 | 0.0321 | 74 | 86 | 73 | 72 |
| KRM-II-18B | >20 | 0.0112 | 78 | 87 | 79 | 68 |
| KRM-II-97 | >20 | 0.629 | 94 | 85 | 86 | 75 |
| KRM-II-73 | >20 | 0.115 | 78 | 89 | 70 | 77 |
| SH-I-085 | >20 | 0.0249 | 62 | 77 | 67 | 61 |

Example 8

Motor Impairment

Inverted Screen

The inverted screen test is used to measure whether or not a test compound induces muscle relaxation. When a test subject is placed on a wire screen which is then inverted, the reaction is to climb to the opposite side so they are no longer hanging upside down. If a compound promotes muscle relaxation, the test subjects will either fall off, or hang onto the screen without being able to climb to the opposite side.

Male Sprague-Dawley rats (n=5) were dosed i.p. (vehicle=1% carboxymethyl cellulose) with diazepam (3, 10, or 30 mg/kg), KRM-II-81 (10, 30, or 60 mg/kg) or HZ-166 (30 mg/kg) 30 minutes prior to testing. Rats were placed onto the top of a wire screen, which was then inverted so that the rats were hanging upside down. Rats were observed for 60 seconds, at which point they were score (0=climbed over; 1=hanging onto screen; 2=fell off). Results were analyzed using ANOVA (Dunnett's test: *$P<0.05$).

Figure 4:
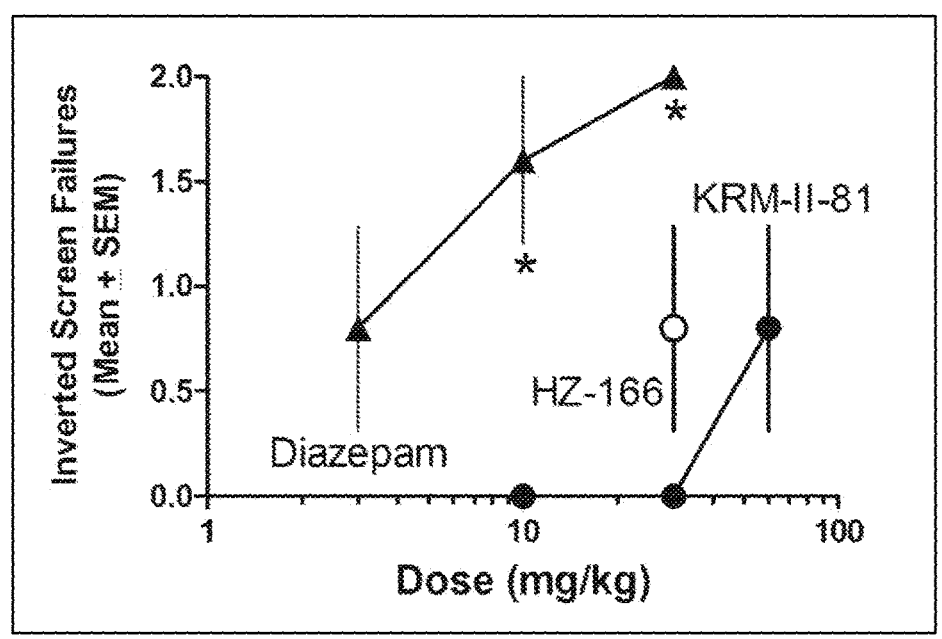
FIG. 4 is a graph of dose versus inverted screen failures for KRM-II-81, HZ-166, and diazepam in the inverted screen assay. Male Sprague-Dawley rats (n=5) were dosed i.p. (vehicle=1% carboxymethyl cellulose) with diazepam (3, 10, or 30 mg/kg), KRM-II-81 (10, 30, or 60 mg/kg), or HZ-166 (30 mg/kg) 30 minutes prior to testing. Results were analyzed using ANOVA (Dunnett's test: *P<0.05).
Figure 5A:
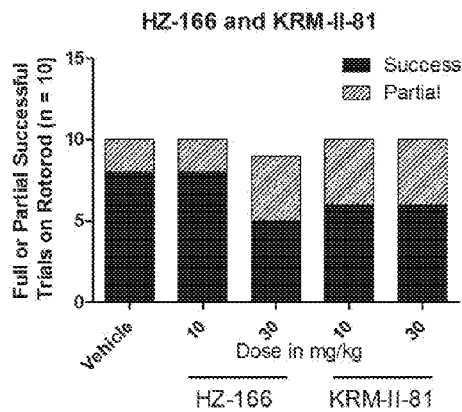
FIG. 5 are graphs showing results from the rotorod assay for A) HZ-166 and KRM-II-81; B) MP-III-085, KRM-II-82 and KRM-II-18B; C) MP-III-080 and KRM-III-78; D) KRM-III-59; E) KRM-III-66 and KRM-III-65; F) KRM-III-79 and KRM-III-67. Male NIH Swiss mice (n=10) were dosed i.p. with vehicle (1% carboxymethyl cellulose) or one of the test compounds (10 or 30 mg/kg) 30 minutes prior to being tested on the rotorod. Mice were placed on a rod for two minutes at 4 revolutions per minute. Mice that did not fall were designated a "Success", while mice that fell once during the timing were given a "Partial" designation. Mice that fell twice failed the testing.
Figure 5B:
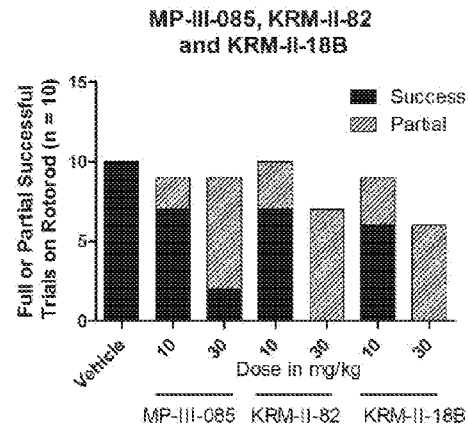
Figure 5C:
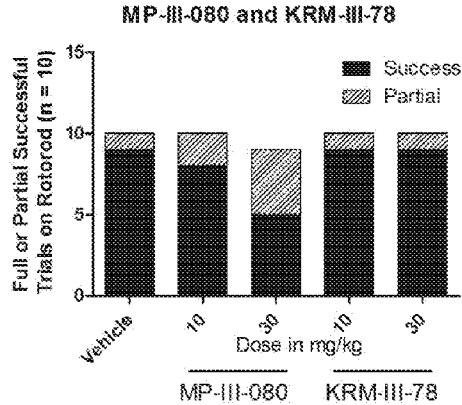
Figure 5D:
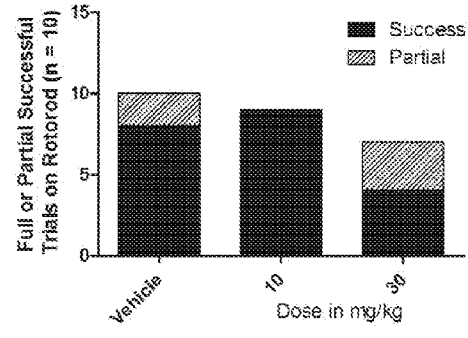
Figure 5E:
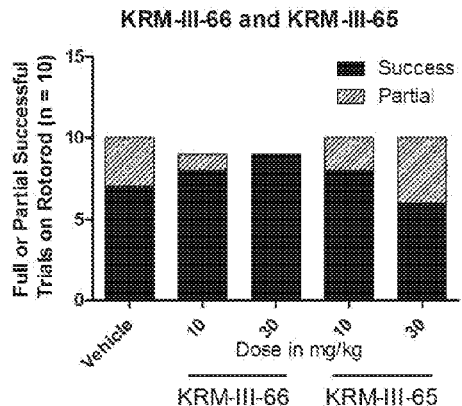
Figure 5F:
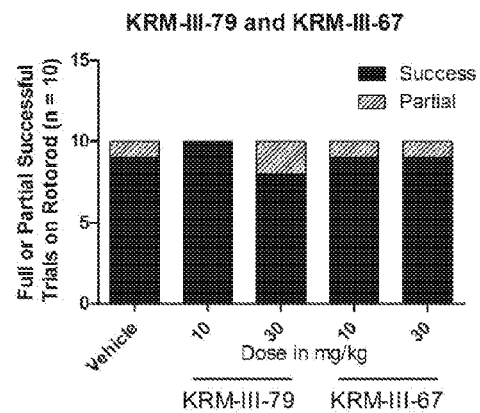

Neither HZ-166 nor KRM-II-81 induced significant muscle relaxation (FIG. 4); however, signs of muscle relaxation began to appear at 30 mg/kg for HZ-166, while the same slight signs occurred at 60 mg/kg for KRM-II-81. Non-dosed rats were able to climb to the top of the screen when inverted (score of 0.4±0.4). Diazepam but not KRM-II-81 or HZ-166 produced full motor impairment.

Rotorod

The rotorod assay (FIG. 5) is used to determine the ataxic effects, generally stemming from the α1 subtype, that compounds have in test subjects. Mice are trained to run on a slow, rotating cylinder for two minutes, and failure to stay on the rod may be due to ataxia. HZ-166 has previously been shown to have no ataxic complications in doses over 100 mg/kg. Each set of compounds were tested against a vehicle.

Male NIH Swiss mice (n=10/group) were trained on a rotorod (Ugo Basile 7650) at 4 r.p.m. for two minutes per training session prior to testing. On test day, mice were dosed i.p. with either vehicle (1% carboxymethyl cellulose)

or one of the test compounds (10 or 30 mg/kg) 30 minutes prior to testing. Once placed on the rotorod, mice were observed for falling. Mice that did not fall off during testing were given a "success" designation, while mice that fell off once during the 2 minutes of testing were scored as "partial." Mice that fell twice failed the trial.

The majority of compounds tested well at 10 mg/kg, while KRM-II-82, KRM-II-18B, and KRM-III-69 failed multiple times at 30 mg/kg.

KRM-II-81 still appeared to be the best compound in rotarod assays as it exhibited no significant ataxic concerns (rotarod) without observed signs of sedation.

Example 9

Anticonvulsant Activity

Maximal Electroshock (MES)-Induced Convulsion Protection

The maximal electroshock (MES) assay is designed to determine how well a test compound can prevent seizures induced by applying a voltage stimuli to a mouse. HZ-166 has previously been shown to be effective in this assay, as well as giving protection against scMET-induced seizures.

Male CD (n=10) were pretreated i.p. with vehicle (1% carboxymethyl cellulose), KRM-II-81 (3, 10, 30 mg/kg), or HZ-166 (3, 10, 30 mg/kg). Mice were subjected to electrical induced tonic seizures and examined for anticonvulsant effects 30 minutes after treatment. Mice were then given a 7 mA electroshock using a Wahlquist Model H for 0.2 seconds and observed for the presence or absence of seizure activity. Each mouse is tested only once and euthanized immediately following the test.

Figure 6:
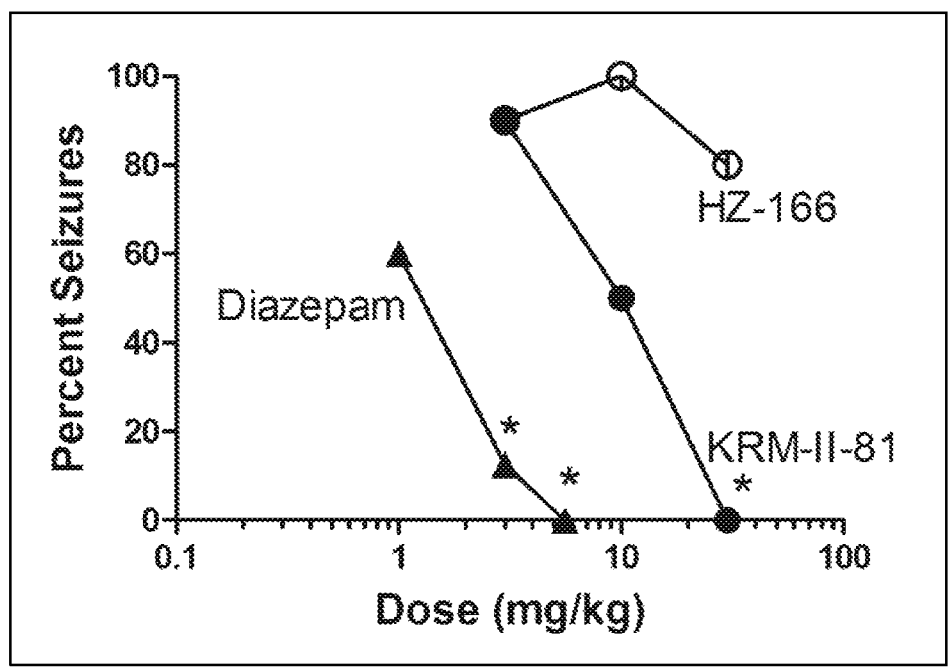
FIG. 6 is a graph of dose versus percent seizures, showing protection from MET-induced seizures by KRM-II-81, HZ-166, and diazepam. Male CD-1 mice (n=10) were dosed i.p. 30 minutes prior to being tested. Results were analyzed using ANOVA (Dunnett's test versus vehicle: *P<0.05).

KRM-II-81 is shown to display greater effectiveness than HZ-166 (FIG. 6). Both diazepam and KRM-II-81 fully protected against seizure induction, whereas HZ-166 (up to 60 mg/kg) did not.

scMET-Induced Seizure Protection

Figure 7:
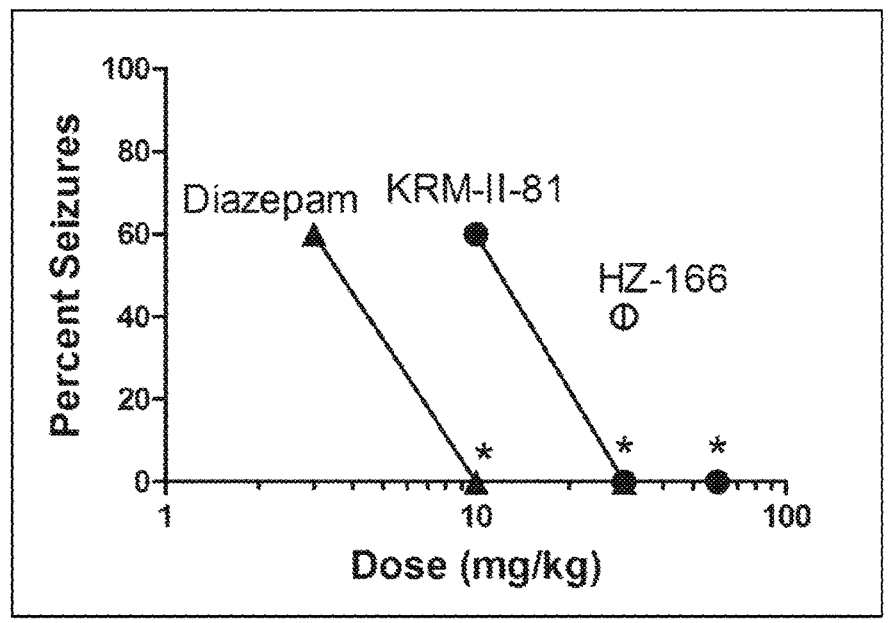
FIG. 7 is a graph of dose versus percent seizures, showing protection against scMET by KRM-II-81, HZ-166, and diazepam. Male Sprague-Dawley rats (n=5) were dosed i.p. with KRM-II-81, HZ-166, or diazepam 30 minutes prior to testing. A 35 mg/kg subcutaneous dose of pentylenetetrazole was given and the percent outcome of seizure was recorded. Results were analyzed using ANOVA (Dunnett's test: *P <0.05).

A subcutaneous (sc) injection of pentylenetetrazol (PTZ), also known as metrazole (MET), is known to induce clonic and tonic seizures, demonstrated by loss of righting (inability to orient itself in an upright position). Test subjects were given a test compound, followed by a 35 mg/kg dose of MET and observed for convulsions (FIG. 7).

Male Sprague-Dawley rats (n=5) were dosed i.p. (vehicle=1% carboxymethyl cellulose) with either diazepam (3 or 10 mg/kg), KRM-II-81 (10, 30 or 60 mg/kg), or HZ-166 (30 mg/kg) 30 minutes prior to testing. Pentylenetetrazole (in saline) was dosed at 35 mg/kg i.p., and rats were observed for 30 minutes for signs of seizures. Results were analyzed using ANOVA (Dunnett's test: *P<0.05).

Mice were then dosed i.p. with 5, 10, 25, or 50 mg/kg of KRM-II-81. 30 minutes later, a subcutaneous dose of pentylenetetrazole was administered, and the mice were observed for seizures. KRM-II-81 performed very well (TABLE 4), protecting most mice, with an $ED_{50}$ of 10.94 mg/kg at the half hour time point.

Diazepam achieved significant protection at 10 mg/kg, KRM-II-81 at 30 mg/kg, while previously shown anticonvulsant HZ-166 had little effect at 30 mg/kg. This indicates that KRM-II-81 has greater therapeutic potential against convulsions than HZ-166.

TABLE 4

Assessment of KRM-II-81 in the scMET test for anticonvulsant activity.*

| | Dose (mg/kg) | | | |
|---|---|---|---|---|
| | 5 | 10 | 25 | 50 |
| Protected | 0/8 | 5/8 | 7/8 | 8/8 |

*$ED_{50}$ = 10.94 mg/kg

PTZ-Induced Seizure Threshold

Following the evaluation of protection against scMET (35 mg/kg), KRM-II-81, HZ-166, and diazepam were tested to determine at what threshold of scMET each compound can protect against seizures at various concentrations. After a pretreatment of test compound, MET was intravenously administered to a test subject until a convulsions were observed.

Male Sprague-Dawley rats (n=8; from Harlan Sprague Dawley, Indianapolis, Ind.) were dosed i.p. (vehicle=1% carboxymethyl cellulose) with diazepam (0.1, 0.3, or 1 mg/kg) or a test compound (3, 10, 30, or 60 mg/kg) 30 minutes prior to testing. Pentylenetetrazole was administered i.v. to each group (10 mg/mL at 0.5 mL/minute) until each animal exhibited a clonic convulsion, or for four minutes. Each animal was used only once and was euthanized post testing. Results were analyzed using ANOVA (Dunnett's test: *P<0.05).

Figure 8:
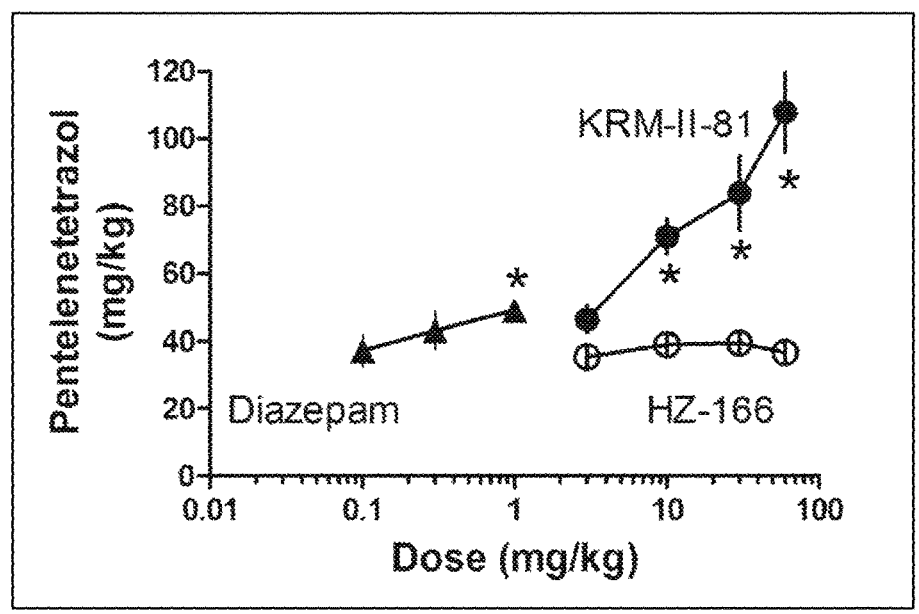
FIG. 8 is a graph of dose versus pentylenetetrazole (scMet), showing the threshold against scMET seizures by KRM-II-81, HZ-166, and diazepam. Male Sprague-Dawley rats (n=8) were dosed i.p. with KRM-II-81 or HZ-166 (3, 10, 30, or 60 mg/kg) or diazepam (0.1, 0.3, or 1 mg/kg) 30 minutes prior to infusion of PTZ until a convulsion is achieved. Results were analyzed using ANOVA (Dunnett's test: *P<0.05).
Figure 9A:
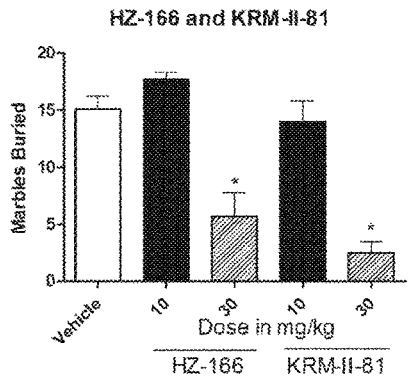
FIG. 9 are graphs showing the number of marbles buried for each dose of compound in the marble burying assay for A) HZ-166 and KRM-II-81; B) MP-III-085, KRM-II-82 and KRM-II-18B; C) MP-III-080 and KRM-III-78; D) KRM-III-59; E) KRM-III-66 and KRM-III-65; F) KRM-III-79 and KRM-III-67. Male NIH Swiss mice (n=10) were dosed i.p. with vehicle (1% carboxymethyl cellulose) or one of the test compounds (10 or 30 mg/kg) 30 minutes prior to being tested in the marble burying assay. Results were analyzed using ANOVA (Dunnett's test: *P<0.05). $^{a}$Sedation-like effects were observed at 30 mg/kg. $^{b}$Sedation-like effects were observed at 10 and 30 mg/kg. $^{c}$Modest sedation-like effects were observed at 30 mg/kg.
Figure 9B:
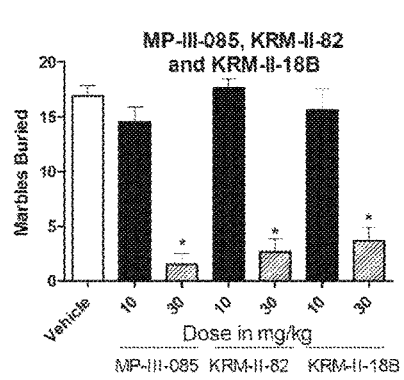
Figure 9C:
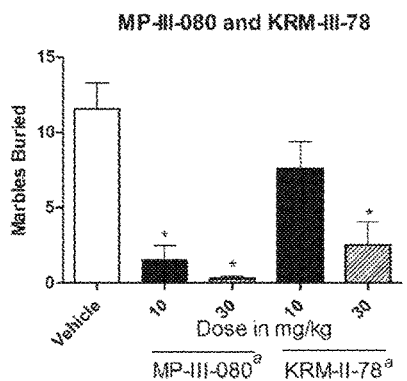
Figure 9D:
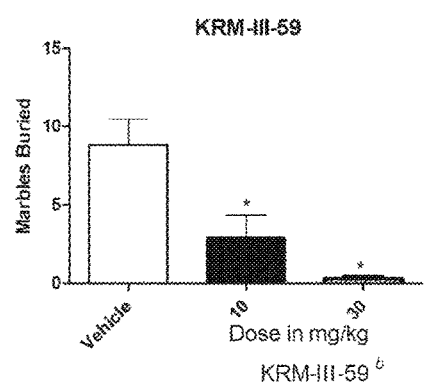
Figure 9E:
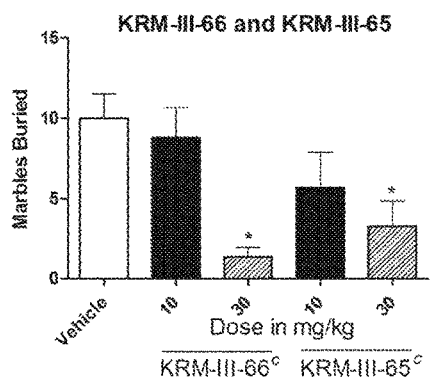
Figure 9F:
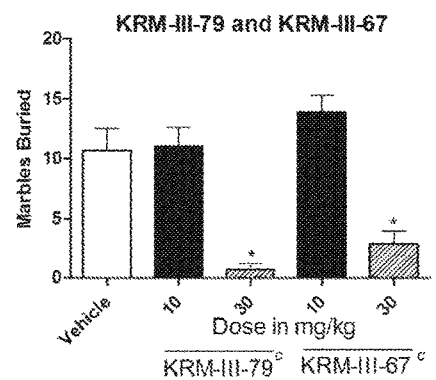

HZ-166 displayed little protection against MET (35 mg/kg) at concentrations varying from 3 mg/kg to 60 mg/kg, while KRM-II-81 began to exhibit a significant protection against seizures, requiring a 71 mg/kg dose of MET when pretreated with 10 mg/kg of KRM-II-81 (FIG. 8). Both diazepam and KRM-II-81 significantly increased the seizure threshold to PTZ with KRM-II-81 producing larger maximal effect.

Example 10

Anxiolytic Activity

Anxiolytic Marble Burying Assay

The marble burying assay is used to determine the anxiolytic activity of a given compound. Mice are placed in a tub containing 20 marbles placed over a bed of sawdust. Defensive burying (Broekkamp 1986) is the natural reaction for the mice. When given an anxiolytic, such as diazepam, the mice are less likely to defensively bury the marbles.

Experiments were carried out by the methods described in Li et al. (Life Sciences 2006, 78, 1933-1939). Separate groups of mice were used in these experiments and were conducted in a dimly lit testing room. After 60 min acclimation to the experimental room, mice were placed in a 17×28×12 cm high plastic tub with 5 mm sawdust shavings (Harlan Sani-Chips, Harlan-Teklad, Indianapolis, Ind., USA) on the floor, which was covered with 20 blue marbles (1.5 cm diameter) placed in the center. Mice were left in the tub for 30 min. The number of marbles buried (⅔ covered with sawdust) was counted and submitted to inter-observer reliability assessment.

All compounds are shown to display a significant reduction in marbles buried at 30 mg/kg (FIG. 9), while MP-III-080 and KRM-III-69 show a reduction at 10 mg/kg. However, sedation was also observed in these three compounds, which likely led to the reduction in marble burying (both at 10 and 30 mg/kg) for MP-III-080, and KRM-III-69.

KRM-II-81 still appeared to be the best compound in the marble burying assay as it had good activity in the marble burying without observed signs of sedation.

Vogel Conflict Model for Anxiety

The Vogel conflict procedure is used to determine the anxiolytic effects a compound exerts on a test subject, and HZ-166 has previously been shown to be effective in rhesus monkeys. Subjects are withheld from water prior to testing. Once given water during testing, they will either be unpunished, where they are free to drink without consequence, or punished, where a small electrical shock is applied after every $20^{th}$ lick. In vehicle punished, is it is expected that the rats hesitate from drinking due to the anxiousness of being shocked. When given an anxiolytic, the mice will continue to drink water despite the electrical shock.

Experiments were conducted as described in the protocol of Alt et al. (*Neuropharmacology* 2007, 52, 1482-1487). Experimentally-naive adult male Sprague-Dawley rats (Harlan Industries, Indianapolis, Ind.), weighing between 200 and 300 g, were used as subjects. The rats were housed in Plexiglas cages (4 per cage) and given free access to Lab Diet #5001 for rodents (PMI Nutrition International Inc., St. Louis, Mo.). Water was withheld for 20-24 hours prior to the first training session. A 12-hr light/dark cycle was maintained, and all experimental sessions were conducted during the light phase of the cycle at about the same time each day. All experiments were conducted in accordance with the NIH regulations of animal care covered in "Principles of Laboratory Animal Care", NIH publication 85-23, and were approved by the Institutional Animal Care and Use Committee.

Apparatus. The experiments were conducted using operant behavior test chambers ENV-007 (Med Associates Inc., Georgia, Vt., USA), 30.5×24.1×29.2 cm. The test chambers were contained within light and sound attenuating shells. On the front wall of the chamber, a food trough was mounted 2 cm off the grid floor on the centerline. Two response levers were centered 8 cm off the centerline and 7 cm off the grid floor. Three lights were located above each response lever at 15 cm off the grid floor. Responding on the levers was without consequences for all sessions. On the rear of the chamber, a sipping tube was mounted 3 cm off the grid floor and 3 cm from the door. The sipping tube was wrapped with electrical tape to prevent the circuit from being completed if the animals were holding/touching the tube. All events were controlled and licking data was recorded by a Compaq computer running MED-PC Version IV (Med Associates Inc., Georgia, Vt., USA).

Sipper tube training. Rats were put into the chamber on day 1 and 2 with white noise and the houselight illuminated, and allowed to drink for a total of six minutes after the first lick was made. The six minutes was broken into two components, the first three minutes was recorded as the unpunished component and the second three minutes were recorded as the punished component. During the two training days no shock was delivered in the punished component. After training, animals were returned to the home cage and given access to water for 30 minutes. For the second and third tests for each group, water was withheld for 24 hours before the training session. Animals were re-trained for one day. After training, animals were returned to the home cage and given access to water for 30 minutes.

Sipper tube testing. On day 3, animals were weighed and injected with either vehicle or compound and returned to the home cage. Thirty minutes after injection, animals were placed into the test chamber. The session was identical to the training session except that during the punishment component the sipper tube delivered a brief electrical shock (100 milliseconds, 0.5 mA) after every $20^{th}$ lick (FR20).

Data Analysis. The mean number of licks for both the unpunished and punished components were analyzed. In addition, data were also expressed as a percent of control values. The calculation was done using the mean number of licks for the control group in both components. Individual animal means (percent control) were calculated for animals receiving drug utilizing the formula: number of licks divided by mean number of licks by control group times 100 for each respective component. Dose-effect functions were analyzed by ANOVA followed by post-hoc Dunnett's test with vehicle treatment as the control standard. The proportion of animals exhibiting specified numbers of responses was analyzed by Fisher's exact probability test comparing vehicle control to drug values. Statistical probabilities ≤0.05 were considered significant.

Figure 10:
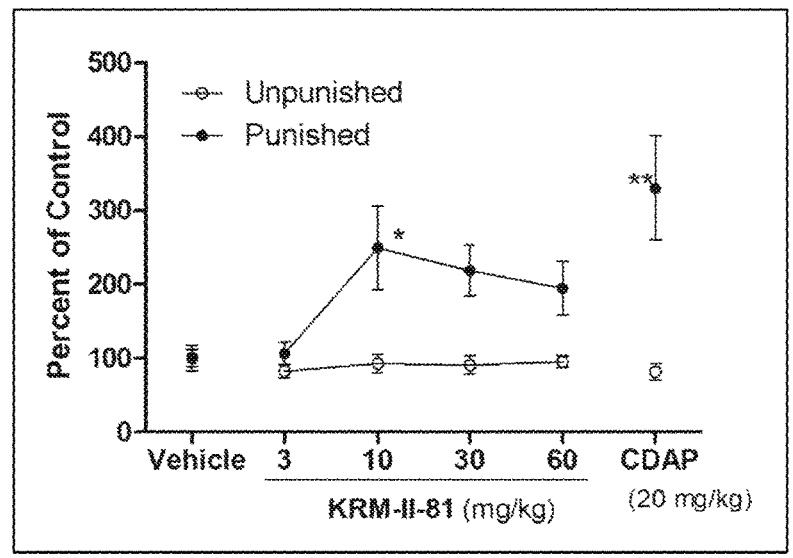
FIG. 10 is a graph of the concentration of KRM-II-81 versus percent of control for KRM-II-81 analyzed in the Vogel conflict procedure. After a baseline was established using a vehicle (1% 2-hydroxyethyl cellulose), male Sprague-Dawley rats (n=6-8) were dosed i.p. with either KRM-II-81 (3, 10, 30, or 60 mg/kg) or chlordiazepoxide (20 mg/kg) 30 minutes prior to testing. Results were analyzed using ANOVA (Dunnett's test: *P<0.05; Student t-test: **P<0.05).

As shown in FIG. 10, KRM-II-81 exhibited a significant increase in punished licking as compared to control at 10 mg/kg, indicating a powerful anxiolytic effect. Chordiazepoxide was run as a positive control. Both the anxioltyic, chlordiazepoxide, and KRM-II-81 increased punished licking.

Example 11

Antihyperalgesic Activity

Tactile Hypersensitivity in Spinal Nerve Ligated (SNL) Rats

The von Frey filament test is used to test for antihyperalgesia, or an increased sensitivity to pain. HZ-166 has been shown to perform well in this assay. The von Frey filaments are used to apply pressure to the forelimbs of test subjects at set amounts. When pressure becomes too great, the forelimb is withdrawn and the amount of force applied recorded. The spinal nerve ligation induced hyperalgesia, reducing the amount of force a limb can take before being withdrawn.

Test compounds were given to test the effectiveness of combating the hyperalgesic effect of SNL. Male Sprague-Dawley rats went through SNL at least 90 days prior to the von Frey testing. Rats were first tested without given an injection to determine a baseline. Following baseline establishment, rats (n=5 for all groups) were dosed i.p. with vehicle (1% carboxymethyl cellulose), KRM-II-81 (30 mg/kg), or gabapentin (50 mg/kg). Subjects were then tested every hour for four hours to determine the antihyperalgesic effect of the test compounds. For testing, pressure using von Frey filaments was applied to the forelimb of the rat. Pressure was increased until the limb was withdrawn, and the amount of pressure was recorded.

Figure 11:
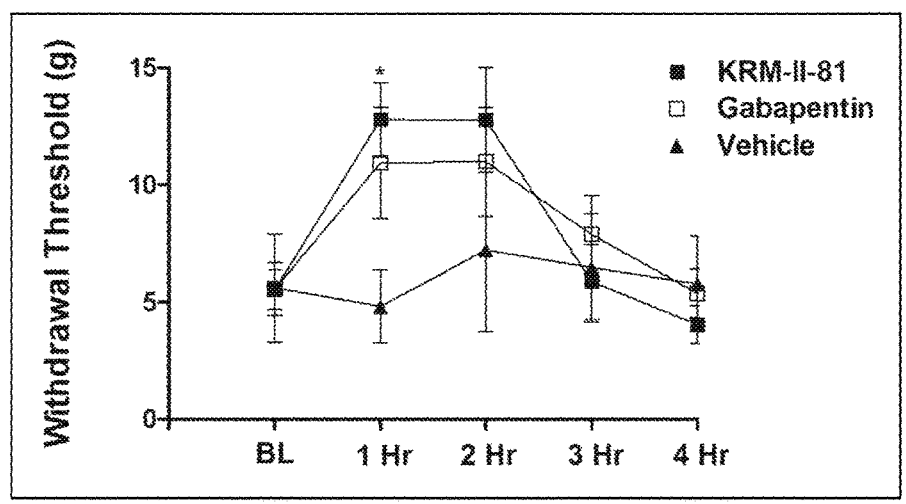
FIG. 11 is a graph of time versus withdrawal threshold for KRM-II-81, Gabapentin, and vehicle, showing the effect of KRM-II-81 on antihyperalgesia in the von Frey filament assay. Male Sprague-Dawley rats (n=5) were dosed i.p. either vehicle, KRM-II-81 (30 mg/kg), or gabapentin (50 mg/kg) and tested in the von Frey filament assay after undergoing SNL 90 days prior. Results were analyzed using ANOVA (Dunnett's test: *P<0.05).

In FIG. 11, rats given vehicle were only able to withstand an average of 5-6 grams of force before the forelimb is withdrawn. Both gabapentin (50 mg/kg) and KRM-II-81 (30 mg/kg) were active as antihyperalgesics, increasing the amount of force that can be handled before forelimb withdrawal. However, KRM-II-81 (at one hour) was able to reach significance, while gabapentin was not. This indicates that KRM-II-81 is a potential therapeutic for the treatment for neuropathic pain. With vehicle, rats were able to withstand ~5 g. of force before removing paw. KRM and gabapentin increase this pain threshold to ~12 g. of force from 1-2 hours, with KRM slightly more effective (doses unknown). The results indicate that KRM-II-81 was able to reverse the effects of hyperalgesia, allowing rats to withstand more force in the von Frey filament test after SNL surgery.

Example 12

GABA-A Receptor PAM

Model of Pain

Complete Freund's adjuvant (CFA) contains *Mycobacterium butyricum*, inducing inflammation and an increase in paw thickness. 0.1 mL of CFA was injected in the right hind paw of Sprague Dawley male rats under isoflurane anaesthesia.

Food-maintained operant responding (rate response). Rats (n=7) were placed in a chamber consisting of two (one active) levers. Rats were trained to press a lever (left) for a food pellet under a multiple-cycle procedure. Each cycle started with a 15 min inactive period (dark chamber and no programmed consequence), followed by a 5 min active period (cue light above the active lever lit up). The active period was set on a FR10 schedule and rats could receive a maximum of 5 food pellets. The cue light was terminated either after 5 minutes or once 5 food pellets were delivered. After each active period (every 20 minutes), rats received the next dose of drug for a duration of 2 hours. Data (rate per minute) was collected using Graphic State 3.03 software and interface (Coulbourn Instruments Inc.)

Mechanical hyperalgesia. Mechanical hyperalgesia was measured 3 days after CFA treatment. Rats (n=6) were placed in elevated boxes with a mesh floor. Von Frey filaments (expressed in g) were applied perpendicularly to the hindpaws, starting with the lowest filament (1.4 g) then increased until hindpaw withdrawal was observed. After each measurement, rats received the next dose of drug (every 20 min) until the maximum threshold (26 g) was observed. For the antagonist study, rats were pretreated with the benzodiazepine site antagonist flumazenil (10 min) and then received the next dose of drug (every 20 min) until the pre-CFA threshold was observed.

Horizontal wire test. Rats (n=10) were lifted by the tail and allowed to grasp a horizontally strung wire with their forepaws and released. The inability to complete this task (within 3 seconds) was recorded 20 minutes after each injection of drug.

Drugs. The following drugs were used: HZ166, KRM-II-18B, and KRM-II-81, and were dissolved in a mixture containing 20% Dimethyl sulfoxide (DMSO), 10% Emulphor-620 (Rhodia Inc.), and 70% of 0.9% saline. Flumazenil (purchased from Cayman Chemical Company, MI) was dissolved in a mixture containing 10% ethanol, 40% propylene glycol, and 50% sterile water. Midazolam (Akorn, Inc.) was dissolved in 0.9% saline. Doses were expressed as the weight of the drug in milligrams per kilogram of body weight and drugs were administered intraperitoneally.

Figure 12:
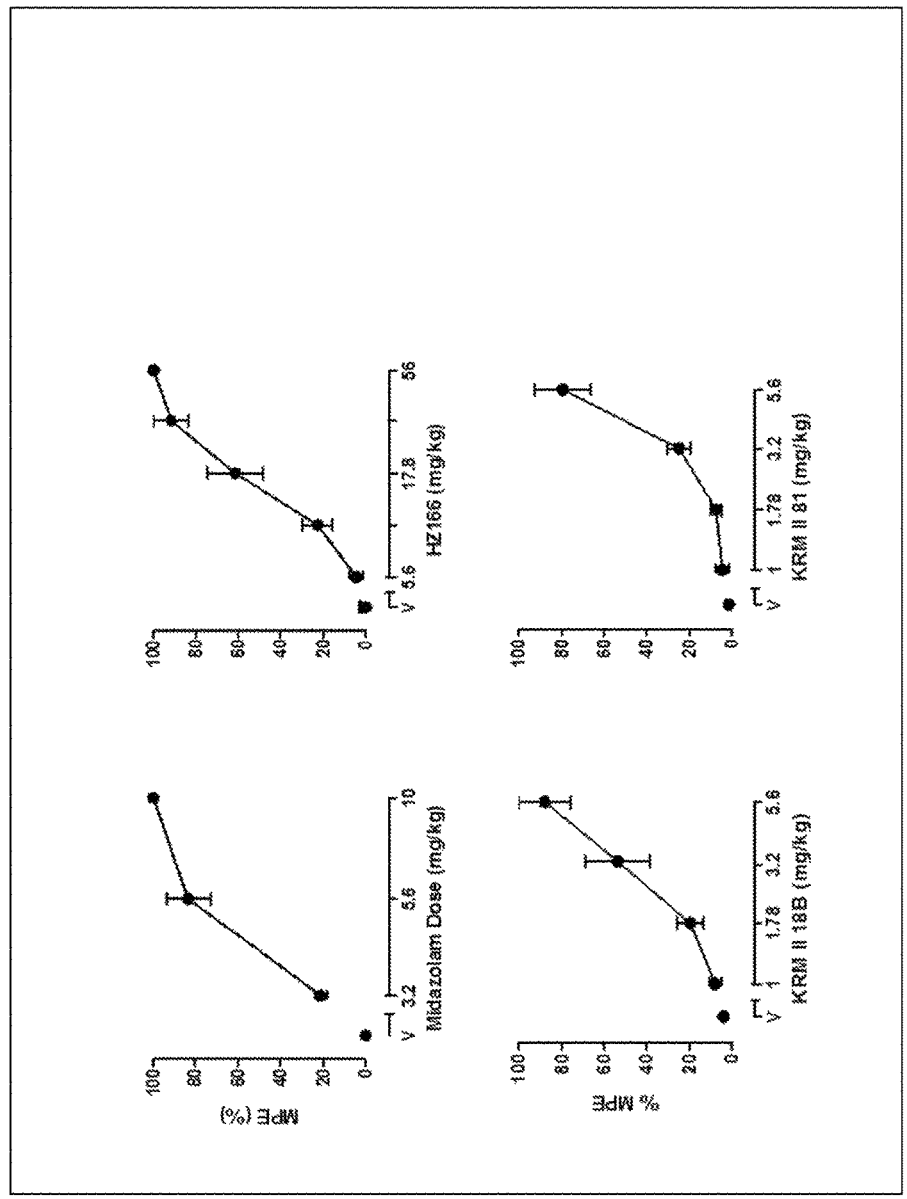
FIG. 12 are graphs of compound concentration versus % MPE, showing that $GABA_A$ receptor PAMs, Midazolam (nonselective PAM), HZ 166, KRM-II-18B, and KRM-II-81 dose-dependently attenuated mechanical hyperalgesia in a CFA-induced inflammatory pain rat model. Raw data (paw withdrawal threshold, expressed in g of von Frey filament) was converted to a maximal possible effect value according the following equation.

Results. Results are shown in FIG. 12, FIG. 13, and FIG. 14. This data demonstrated that KRM-II-81 and KRM-II-18B are much more active against hyperalgesia in the von Frey filament assay and on par with the performance of midazolam.

Example 13

Pharmacokinetics and Concentrations in Brain of KRM-II-81 Administered to Rats by IV and IP The single-dose pharmacokinetics were determined in femoral artery/vein cannulated Sprague-Dawley rats. The rats received a 1 mg/kg intravenous and 10 mg/kg oral gavage dose of compound. Blood samples were collected at 0.08 (IV only), 0.25, 0.5, 1, 2, 4, 8, 12, and 24 hours after initiation of compound administration. Plasma was obtained via centrifugation. Plasma samples were then analyzed by LC-MS, and pharmacokinetic parameters calculated using Watson (version 7.4; Thermo Fisher Scientific). Calculated parameters include clearance (Cl), volume of distribution (Vdss), area-under-the-curve (AUC), half-life (T½), maximum plasma concentration (Cmax), time of maximum concentration (Tmax), and bioavailability (% F).

Male Sprague-Dawley rats were given either a 1 mg/kg oral dose or 10 mg/kg i.p. dose. Plasma concentrations were taken at 0.08, 0.25, 0.5, 1.0, 2, 4, 8, 12, and 24 hours (three rats per time point for each dose). The time-plasma concentration profiles are shown in FIG. 15.

Following a 1 mg/kg IV dose in rat, KRM-II-81 had a mean clearance of 21.7 mL/min/kg with a mean Vdss of 1.4 L/kg and a mean T ½ of 1.4 hours. Following a 10 mg/kg IP dose in rat, the mean AUC was 16500 nM*hrs with a Cmax of 3090 nM occurring at 2.0 hours. The mean IP T ½ was 3.1 hours and the mean bioavailability was 69%. The 1 hour brain concentration following a 10 mg/kg IP dose was 6630 nM with a Kp, uu of 0.53. The 4 hour brain concentration was 2050 nM with a Kp, uu of 0.67.

Example 14

Forced Swim Test

The forced swim test is used as a primary screen for the antidepressant nature of a test compound. Mice are placed in a cylinder filled with a small amount of water. Mice that are more mobile after a dosing of a compound are determined to be less depressed.

The experiment was carried out as described by Porsolt et al. (*Arch. Int. Pharmacodyn. Ther.* 1977, 229, 327-366). Male NIH Swiss mice (n=7-8) were dosed i.p. with vehicle (1% HEC, 0.25% Tween 80, 0.05% antifoam), KRM-II-81 (3, 10, or 30 mg/kg), or imipramine (15 mg/kg) and assessed in the forced swim test. Mice were placed individually in clear plastic cylinders (10 cm in diameter×25 cm in height) filled to 6 cm with 22-25° C. water for 6 minutes. The duration of immobility was recorded during the last 4 minutes of a 6-minute trial. A mouse was regarded as immobile when floating motionless or making only those movements necessary to keep its head above the water.

Results are shown in FIG. 16. Results were analyzed using ANOVA (Dunnett's test *P<0.05). KRM-II-81 demonstrated antidepressant effects at 10 and 30 mg/kg. Imipramine was used as a positive control.

All patents, publications and references cited herein are hereby fully incorporated by reference. In case of conflict between the present disclosure and incorporated patents, publications, and references, the present disclosure should control.

The invention claimed is:
1. A compound of formula (I):

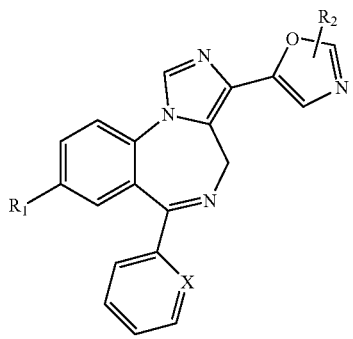
(I)

or a salt thereof, wherein:
X is selected from the group consisting of N, C—H, C—F, C—Cl, C—Br, C—I, and C—NO$_2$;
R$_1$ is selected from the group consisting of —C≡CH, —C≡C—Si(CH$_3$)$_3$, -cyclopropyl, bicycle[1.1.1]pentane

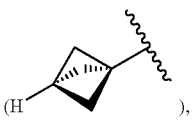

and —Br; and
R$_2$ is selected from the group consisting of —H, —CH$_3$, —CH$_2$CH$_3$ and —CH(CH$_3$)$_2$,
with the proviso that the compound is not

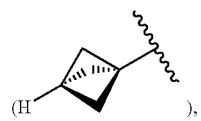

2. A compound of formula (II):

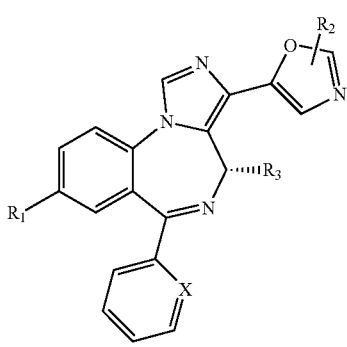
(II)

or a salt thereof, wherein:
X is selected from the group consisting of N, C—H, C—F, C—Cl, C—Br, C—I, and C—NO$_2$;
R$_1$ is selected from the group consisting of —C≡CH, —C≡C—Si(CH$_3$)$_3$, -cyclopropyl, bicycle[1.1.1]pentane

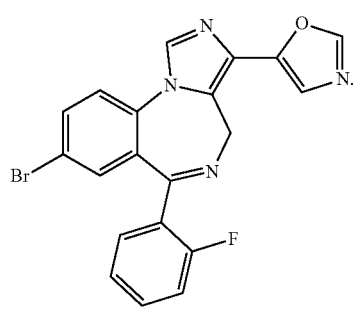 [SMILES: Fc1ccccc1C1=NCc2c(-c3cnco3)ncn2-c2ccc(Br)cc21]

and —Br;
R$_2$ is selected from the group consisting of —H, —CH$_3$, —CH$_2$CH$_3$, and —CH(CH$_3$)$_2$; and
R$_3$ is selected from the group consisting of —CH$_3$, —CH$_2$CH$_3$, —CH(CH$_3$)$_2$, —F, —Cl, —CF$_3$, and —CCl$_3$.

3. A compound of formula (III):

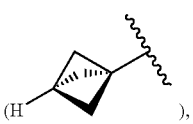
(III)

or a salt thereof, wherein:
X is selected from the group consisting of N, C—H, C—F, C—Cl, C—Br, C—I, and C—NO$_2$;
R$_1$ is selected from the group consisting of —C≡CH, —C≡C—Si(CH$_3$)$_3$, -cyclopropyl, bicycle[1.1.1]pentane

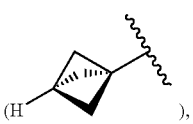

and —Br;
R$_2$ is selected from the group consisting of —H, —CH$_3$, —CH$_2$CH$_3$, and —CH(CH$_3$)$_2$; and
R$_3$ is selected from the group consisting of —CH$_3$, —CH$_2$CH$_3$, —CH(CH$_3$)$_2$, —F, —Cl, —CF$_3$, and —CCl$_3$.

4. The compound of claim 1, or a salt thereof, wherein R$_1$ is —C≡CH or Br; and X is N, C—H, C—F, or C—Cl.

5. The compound of claim 1, or a salt thereof, wherein the compound has the following formula:

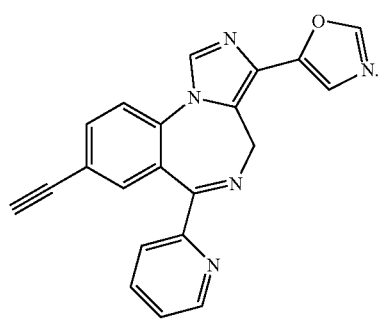 [SMILES: C#Cc1ccc2c(c1)C(c1ccccn1)=NCc1c(-c3cnco3)ncn1-2]
6. The compound of claim 1, or a salt thereof, wherein $R_2$ is —H.
7. The compound of claim 1, selected from the group consisting of:
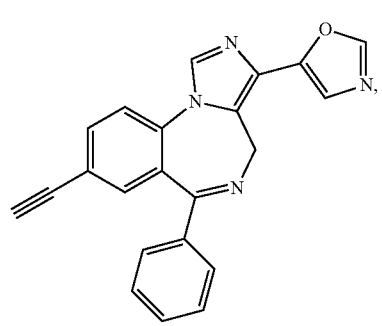
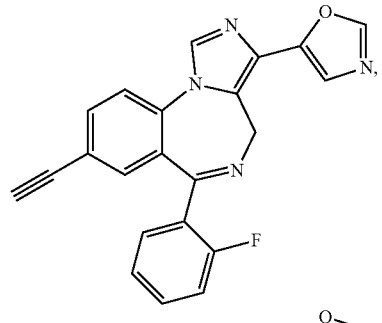
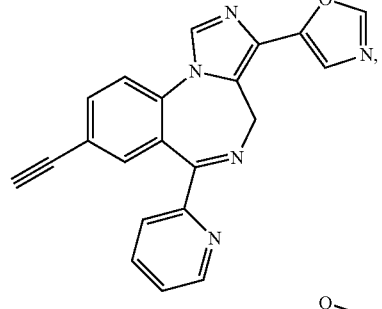
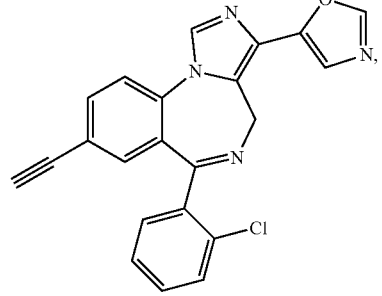
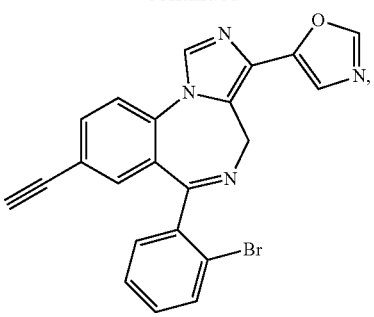
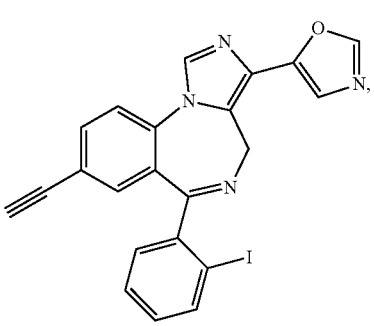
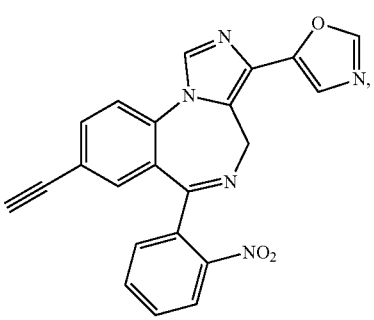
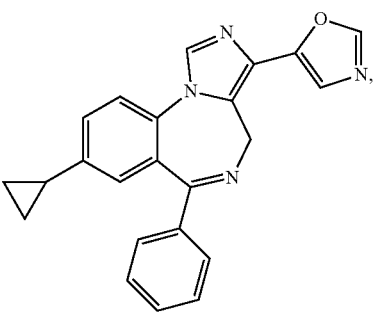
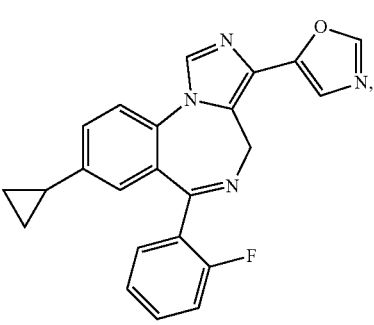

85
-continued
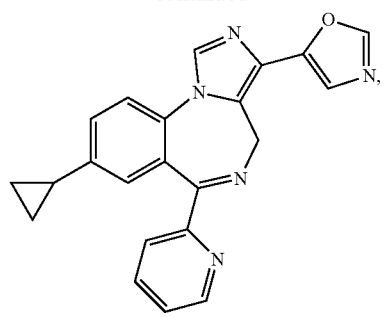
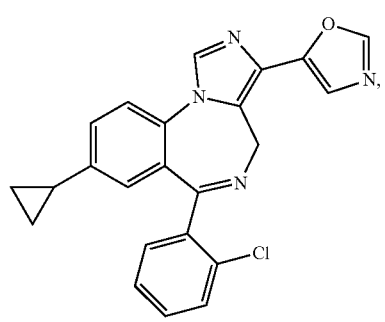
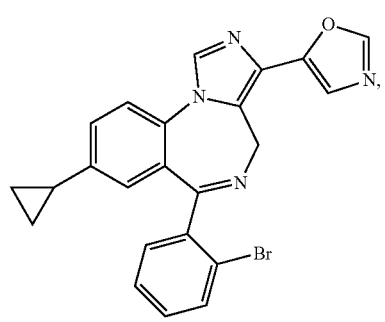
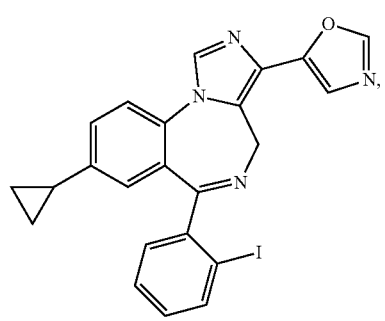
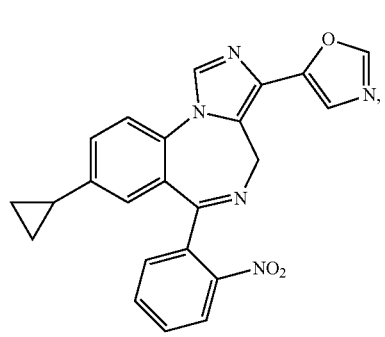
86
-continued
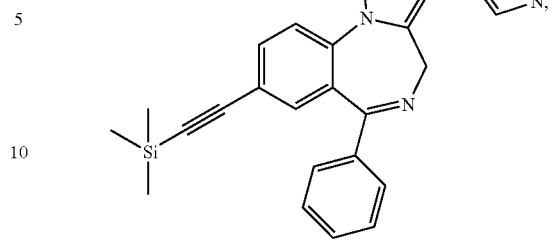
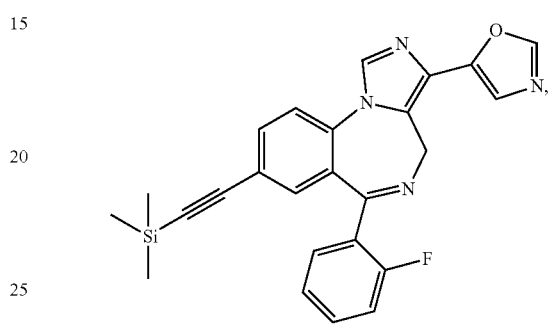
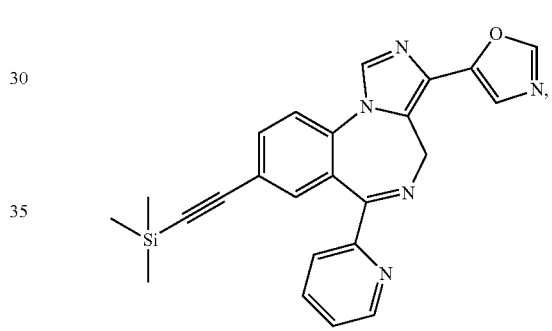
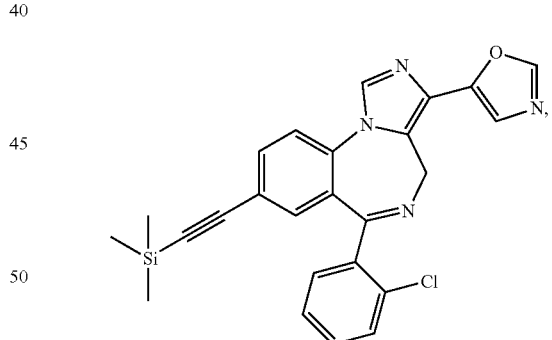
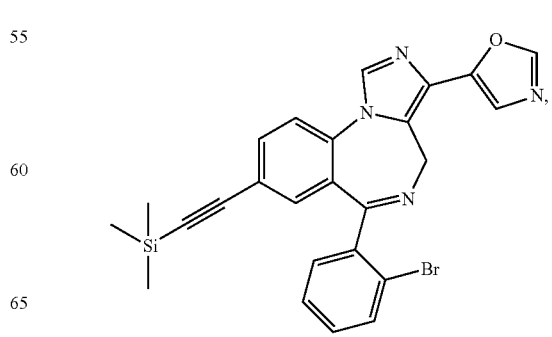

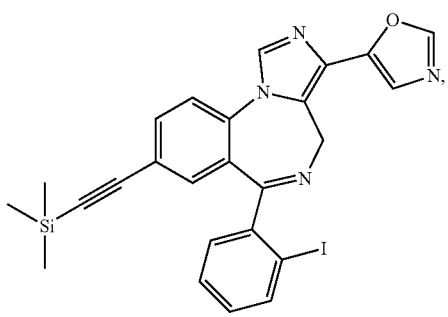
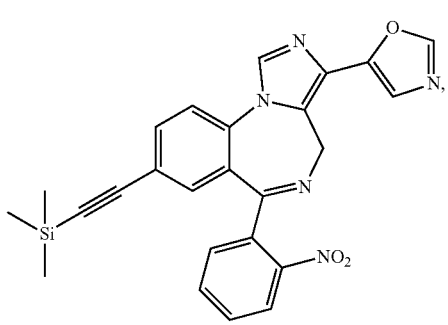
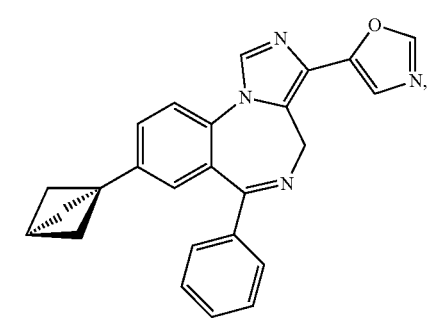
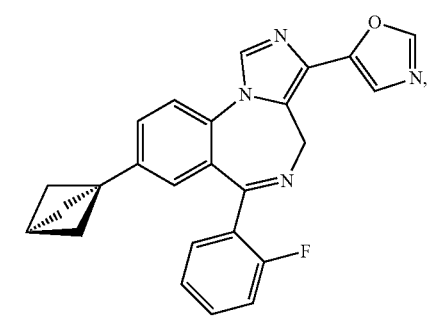
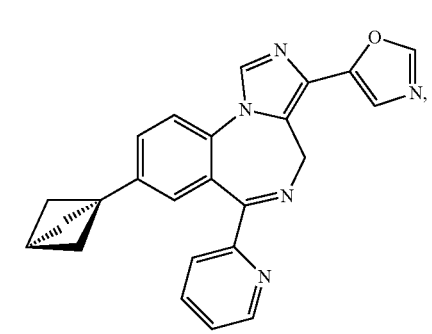
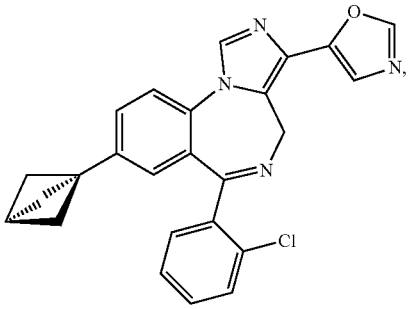
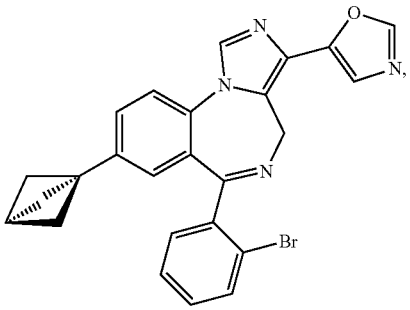
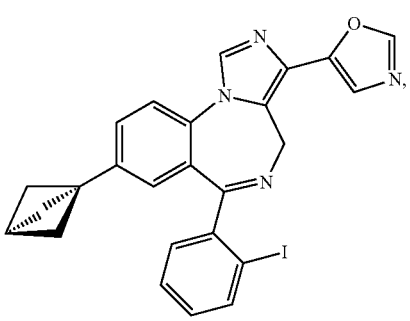
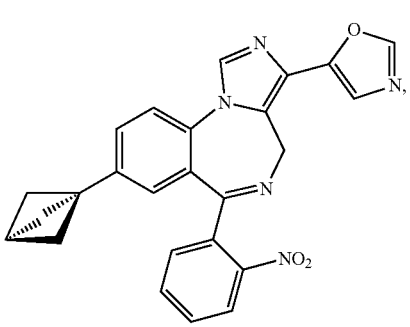
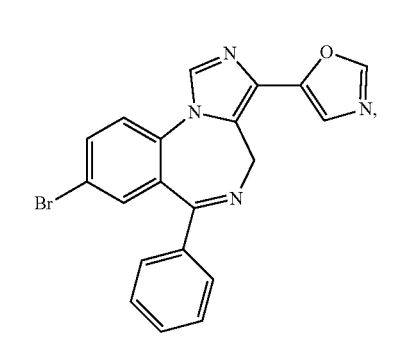

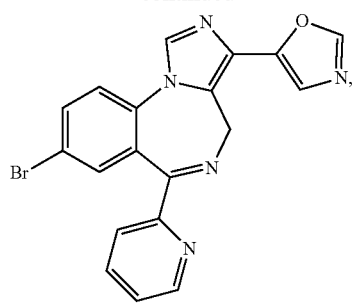
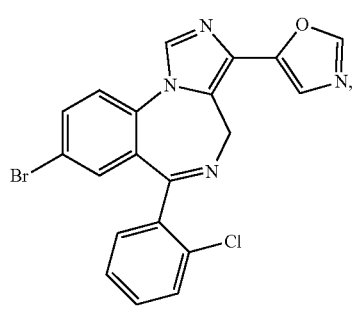
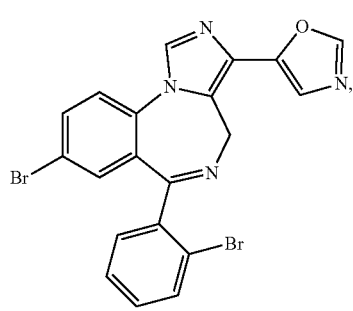
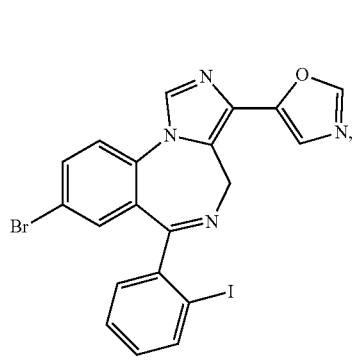
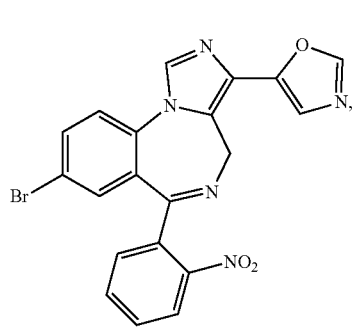
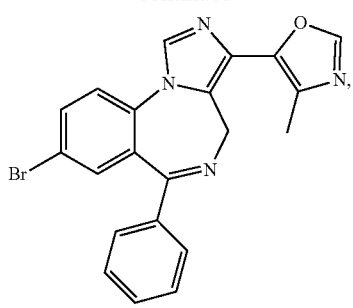
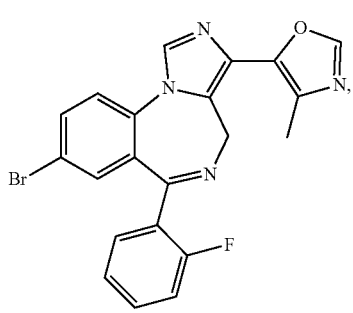
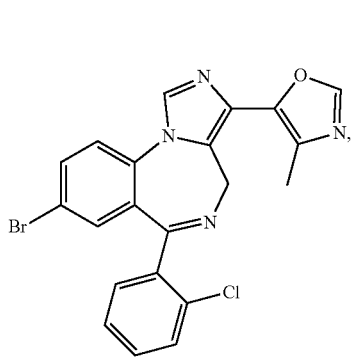
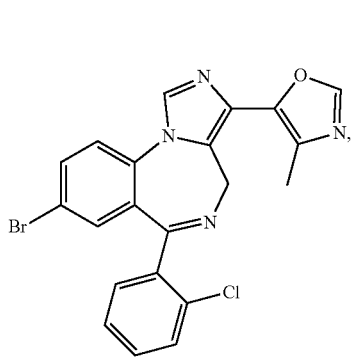
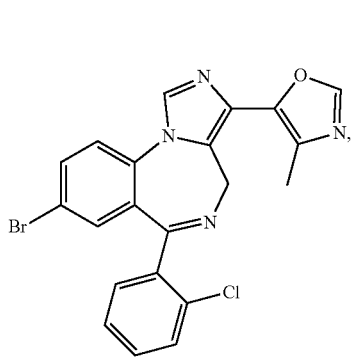

-continued

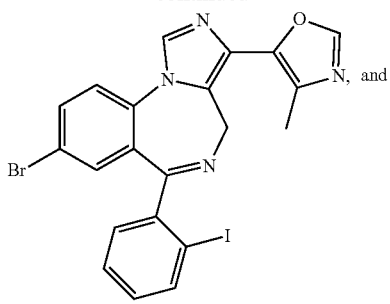, and

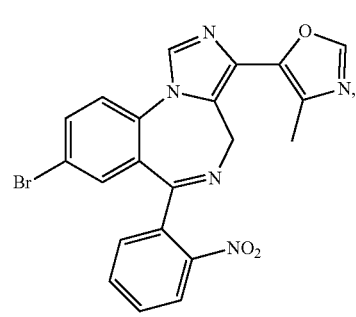 [SMILES: Cc1ncoc1-c1ncn2c1CN=C(c1ccccc1[N+](=O)[O-])c1cc(Br)ccc1-2], or a salt of any thereof.

8. A pharmaceutical composition comprising a compound according to claim 1 or a salt thereof; and a carrier.

9. A method of treating a disorder selected from an anxiety disorder, depression, epilepsy, schizophrenia and neuropathic pain in a subject in need of treatment, comprising administering to the subject an effective amount of a compound according to claim 1, or a salt thereof.

10. The compound of claim 1 selected from the group consisting of:

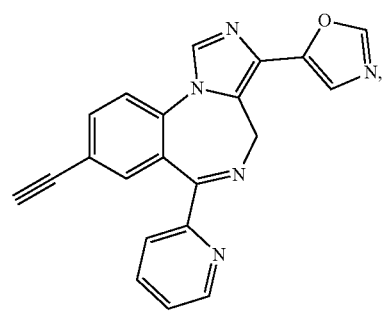,

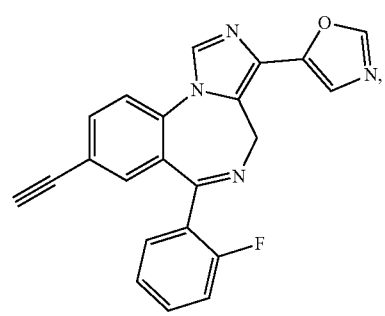,

-continued

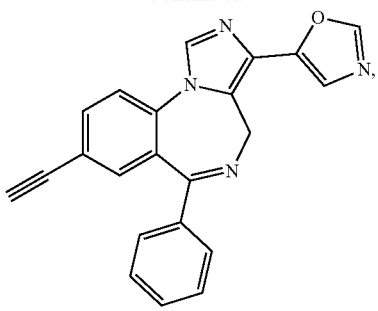,

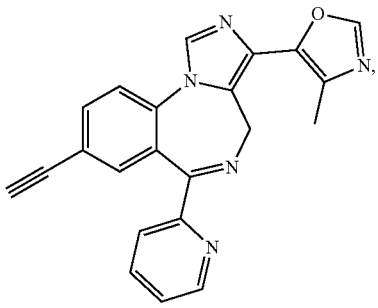,

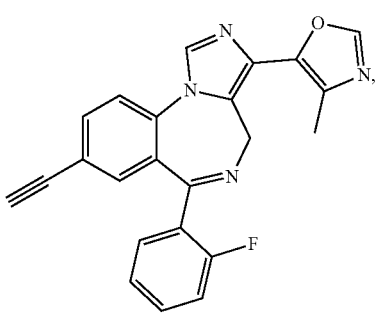,

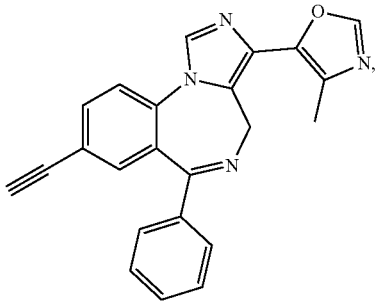,

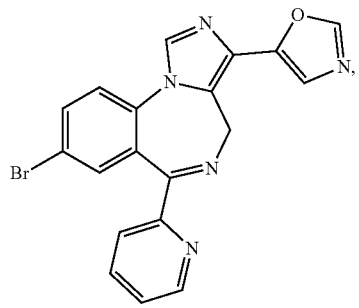,

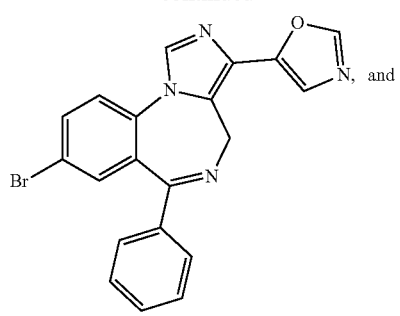
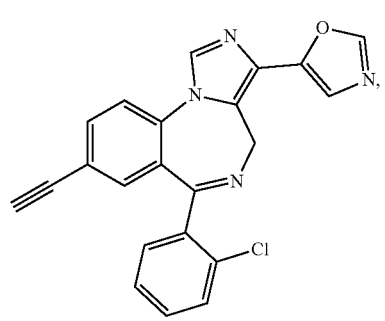
or a salt thereof.
11. The compound of claim 2, or a salt thereof, wherein R$_1$ is —C≡CH or Br; and X is N, C—H, C—F, or C—Cl.
12. The compound of claim 2, or a salt thereof, wherein R$_2$ is —H.
13. The compound of claim 2, selected from the group consisting of:
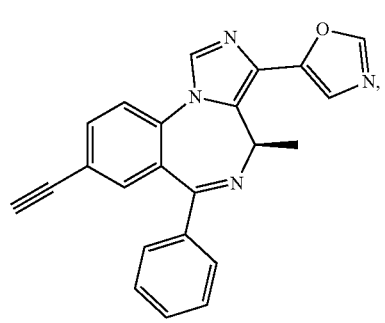
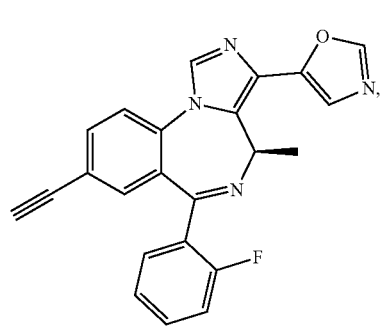
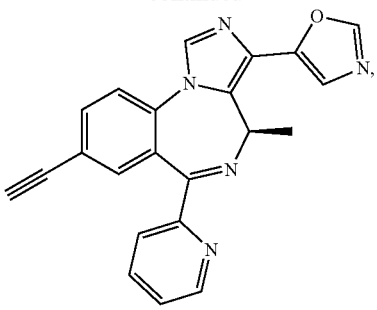
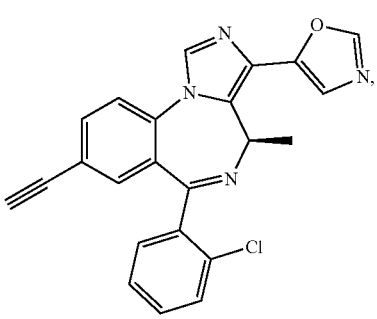
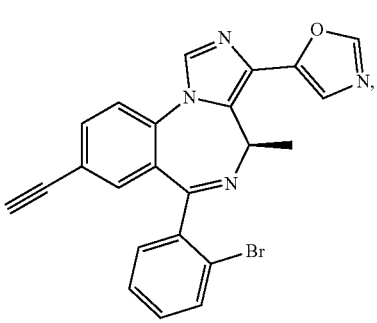
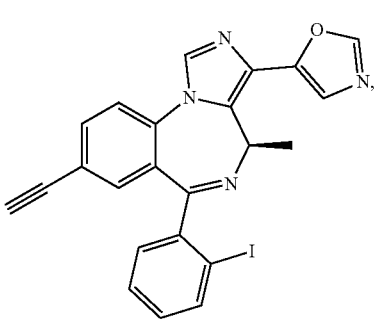
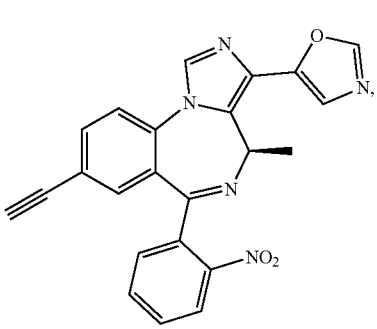

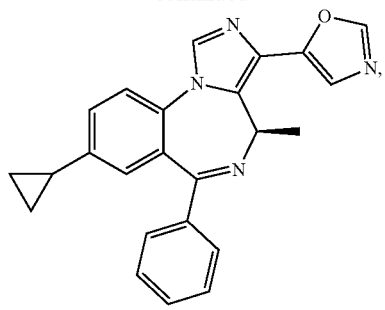
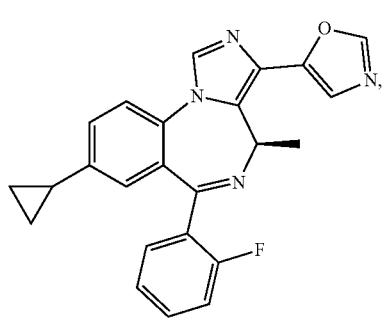
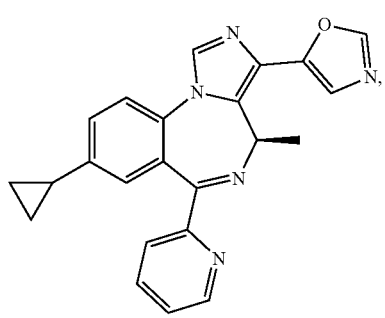
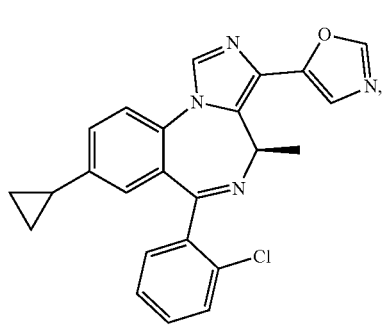
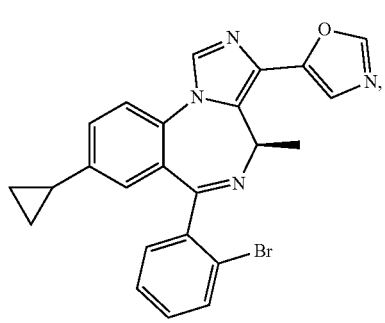
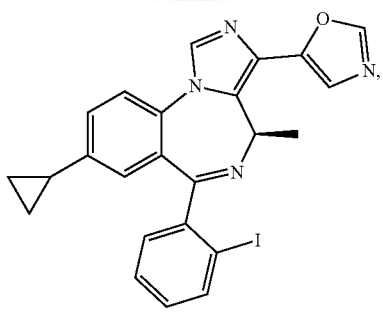
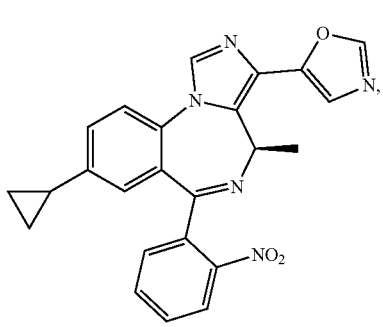
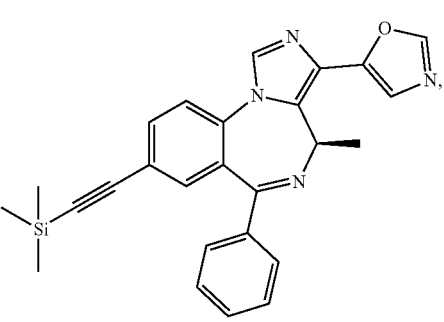
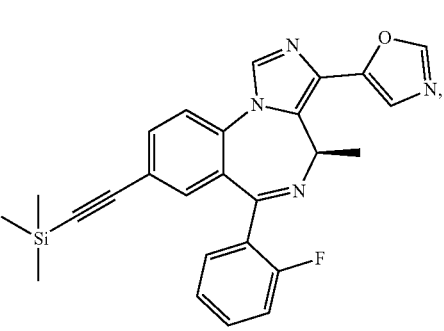
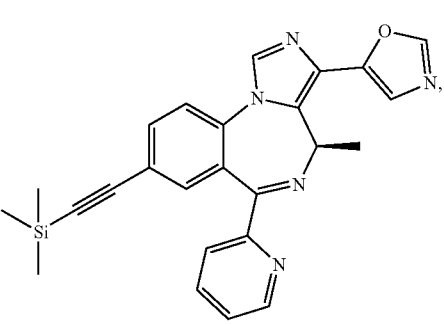

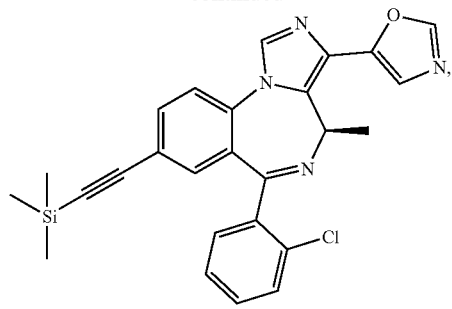
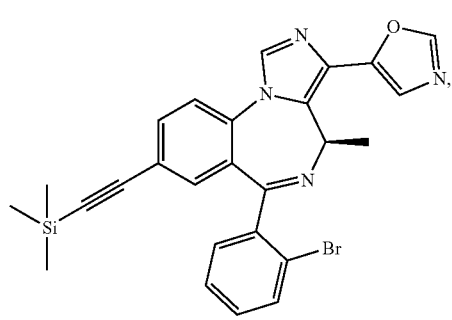
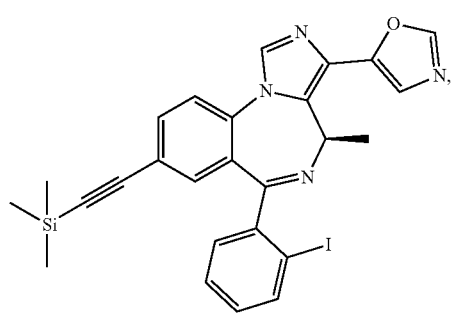
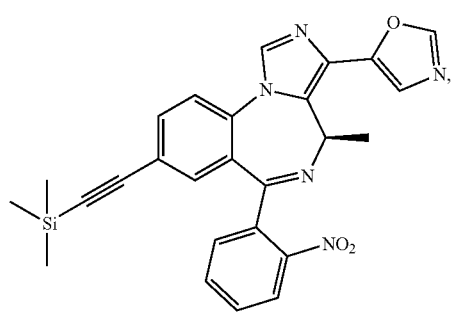
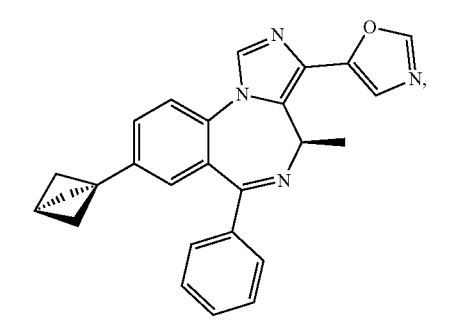
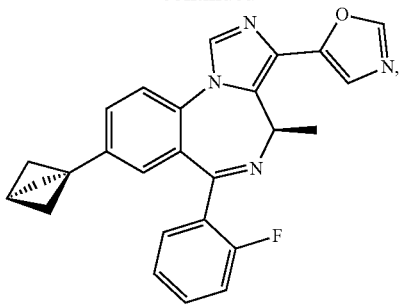
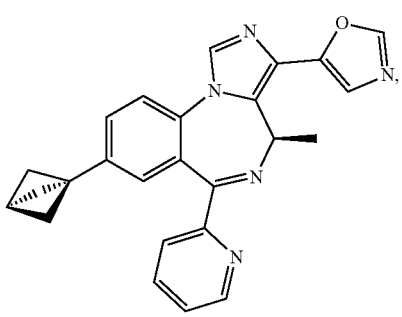
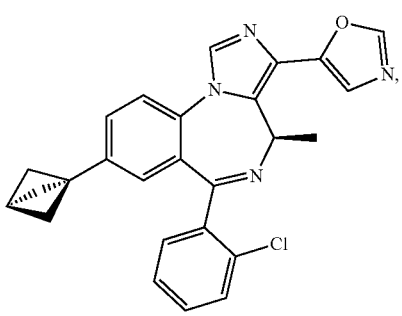
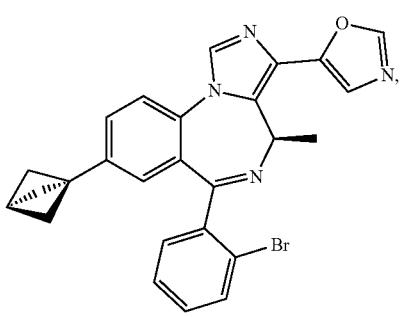
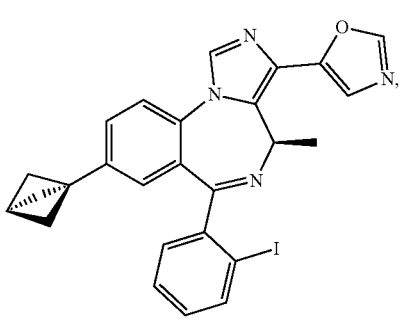

99
-continued
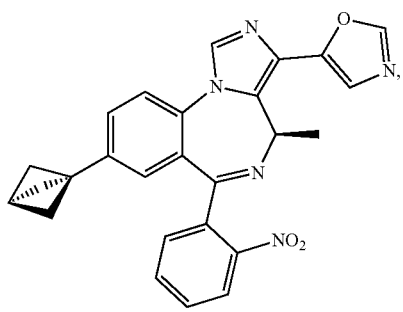
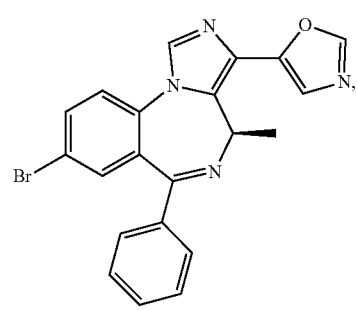
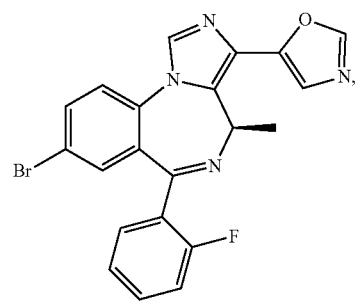
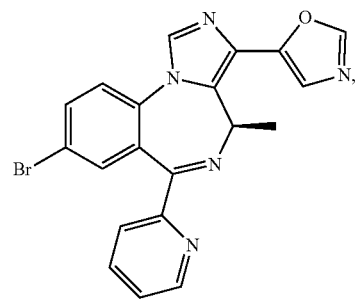
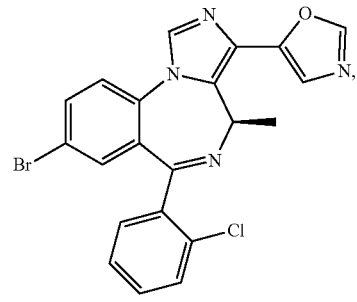
100
-continued
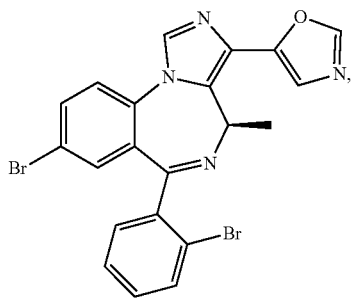
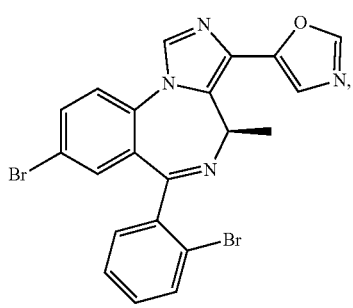
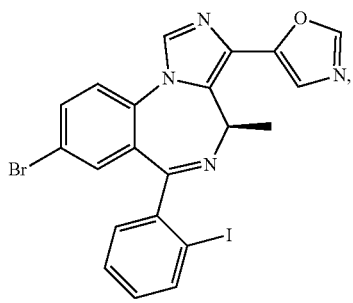
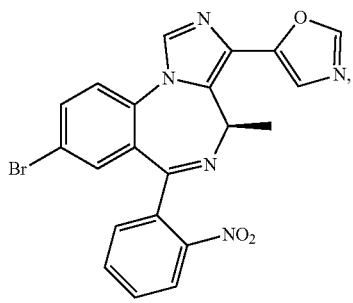
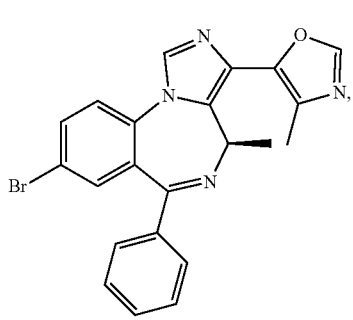

101
-continued
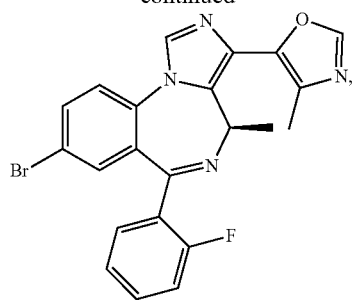
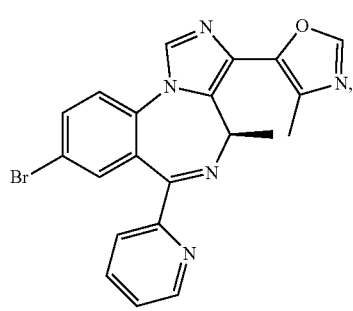
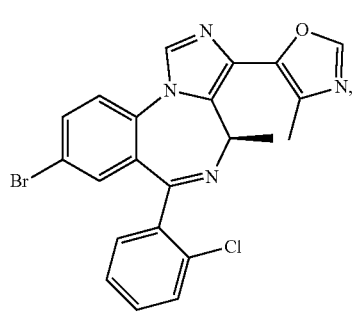
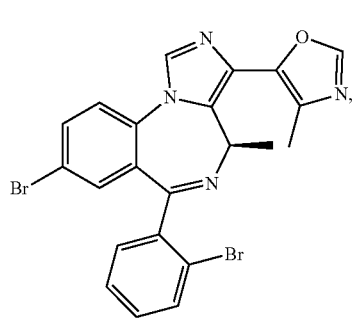
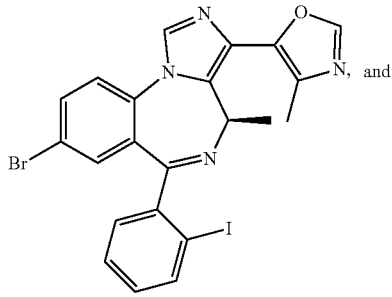
102
-continued
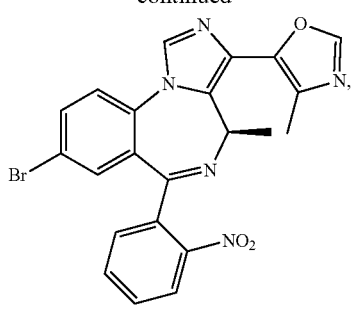
or a salt thereof.
14. The compound of claim 2, selected from the group consisting of:
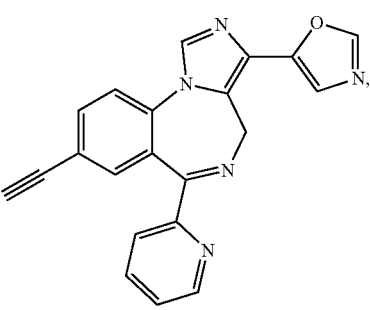
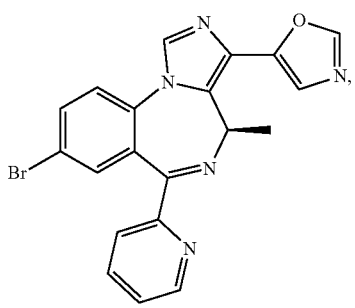
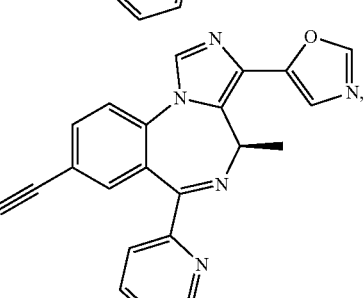
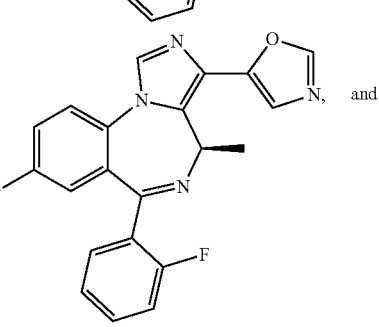

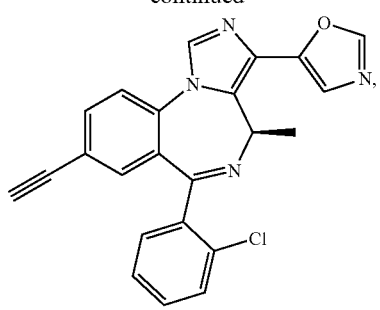
or a salt thereof.
15. The compound of claim 3, or a salt thereof, wherein R$_1$ is —C≡CH or Br; and X is N, C—H, C—F, or C—Cl.
16. The compound of claim 3, or a salt thereof, wherein R$_2$ is —H.
17. The compound of claim 3, selected from the group consisting of
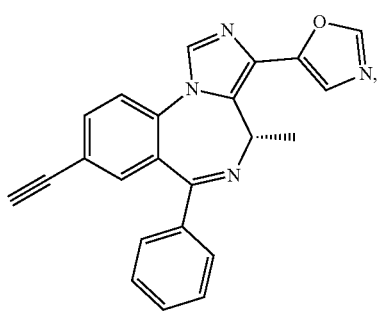
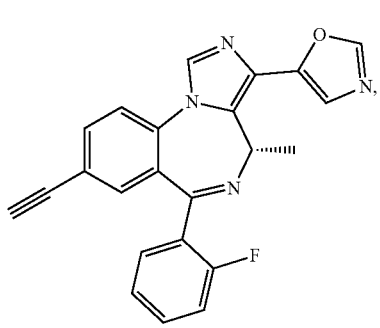
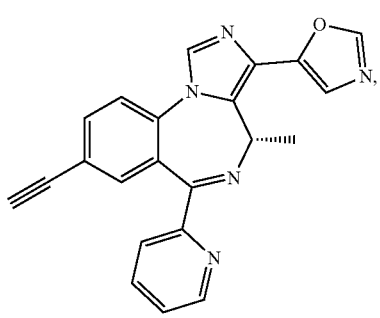
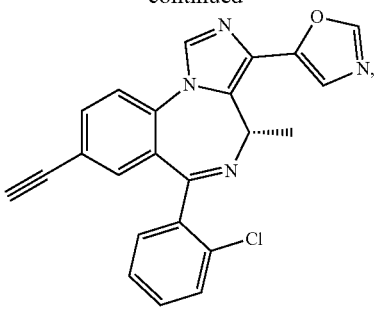
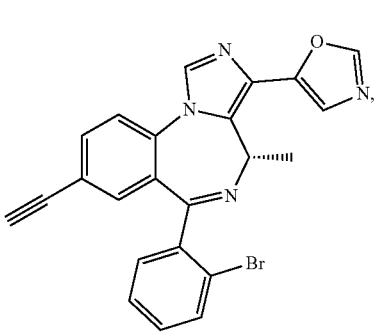
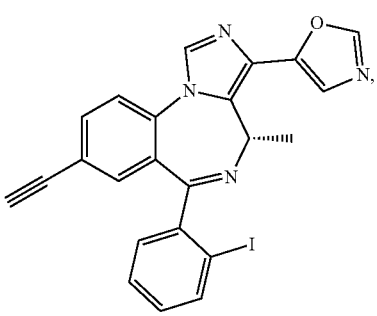
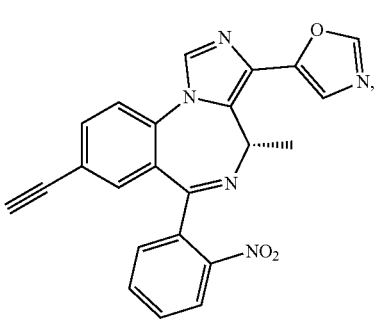
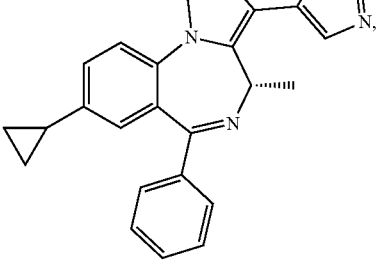

105
-continued
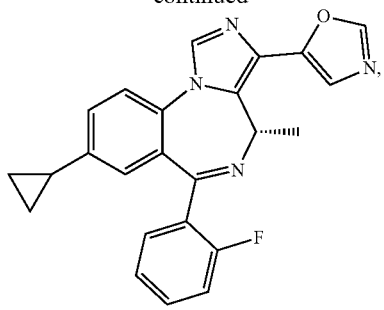
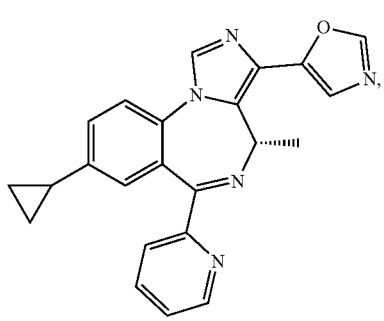
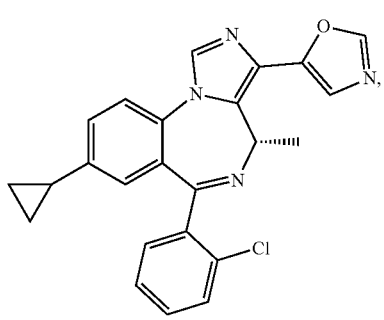
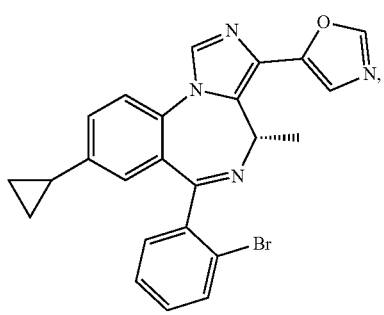
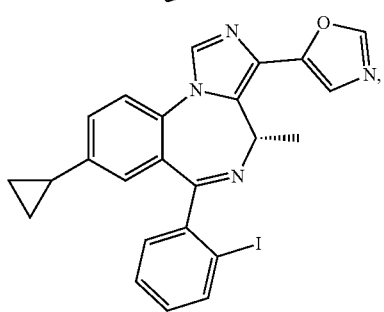
106
-continued
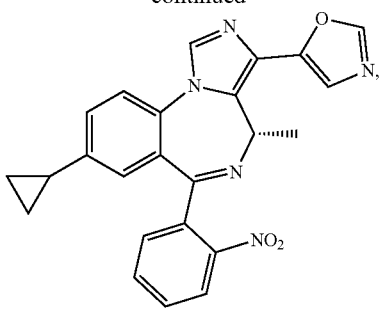
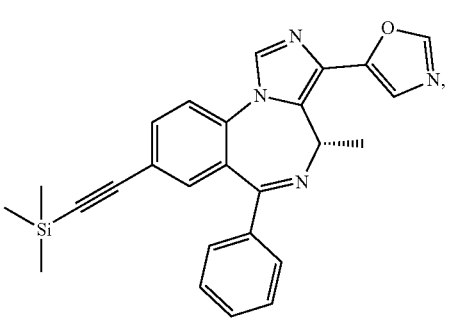
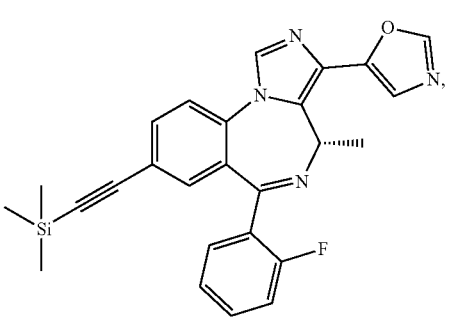
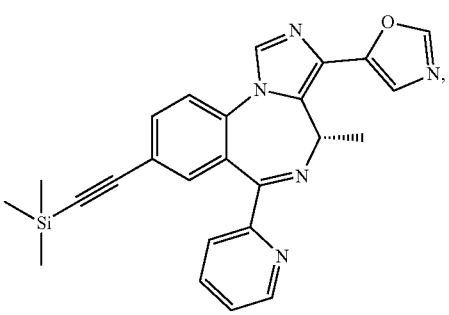
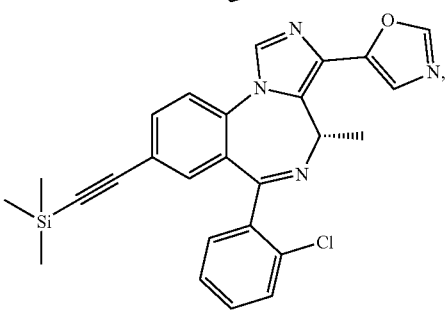

107
-continued
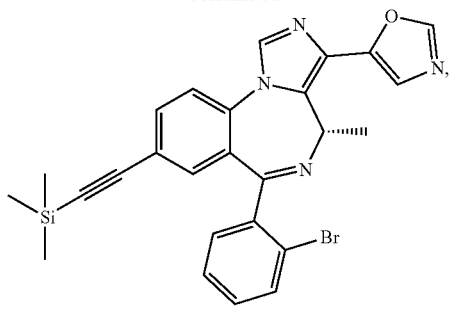
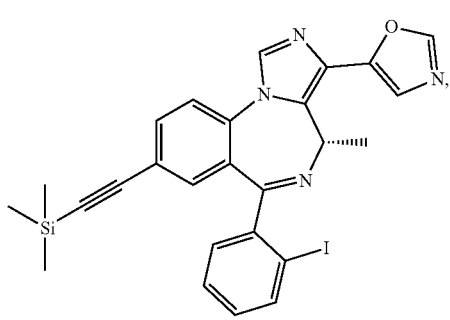
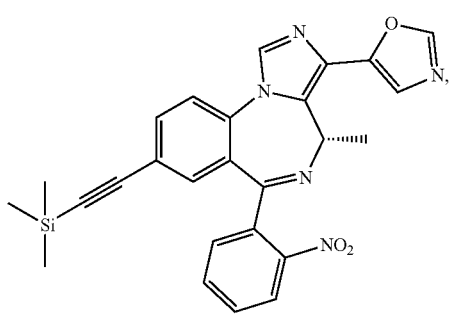
108
-continued
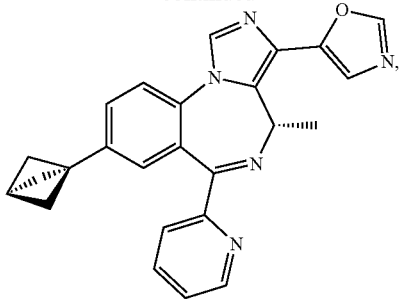
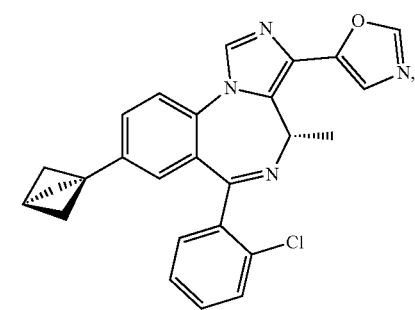
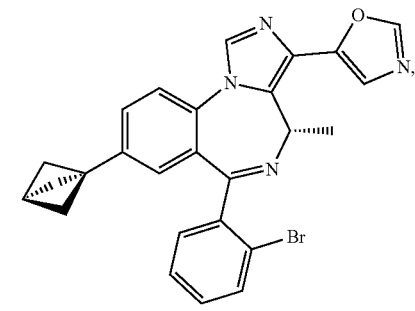
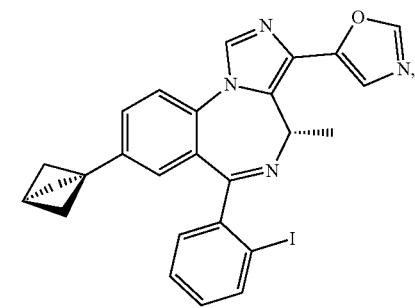
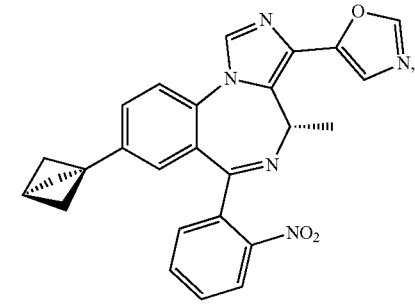

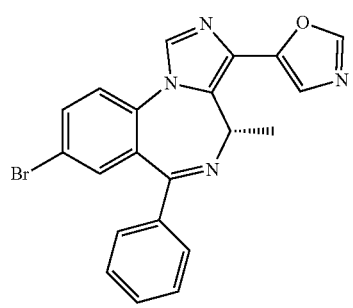
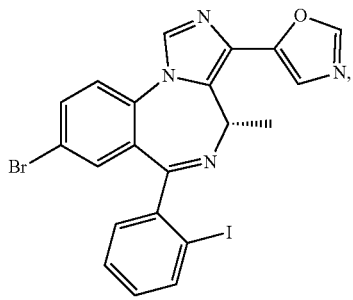
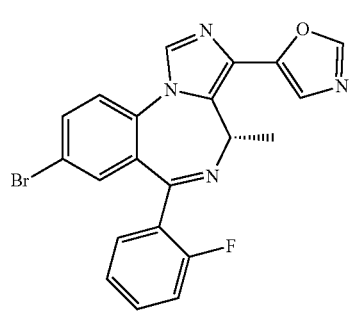
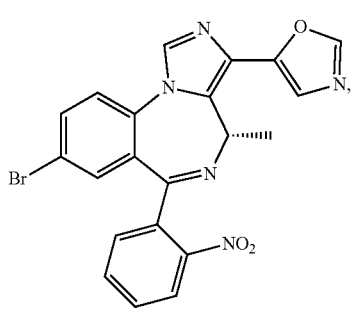
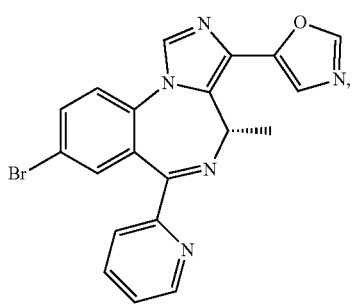
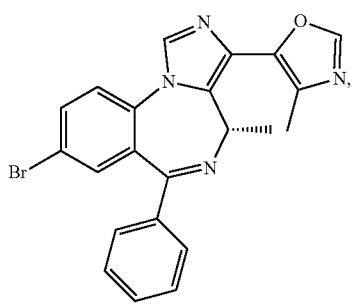
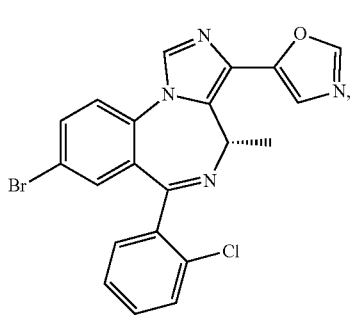
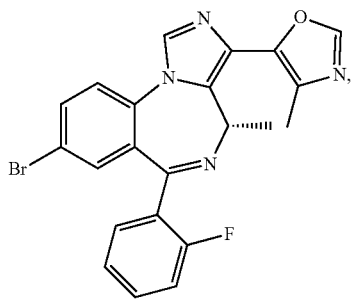
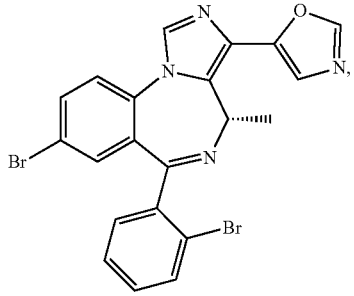
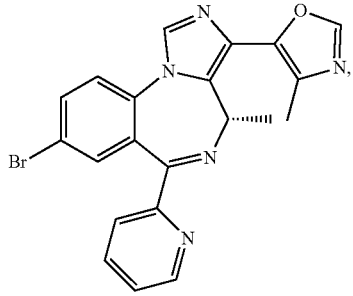

-continued

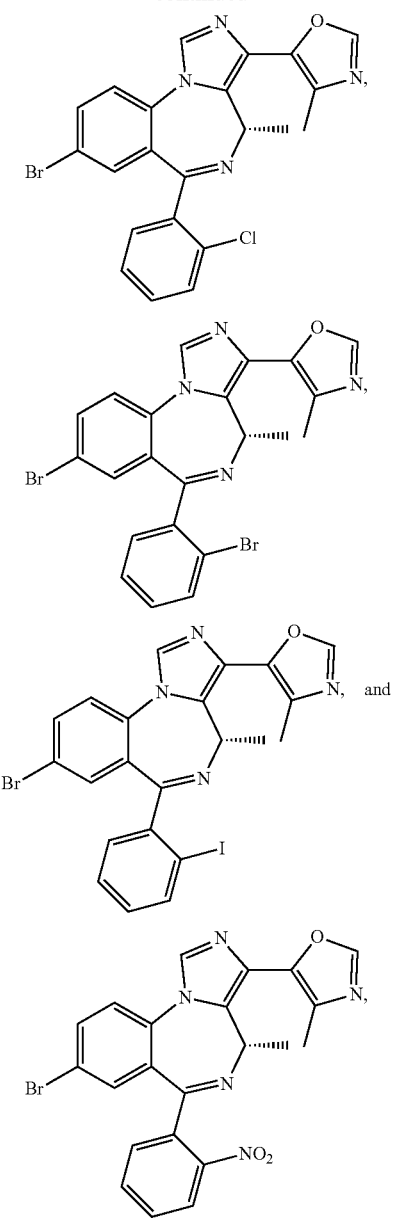

or a salt thereof.

18. The compound of claim 3 selected from the group consisting of:

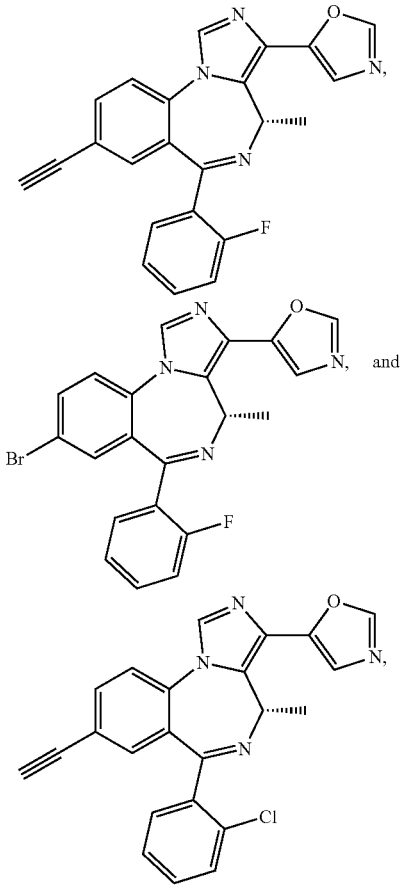

or a salt thereof.

19. A pharmaceutical composition comprising a compound according to claim 2 or a salt thereof; and a carrier.

20. A pharmaceutical composition comprising a compound according to claim 3 or a salt thereof; and a carrier.

21. A method of treating a disorder selected from an anxiety disorder, depression, epilepsy, schizophrenia and neuropathic pain in a subject in need of treatment, comprising administering to the subject an effective amount of a compound according to claim 2 or a salt thereof.

22. A method of treating a disorder selected from an anxiety disorder, depression, epilepsy, schizophrenia and neuropathic pain in a subject in need of treatment, comprising administering to the subject an effective amount of a compound according to claim 3 or a salt thereof.

* * * * *

UNITED STATES PATENT AND TRADEMARK OFFICE
CERTIFICATE OF CORRECTION

PATENT NO. : 10,259,815 B2  
APPLICATION NO. : 15/560002  
DATED : April 16, 2019  
INVENTOR(S) : James Cook et al.

Page 1 of 1

It is certified that error appears in the above-identified patent and that said Letters Patent is hereby corrected as shown below:

In the Specification

Column 1, Line 16:

Replace the following paragraph: [[This invention was made with government support under RO1 NS076517 and RO1 MH09463 awarded by the National Institutes of Health (NIH). The government has certain rights in the invention.]]

With: --This invention was made with government support under grant numbers R01 NS076517 and R01 MH096463 awarded by the National Institutes of Health. The government has certain rights in the invention.--

Signed and Sealed this  
Twenty-eighth Day of June, 2022

Katherine Kelly Vidal  
*Director of the United States Patent and Trademark Office*